(12) United States Patent
Kurihara et al.

(10) Patent No.: US 9,034,627 B2
(45) Date of Patent: May 19, 2015

(54) METHOD FOR PRODUCING GLUCOSIDASE, ENZYME COMPOSITION, AND METHOD FOR HYDROLYZING BIOMASS

(71) Applicant: Toray Industries, Inc., Tokyo (JP)

(72) Inventors: Hiroyuki Kurihara, Kamakura (JP); Shiomi Watanabe, Kamakura (JP); Katsushige Yamada, Kamakura (JP); Kazuhiko Ishikawa, Higashihiroshima (JP); Yasunobu Wada, Ikeda (JP); Yuji Kado, Ikeda (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/772,533

(22) Filed: Feb. 21, 2013

(65) Prior Publication Data

US 2013/0189761 A1    Jul. 25, 2013

Related U.S. Application Data

(63) Continuation of application No. 13/581,841, filed as application No. PCT/JP2011/051406 on Jan. 26, 2011.

(30) Foreign Application Priority Data

Mar. 1, 2010  (JP) ................................. 2010-044242

(51) Int. Cl.
*C12P 21/02*  (2006.01)
*C12N 9/42*   (2006.01)
*C12P 21/00*  (2006.01)

(52) U.S. Cl.
CPC ................. *C12N 9/42* (2013.01); *C12P 21/005* (2013.01); *C12Y 302/01021* (2013.01); *C12N 9/2445* (2013.01)

(58) Field of Classification Search
None
See application file for complete search history.

(56) References Cited

U.S. PATENT DOCUMENTS

2009/0111155 A1*  4/2009  White et al. .................. 435/171

FOREIGN PATENT DOCUMENTS

| JP | 2008-161125 A | 7/2008 |
| JP | 2008-535664 A | 9/2008 |
| WO | 2005/093072 A1 | 10/2005 |
| WO | WO 2010006152 A2 * | 1/2010 |

OTHER PUBLICATIONS

Hong et al., Cloning and functional expression of thermostable β-glucosidase gene from *Thermoascus aurantiacus*, Appl. Microbiol. Biotechnol., 2007, 73, 1331-39.*
Grinna et al., Size distribution and general structural features of N-linked oligosaccharides from the methylotrophic yeast, *Pichia pastoris*, Yeast, 1989, 5, 107-15.*
Kaper et al., Comparative structural analysis and substrate specificity engineering of the hyperthermostable β-glucosidase CelB from *Pyrococcus furious*, Biochemistry, 2000, 39, 4965-70.*
Hetti Palonene, et al., "Adsorption of *Trichoderma reesei* CBH I and EG II and their Catalytic Domains on Steam Pretreated Softwood and Isolated Lignin," *Journal of Biotechnology* 107 (2004), pp. 65-72.
Hideki Ohba, et al., "Improvement of the Thermostability of Pyruvate Decarboxylase by Modification with an Amylose Derivative," Biosci. *Biotech. Biochem.*, 59 (8), 1995, pp. 1581-1583.
Christian P. Kubicek, et al., *Trichoderma and Gliocladium: Basic Biology, Taxonomy and Genetics*, vol. 1, 1998, pp. 121-138.
Accession No. Genbank: YP-001540482, Nov. 2, 2007.
Accession No. Genbank: YP-256448, Jul. 8, 2005.
Accession No. Genbank: AAA72843.1, Apr. 26, 1993.
Accession No. Genbank: YP-024231.1, Jun. 9, 2004.
Accession No. Genbank: NP-111204.1, Apr. 4, 2001.
Accession No. Genbank: YP-001411058.1, Jul. 31, 2007.
Accession No. Genbank: 1QVB-A, Jul. 7, 1999.
Accession No. Genbank: NP-577802, Feb. 26, 2002.
Takashi Watanabe et al., "Purificication and properties of *Aspergillus niger* β-glucosidase," Eur. J. Biochem., vol. 209, No. 2, 1992, pp. 651-659.
Wilfried G.B. Voorhorst et al., "Characterization of the *celB* Gene Coding for β-GLucosidase from the Hyperthermophilic Archaeon *Pyrococcus furiosus* and Its Expression and Site-Directed Mutation in *Escherichia coli*," J. Bacteriol., vol. 177, No. 24, 1995, pp. 7105-7111.
N. Ortega et al., "Optimisation of β-Glucosidase Entrapment in Alginate and Polyacrylamide Gels," Bioresource Technology, vol. 64, No. 2, May 1998, pp. 105-111.
Shou Takashima et al., "Molecular Cloning and Expression of the Novel Fungal β-Glucosidase Genes from *Humicola grisea* and *Trichoderma reesei*," J. Biochem., vol. 125, No. 4, 1999, pp. 728-736.
S.E. Clark et al., "Effect of adding and removing *N*-glycosylation recognition sites on the thermostability of barley α-glucosidase," Protein Eng. Des. Sel., vol. 17, No. 3, 2004, pp. 245-249.

\* cited by examiner

*Primary Examiner* — Rebecca Prouty
*Assistant Examiner* — Todd M Epstein
(74) *Attorney, Agent, or Firm* — DLA Piper LLP (US)

(57) ABSTRACT

A method for producing a mutant glucosidase includes introducing DNA encoding a secretion signal sequence and DNA encoding Asn-X-Ser or Asn-X-Thr into DNA encoding a glucosidase derived from a thermophile, and introducing the resulting DNA into a eukaryotic microorganism and expressing it as a secretory protein. An enzyme composition contains the mutant glucosidase.

12 Claims, 22 Drawing Sheets

Fig. 1

```
TriReBGL    1  --MLPKDFQWGFATAAYQIEGAVDQDGRGPSIWDTFCAQPGKIADGSSGVTACDS----YN
AspNiBGL    1  --MLPKDLQWGFAKAAYQIEGAVDQDGRGPSIWDTFCAQPGKIADGSSGVTACDS----YN
PfuBGL      1  MAKFPKNFMFGYSWSGFQFEMGLPGSEVESDWWVWVHDKENIASGLVSGDLPENGPAYWH

TriReBGL   56  RTAEDIALLKSLGAKSYRFSISWSRIIPEGGRGDAVNQAG---------IDHYVKFVDDLL
AspNiBGL   56  RTAEDIALLKSLGAKSYRFSISSR---IPEGGRGDAVNQAG---------IDHYVKFVDDLL
PfuBGL     61  LYKQDHDIAEKLGMDCIRGGIEWARIFPKPTFDVKVDVEKDEEGNIISVDVPESTIKELE

TriReBGL  108  DAGITPFITLFHWDLPEGLHQRYGGLLNRTEFPLDFENYARVMFRALPKVRNWITFNEPL
AspNiBGL  106  DAGITPFITLFHWDL---LHQRYGGLLNRTEFPLDFENYARVMFRALPKVR----NWNEPL
PfuBGL    121  KIANMEALEHYRKIYSDWKERGKTFILNLYHWPLPLWIHDPIAVRKLGPDRAPAGWLDEK

TriReBGL  168  CSAIPGYGSGTFAPGRQSTSEPWTVGHNILVAHGRAVKAYRDDFKPASGDGQIGIVLNGD
AspNiBGL  160  CSAIPGYGSGSFAPGRQSTSEPWTVGHNILVAHGRAVKAYRDDFKPASGDGQIGIVLNGD
PfuBGL    181  TVVEFVKFAAFVAYHLDDLVDMWSTMNEPNVVYNQGYINLRSGFPPGYLSFEAAEKAKFN

TriReBGL  228  FTYPWDAADPADKEAAERRLEFFTAWFADPIYLGDYPASMRKQLGDRLPTFTPEERALVH
AspNiBGL  220  FTYPWDAADPADKE-----RLEFFTAWFADPIYLGDYPASMRKQLGDRLPTFTPEERALVH
PfuBGL    241  LIQAHIGAYDAIKE---------YSEKSVGVIYAFAWHDPLAEEYKDEVEEIRKKDYEFVT

TriReBGL  288  GSNDFYGMNHYTSNYIRhrSSPASADDTVGNVDVLFTNKQGNCIG---PETQSPWLRPCA
AspNiBGL  276  GSNDFYGMNHYTSNYIRhrSSPASADDTVGNVDVLFTNKQGNCIG---PETQSPWLRPCA
PfuBGL    293  ILHSKGKLDWIGVNYYSRLVYGAKDGHLVPLPGYGFMSERGGFAKSGRPASDFGWEMYPE

TriReBGL  345  AGFRDFLVWISKRYGYPPIYVTENGTSIKGESDLPKEKILEDDFRVKYYNEYIRAMVTAV
AspNiBGL  333  AGFRDFLVWTSKRYGSPPIYVTENGTSIKGESDLPNEKILEDDFRVKYYNEYIRAMVTAV
PfuBGL    353  G-LENLLKYLNNAYELP-MIITENG--------------MADAADRYRPHYLVSHLKAVYNA

TriReBGL  405  ELDGVNVKGYFAWSLMDNFEWADGYVTRFGVTYVDYENGQKRFP---------KKSA
AspNiBGL  393  ELDGVNVR-------------------FGVTYVDYENGQKRFP---------KKSA
PfuBGL    399  MKEGADVRGYLHWSLTDNYEWAQGFRMRFGLVYVDFETKKRYLRPSALVFREIATQKEIP

TriReBGL  453  KSLKPLFDELIAAA-
AspNiBGL  421  KSLKPLFDELIAAA-
PfuBGL    459  EELAHLADLKFVTRK
```

Fig. 2-1

```
gPfuBGL      1  --MAKFPKNFMFGYSWSGFQFEMG----LPGSE-VESDWWVWVHDKENIASGLVSGDLPEN
ThAggBGY     1  ---MKFPKDFMIGYSSSPFQFEAG----IPGSEDPNSDWWVWVHDPENTAAGLVSGDFPEN
CmGHFP       1  --MIKFPSDFRFGFSTVGTQHEMG----TPGSE-FVSDWYVWLHDPENIASGLVSGDLPEH
SaBGAL       1  --MLSFPKGFKFGWSQSGFQSEMG----TPGSEDPNSDWHVWVHDRENIVSQVVSGDLPEN
SsoBGAL      1  --MYSFPNSFRFGWSQAGFQSEMG----TPGSEDPNTDWYKWVHDPENMAAGLVSGDLPEN
TvBGAL       1  MVENNFPEDFKFGWSQSGFQSEMG----YDNAMDDKSDWYVWVHDKENIQSGLVSGDMPEN
PtBGAL       1  ------MLPKNFLLGFSLAGFQSEMG----ISD-PDSNSDWWLWVHDPVNIRTGLVSGDLPEN
FnGHFP       1  ---MMFPKDFLFGVSMSGFQFEMGNPQDAEEVDLNTDWYVWVRDIGNIVNGVVSGDLPEN gPfuBGL     55  GPAYWNRTKQDHDIAEKLGMDCIRGGIEWARIFPKPTFDVKVDVEKDEEG-NIISVDVPE
ThAggBGY    55  GPGYWNLNQNDHDLAEKLGVNTIRVGVEWSRIFPKPTFNVKVPVERDENG-SIVHVDVDD
CmGHFP      55  GPGYWDLYKQDHSIARDLGLDAAWITIEWARVFPKPTFDVKVKVDEDDGG-NVVDVEVNE
SaBGAL      56  GPGYWGNYKRFHDEAEKIGLNAVRINVEWSRIFPRPLPKPEMQTGTDKENSPVISVDLNE
SsoBGAL     56  GPGYWGNYKTFHDNAQKMGLKIARLNVEWSRIFPNPLPRP---QNFDESKQDVTEVEINE
TvBGAL      58  GPGYWNNYKSFHEAAQNMGLKMARIGVEWSRLFPEPFPEKIMADAKNN------SLEINN
PtBGAL      53  GIGYWDLYKKYNGLAVQTGMNAARLGVEWSRIFPKSTEEVKVMEDYKDD---DLISVDVNE
FnGHFP      58  GSWYWKQYGKVHQLAADFGMDVIRIGTEWSRIFPVSTQSVEY---------------GSP gPfuBGL    114  STIKELEKIANMEALEHYRKIYSDWKERGKTFILNLYHWPLPLWIHDPIAVRKLGPDRAP
ThAggBGY   114  KAVERLDELANKEAVNHYVEMYKDWVERGRKLILNLYHWPLPLWLHNPIMVRRMGPDRAP
CmGHFP     114  SALEELRRLADLNAVNHYRGILSDWKERGGLLVINLYHWAMPTWLHDPIAVRKNGPDRAP
SaBGAL     116  SKLREMDNYANHEALSHYRQILEDLRNRGFHIVLNMYHWTLPIWLHDPIRVRR-GDFTGP
SsoBGAL    113  NELKRLDEYANKDALNHYREIFKDLKSRGLYFILNMYHWPLPLWLHDPIRVRR-GDFTGP
TvBGAL     112  NILSELDKYVNKDALNHYIEIFNDIKNRNIDLIINMYHWPLPVWLSDPVSVRK-GIKTER
PtBGAL     111  GSLEKLDRLANQKAINRYMEIFNNIKENNMTLIVNVYHWPIPIYLHDPIEARNSGLSNKR
FnGHFP     103  DMLEKLDKLANQKAVSHYRKIMEDIKAKGLKLFVNLYHFTLPIWLHDPIAVHK-GEKTDK gPfuBGL    174  AGWLDEKTVVEFVKFAAFVAYHLDDLVDMWSTMNEPNVVYNQGYINLRSGFPPGYLSFEA
ThAggBGY   174  SGWLNEESVVEFAKYAAYIAWKMGELPVMWSTMNEPNVVYEQGYMFVKGGFPPGYLSLEA
CmGHFP     174  SGWLDKRSVIEFTKFAAFIAHELGDLADMWYTMNEPGVVITEGYLYVKSGFPPGYLDLNS
SaBGAL     175  TGWLNSRTVYEFARFSAYVAWKLDDLASEYATMNEPNVVWGAGYAFPRAGFPPNYLSFRL
SsoBGAL    172  SGWLSTRTVYEFARFSAYIAWKFDDLVDEYSTMNEPNVVGGLGYVGVKSGFPPGYLSFEL
TvBGAL     171  SGWLNDRIVQLFALFSSYIVYKMEDLAVAFSTMNEPNVVYGNGFINIKSGFPPSYLSSEF
PtBGAL     171  NGWLNHKTVVEFVKYAKYLAWKFSDVADMFSIMNEPNVVFGNGYFNVKSGFPPAFPSVHG
FnGHFP     162  IGWISDATPIEFAKYAEYMAWKFADIVDMWASMNEPHVVSQLGYFAINAGFPPSYFNPSW gPfuBGL    234  AEKAKFNLIQAHIGAYDAIKEYSEKSVGVIYAFAWHDPLAE--EYKDEVEEIRKKDYEFV
ThAggBGY   234  ADKARRNMIQAHARAYDNIKRFSKKPVGLIYAFQWFELLEG---PAEVFDKFKSSKLYYFT
CmGHFP     234  LATAGKHLIEAHARAYDAIKAYSRKPVGLVYSFADYQPLRQ--GDEEAVKEAKGLDYSFF
SaBGAL     235  SEIAKWNIIQAHARAYDAIKSVSKKSVGIIYANTSYYPLRP-QDNEAVEIAERLNRWSFF
SsoBGAL    232  SRRAMYNIIQAHARAYDGIKSVSKKPVGIIYANSSFQPLTD-KDMEAVEMAENDNRWWFF
TvBGAL     231  ASKVKNNILKAHSLAYDSMKKITDKPVGIIYANTYFTPLDPEKDNDAIAKADSDAKWSFF
PtBGAL     231  GLLAKKHEIEAIARSYDAMKEITKKPVGLIMANSDVQPLTD-EDKEAAEMATYNDRYSFI
FnGHFP     222  YIKSLENEAKAHNLSYDAIKKYTNNPVGVIYSFTWYDTVNK-DDKESFENAMDLTNWRFI
```

Fig. 2-2

```
gPfuBGL    292  TILHS---------------------KGKLDWIGVNYYSRLVYGAKDGH------
ThAggBGY   292  DIVSKGSSIINVEY------------RRDLANRLDWLGVNYYSRLVYKIVDDK------
CmGHFP     292  DAPIKGELMG--VT------------RDDLKGRLDWIGVNYYTRAVLRRRQDAGRA----
SaBGAL     294  DSIIKGEITSEGQ-------------NVREDLRNRLDWIGVNYYTRTVVTKAESG------
SsoBGAL    291  DAIIRGEITRGNEK------------IVRDDLKGRLDWIGVNYYTRTVVKRTEKG------
TvBGAL     291  DPLIKGDKSLGIN-------------GNKLDWIGINYYTRTMLRKDGDG------
PtBGAL     290  DPLRVGEMKWADEVTAGNPIGEKSNIDRSDLKNKLDWIGVNYYTRAVVKKSGNG------
FnGHFP     281  DMVKD---------------------KTDYIGVNYYTRAVIDRLPTTIDFGEF gPfuBGL    320  ---LVPLPGYGFMSERGGFAKSGRPASDFGWEMYPEGLENLLKYLNNAYELPMIITENGM
ThAggBGY   333  ---PIILHGYGFLCTPGGISPAENPCSDFGWEVYPEGLYLLLKELYNRYGVDLIVTENGV
CmGHFP     334  ---SVAVVDGFGYSCEPGGVSNDRRPCSDFGWEIYPEGVYNVLMDLWRRYRMPMYITENGI
SaBGAL     336  ---YLTLPGYGDRCERNSLSLANLPTSDFGWEFFPEGLYDVLLKYWNRYGLPLYVMENGI
SsoBGAL    334  ---YVSLGGYGHGCERNSVSLAGLPTSDFGWEFFPEGLYDVLTKYWNRYHLYMYVTENGI
TvBGAL     327  ---YISLKGYGHSGSPNTVTNDKRPTSDIGWEFYPEGLEYVIMNYWNRYKLPMYVTENGI
PtBGAL     344  ---YTTLKGYGHSATAGMPSRAGRDVSDFGWEFYPEGLVNVLSSYWKRYHIPMIVTENGV
FnGHFP     313  KMNWYTLRGYGYSCEEGGFSLSGRPASEFGWEIYPEGLYNILIHVYNRYKKDIYVTENGI gPfuBGL    377  ADAADRYRPHYLVSHLKAVYNAMKEGADVRGYLHWSLTDNYEWAQGFRMRFGLVYVDFET
ThAggBGY   390  SDSRDALRPAYLVSHVYSVWKAANEGIPVKGYLHWSLTDNYEWAQGFRQKFGLVMVDFKT
CmGHFP     392  ADEHDKWRSWFIVSHLYQIhrAMEEGVDVRGYFHWNLIDNLEWAAGYRMRFGLVYVDYAT
SaBGAL     393  ADDADYQRPYYLVSHIYQVhrALNEGVDVRGYLHWSLADNYEWSSGFSMRFGLLKVDYLT
SsoBGAL    391  ADDADYQRPYYLVSHVYQVhrAINSGADVRGYLHWSLADNYEWASGFSMRFGLLKVDYNT
TvBGAL     384  ADNGDYQRPYYLVSHIASVLRAINKGANVKGYLHWSLVDNYEWALGFSPKFGLIGYDENK
PtBGAL     401  ADSIDRLRPRYLVSHIKSVEKALSMGMDIRGYLHWSLIDNYEWASGFSMKFGLYGIDLNN
FnGHFP     373  ADSKDKYRSLFIISHLYAIEKALNEGIPIKGYLHWSIIDNFEWAKGYSKRFGLAYTDLST gPfuBGL    437  KKRYLRPSALVFREIATQKEIPEELAHLADLKFVTRK--
ThAggBGY   450  KKRYLRPSALVFREIATHNGIPDELQHLTLIQ-------
CmGHFP     452  KRRYFRPSALVMREVAKQKAIPDYLEHYIKPPRIE----
SaBGAL     453  KRLYWRPSALVYREITRSNGIPEELEHLNRVPPIKPLRH
SsoBGAL    451  KRLYWRPSALVYREIATNGAITDEIEHLNSVPPVKPLRH
TvBGAL     444  K-LYWRPSALVYKEIATKNCISPELKHLDSIPPINGLRK
PtBGAL     461  KKIQhrPSALVFKEIANANGVPEEFEWMADQHQNS----
FnGHFP     433  KKYIPRPSMYIFREIIKDKSIDKFKGYDPYNLMKF----
```

METHOD FOR PRODUCING GLUCOSIDASE, ENZYME COMPOSITION, AND METHOD FOR HYDROLYZING BIOMASS

RELATED APPLICATIONS

This application is a continuation of U.S. application Ser. No. 13/581,841, filed Aug. 30, 2012, which is a §371 of International Application No. PCT/JP2011/051406, with an international filing date of Jan. 26, 2011 (WO 2011/108312 A1, published Sep. 9, 2011), which is based on Japanese Patent Application No. 2010-044242, filed Mar. 1, 2010, the subject matter of which is incorporated herein by reference.

This disclosure contains a Sequence Listing which has been submitted in ASCII format via EFS-Web and is hereby incorporated by reference in its entirety. The ASCII copy, created on Jan. 29, 2013, is named HIR12128.txt and is 175,796 bytes in size.

TECHNICAL FIELD

This disclosure relates to a method for producing a glycosylated mutant glucosidase derived from a thermophile, an enzyme composition containing this enzyme, and a method for hydrolyzing biomass using the enzyme composition.

BACKGROUND

Various techniques are available for saccharification of cellulose, among which an enzymatic saccharification method, which uses mild reaction conditions and achieves high sugar yield, has become the mainstream of development.

Cellulase, which is a cellulose degrading enzyme, is roughly classified into cellobiohydrolase, which acts on the crystalline regions of cellulose, and endoglucanase, which reduces the molecular weight by acting on within the cellulose molecular chain. These cellulases are known to be inhibited by cellobiose, which is one of the products of cellulose degradation. Meanwhile, β-glucosidase is an enzyme that acts on a water-soluble oligosaccharide or cellobiose and catalyzes a hydrolysis reaction of the β-glycosidic bond. Particularly, β-glucosidase is an enzyme necessary for the acquisition of plenty of glucose, which is useful as a fermentation raw material. Also, it is known that the reactions mediated by cellobiohydrolase or endoglucanase are inhibited by the accumulation of cellobiose, which is produced by cellulose degradation. That is, β-glucosidase has an effect of greatly improving the cellulose degradation efficiency, owing to its capability of drastically reducing the accumulation of cellobiose produced by cellulose degradation.

Cellulose is contained abundantly in herbaceous plants and woody plants, which are collectively called cellulosic biomass. Cellulosic biomass contains, in addition to cellulose, hemicellulose such as xylan and arabinan, and lignin. Particularly, being an aromatic polymer compound, lignin contained in cellulosic biomass is known to act in an inhibitory manner in the enzymatic saccharification by cellulase derived from filamentous fungi. Although the mechanism of inhibition of cellulase derived from filamentous fungi by lignin has not been entirely elucidated yet, the reduced degradation efficiency caused by adsorption of cellulase to lignin is proposed as one of the causes (P. Hetti et al., Journal of Biotechnology, 107, 65 to 72 (2004)).

A heat-resistant enzyme is highly stable and retains its activity for a long time even under high temperature conditions; therefore, the application of a heat-resistant enzyme as an industrial enzyme is under study. A large number of heat-resistant enzymes have been confirmed among the enzymes possessed by thermophiles or hyperthermophiles.

Also with regard to heat-resistant β-glucosidase, it has been identified from several species of thermophiles or hyperthermophiles. Specifically, heat-resistant β-glucosidase has been identified from organisms such as *Pyrococcus furiosus, Pyrococcus horikoshii, Thermotoga maritima, Sulfolobus shibatae,* and *Clostridium thermocellum.*

Cellulase or β-glucosidase derived from filamentous fungi is known to be glycosylated (P. Christian et al., *Trichoderma* and *Gliocladium*: Basic Biology, Taxonomy and Genetics, Vol. 1, 121 to 138 (1998)). As a general function of a sugar chain in such a glycosylated protein, effects such as improving protein solubility, improving physical stability, and improving protease resistance are known (H. Ohba et al., Biosci. Biotech. Biochem., 59, 1581 to 1583 (1995)). As a function conferred by the possession of a sugar chain by a saccharification enzyme such as cellulase, it is disclosed that glycosylation of xylanase with N-linked sugar chains results in an increased expression level of xylanase (WO/2005/093072).

SUMMARY OF INVENTION

Technical Problem

An object of the present invention is to provide a glycosylated mutant glucosidase derived from a thermophile, and further, to provide an enzyme composition exhibiting high degradation efficiency in the process of hydrolysis of cellulose, particularly lignin-containing lignocellulose, by mixing the above glucosidase and cellulase.

Solution to Problem

The present inventors conducted an intensive research to achieve the aforementioned object. As a result, they have found that a glycosylated mutant glucosidase derived from a thermophile can be applied to cellulose degradation.

That is, the present invention is composed of the following technical means.

(1) A method for producing a mutant glucosidase derived from a thermophile that has selectively attached thereto a sugar chain and also has a glucosidase activity, comprising:
  (i) preparing DNA encoding a mutant glucosidase derived from a thermophile by introducing a DNA sequence encoding Asn-X-Ser or Asn-X-Thr (wherein, X is any amino acid except proline) into DNA encoding a glucosidase derived from a thermophile that is originally devoid of a glycosylation sequence, and further, adding a DNA sequence encoding a secretion signal sequence to the DNA encoding the mutant glucosidase,
  (ii) introducing the DNA encoding the mutant glucosidase to which the DNA sequence encoding the secretion signal sequence has been added into an eukaryotic microorganism so that a mutant glucosidase encoded by the DNA of the mutant glucosidase is expressed as a secretory protein, and
  (iii) isolating and purifying the mutant glucosidase thus expressed as a secretory protein.
(2) The method for producing a mutant glucosidase according to (1), wherein the sugar chain is a high mannose type sugar chain.
(3) The method for producing a mutant glucosidase according to (1) or (2), wherein the glucosidase derived from a thermophile is a glucosidase derived from a thermophile selected from the group consisting of the genus *Sulfolobus*, the genus *Thermoplasma*, the genus *Caldivirga*, the genus *Thermosphaera*, the genus *Pyrococcus*, the genus *Picrophilus*, the genus *Caldivirga*, and the genus *Fervidobacterium*.

(4) The method for producing a glucosidase according to any of (1) to (3), wherein the glucosidase derived from a thermophile is a protein comprising:
   (i) a same amino acid sequence as any of amino acid sequences shown in SEQ ID NO: 4, SEQ ID NO: 8, SEQ ID NO: 10, SEQ ID NO: 12, SEQ ID NO: 14, SEQ ID NO: 16, SEQ ID NO: 18, and SEQ ID NO: 20, or
   (ii) an amino acid sequence having 85% or more identity with any of amino acid sequences shown in SEQ ID NO: 4, SEQ ID NO: 8, SEQ ID NO: 10, SEQ ID NO: 12, SEQ ID NO: 14, SEQ ID NO: 16, SEQ ID NO: 18, and SEQ ID NO: 20, and also a β-glucosidase activity.

(5) The method for producing a mutant glucosidase according to any of (1) to (4), wherein the eukaryotic microorganism is *Pichia pastoris*.

(6) The method for producing a mutant glucosidase according to any of (1) to (5), wherein the secretion signal sequence is a α factor secretion signal sequence.

(7) The method for producing a mutant glucosidase according to any of (1) to (6), wherein the mutant glucosidase derived from a thermophile comprises an amino acid sequence shown in any of SEQ ID NO: 6, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, and SEQ ID NO: 56.

(8) An enzyme composition for saccharification of biomass comprising cellulase and the mutant glucosidase derived from a thermophile obtained by the production method according to any of (1) to (7).

(9) The enzyme composition for saccharification of biomass according to (8), wherein the cellulase is a mixture of cellulases derived from filamentous fungi.

(10) The enzyme composition for saccharification of biomass according to (8) or (9), wherein the mixture of cellulases derived from filamentous fungi is a mixture of cellulases derived from the genus *Trichoderma*.

(11) A method for hydrolyzing biomass, comprising using the enzyme composition according to any of (8) to (10).

(12) The method for hydrolyzing biomass according to (11), comprising filtering a hydrolysate obtained by the aforementioned enzyme composition through an ultrafiltration membrane, and separating and recovering the used enzyme composition.

The present specification encompasses the contents described in the specification and/or drawings of JP Patent Application No. 2010-044242, based on which the present application claims priority.

Advantageous Effects of Invention

Compared to the use of a glucosidase derived from a thermophile with an unglycosylated cellulase mixture, the glycosylated mutant glucosidase derived from a thermophile obtained by the present invention can achieve higher cellulose degradation efficiency in the hydrolysis of cellulosic biomass. This effect is prominent particularly in the hydrolysis of lignocellulose. Also, the glycosylated mutant glucosidase derived from a thermophile according to the present invention has low adsorptivity for cellulosic biomass, particularly for lignocellulose, and for an ultrafiltration membrane, and also for an ultrafiltration membrane used for separation of a sugar solution from the hydrolysate, and thus achieves excellent enzyme recovery from the hydrolysate.

BRIEF DESCRIPTION OF DRAWINGS

FIG. 1 shows an alignment of a β-glucosidase derived from *Pyrococcus furiosus* (PfuBGL) shown in SEQ ID NO: 4, a β-glucosidase derived from *Trichoderma reesei* (TriReBGL) shown in SEQ ID NO: 1, and a β-glucosidase derived from *Aspergillus niger* (AspNgBGL) shown in SEQ ID NO: 2 in Example 1. The glycosylation sequence in SEQ ID NO: 1 and SEQ ID NO: 2 was underlined, and the glycosylation sequence-introduction site (H60, L61, and Y62) in SEQ ID NO: 4 was similarly underlined.

FIG. 2-1 shows an alignment of the amino acid sequence of SEQ ID NO: 6 (gPfuBGL) and the amino acid sequences of SEQ ID NO: 8 (ThAggBGY), SEQ ID NO: 10 (CmGHFP), SEQ ID NO: 12 (SaBGAL), SEQ ID NO: 14 (SsoBGAL), SEQ ID NO: 16 (PtBGAL), SEQ ID NO: 18 (TvBGAL), and SEQ ID NO: 20 (FnGHFP) in Example 2. The glycosylation sequence Asn-Arg-Thr (N-R-T) inserted in the sequence of SEQ ID NO: 6 was underlined. Also, the site corresponding to the glycosylation site Asn-Arg-Thr (N-R-T) in the sequence of SEQ ID NO: 6 in SEQ ID NO: 8, SEQ ID NO: 10, SEQ ID NO: 12, SEQ ID NO: 14, SEQ ID NO: 16, SEQ ID NO: 18, or SEQ ID NO: 20 was similarly underlined.

FIG. 2-2 is a sequel to FIG. 2-1.

DESCRIPTION OF EMBODIMENTS

Figure 3:
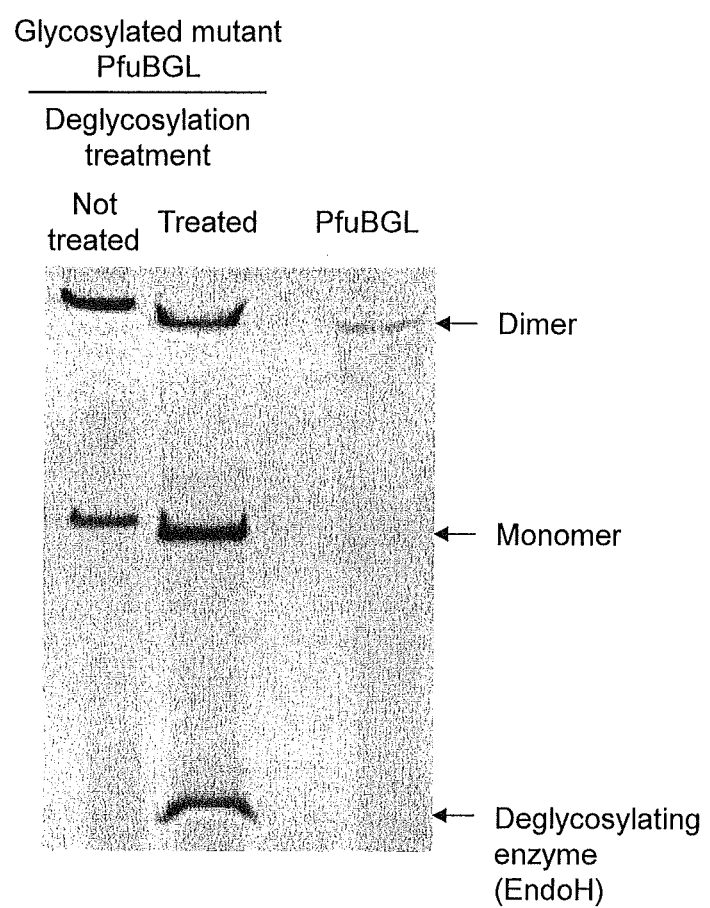
FIG. 3 is a diagram showing the band pattern of polyacrylamide gel electrophoresis for PfuBGL (left) prepared in Comparative Example 1 and the glycosylated mutant PfuBGL prepared in Example 2 without EndoH treatment (right) and with EndoH treatment (middle). A reduction in the molecular weight of the glycosylated mutant PfuBGL by EndoH treatment is confirmed.

Hereinbelow, the present invention will be described in detail.

The "glucosidase" in the present invention refers to an enzyme having an activity of hydrolyzing a disaccharide having a β-glycosidic bond (i.e., the β-glucosidase activity). Although a group of enzymes belonging to β-glucosidase is listed under the Enzyme Commission (EC) No: EC 3.2.1.21, a protein not belong to β-glucosidase in terms of EC number but having the aforementioned β-glucosidase activity is also encompassed by glucosidase in the present invention. Examples of the glucosidase include galactosidase, mannosidase, and a glucosidic bond hydrolase family protein.

In the present invention, a thermophile is a generic term for a group of microorganisms that can live at 50° C. or higher, and particularly, a hyperthermophile refers to a group of microorganisms that can live at 80° C. or higher. Examples of the thermophile include the genus *Sulfolobus*, the genus *Thermoplasma*, the genus *Caldivirga*, the genus *Thermosphaera*, the genus *Pyrococcus*, the genus *Picrophilus*, the genus *Caldivirga*, and the genus *Fervidobacterium*.

The glucosidase derived from a thermophile is publicly known, and for example, it is registered at GenBank under NP_577802, which can be used in the present invention. Preferably, the glucosidase derived from a thermophile has the amino acid sequence shown in SEQ ID NOs: 4, 8, 10, 12, 14, 16, 18, and 20. More preferably, the glucosidase derived from a thermophile consists of the amino acid sequence shown in SEQ ID NOs: 4, 8, 10, 12, 14, 16, 18, and 20. In the present invention, the glucosidase derived from a thermophile also encompasses a protein having the amino acid sequence of SEQ ID NOs: 4, 8, 10, 12, 14, 16, 18 and 20 that has been subjected to one or multiple deletion, substitution, addition, or insertion, or deletion, substitution, addition, or insertion of one or a plurality of amino acids, and having a β-glucosidase activity. Here, the range of "one or a plurality" is not particularly limited; however, it is preferably 10 or less, more preferably five or less, particularly preferably four or less, or one or two. Also, in the present invention, the glucosidase derived from a thermophile also encompasses a protein having an amino acid sequence with 85% or more, more preferably 90% or more, and most preferably 95% or more identity with the amino acid sequence shown in SEQ ID NOs: 4, 8, 10, 12, 14, 16, 18, and 20 according to calculation using The Basic Local Alignment Search Tool (BLAST) at the National Center for Biological Information and the like (for example, default parameter(s), i.e., the initially set parameter(s)), preferably consisting of the above amino acid sequence, and having the β-glucosidase activity. Here, the term "identity" refers to the percentage of the identical amino acid and homologous amino acid residues relative to the overlapping total amino acid residues in the optimal alignment when two amino acid sequences are aligned either with or without a gap introduced between the amino acid sequences. The identity can be obtained by using a method commonly known to those skilled in the art, sequence analysis software (a publicly known algorithm such as BLAST and FASTA), and the like. The "β-glucosidase activity" is as defined above, and this activity can be measured by, for example, adding an enzyme solution to a cellobiose substrate solution obtained by dissolving cellobiose in a 50 mM acetic acid-sodium acetate buffer (pH 5.0), allowing the reaction to proceed at 30 to 85° C. for 30 minutes, terminating the reaction by changing pH as needed, and quantitating the glucose concentration in the resulting reaction solution using a glucose quantitation kit.

In the present invention, the "glucosidase derived from a thermophile" does not encompass a glucosidase naturally having a glycosylation sequence in its amino acid sequence, and it is limited to a glucosidase that is naturally devoid of a glycosylation sequence.

A "sugar chain" as used to in the present invention has a structure in which monosaccharides are linked via a glycosidic bond, and it is terminally bonded to the amino acid side chain of the peptide sequence of the glucosidase derived from a thermophile by covalent bonding. The presence or absence of "sugar chain" can be confirmed by staining glucosidase separated by SDS electrophoresis by a generally known periodic acid-Schiff base (PAS) reaction.

Figure 7:
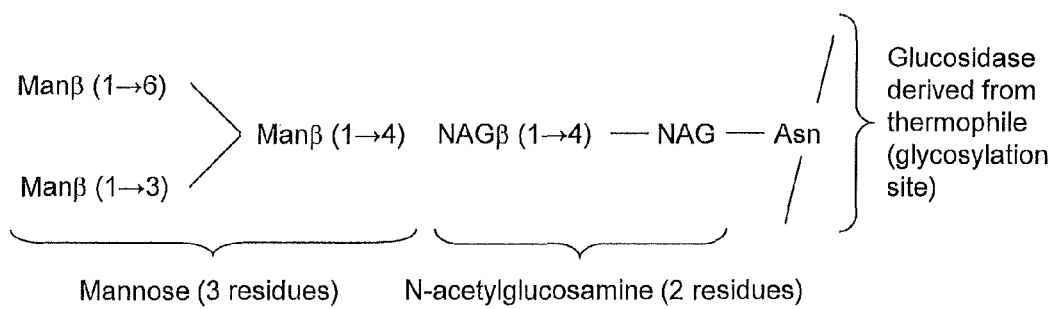
FIG. 7 is a diagram showing the basic structure of an N-linked sugar chain. In the basic structure of an N-linked sugar chain, two N-acetylglucosamine residues, and further, three mannose residues are bound to the Asn side chain of a glucosidase derived from a thermophile.
Figure 8:
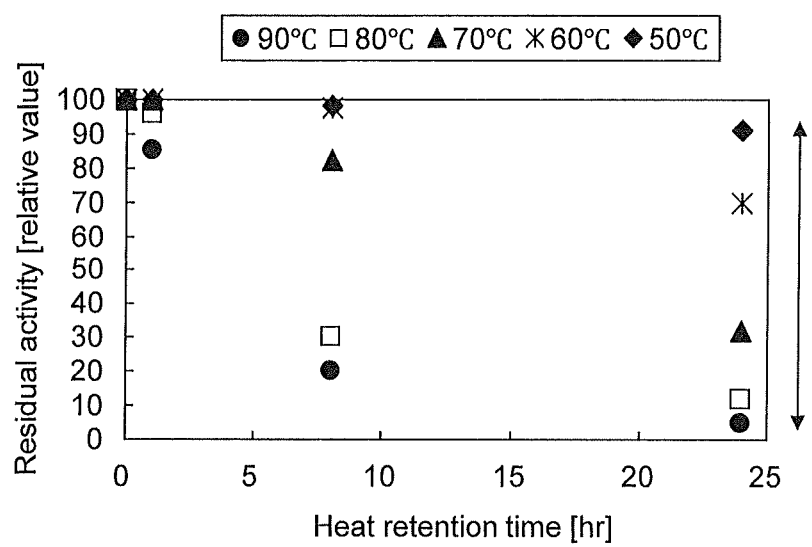
FIG. 8 is a graph showing the results of evaluation of enzyme heat stability by measuring the changes in the residual activity of AggBGY (relative value to 0 hour of heating) in cellobiose degradation at a heat retention time of 50 to 90° C. in Example 12.
Figure 9:
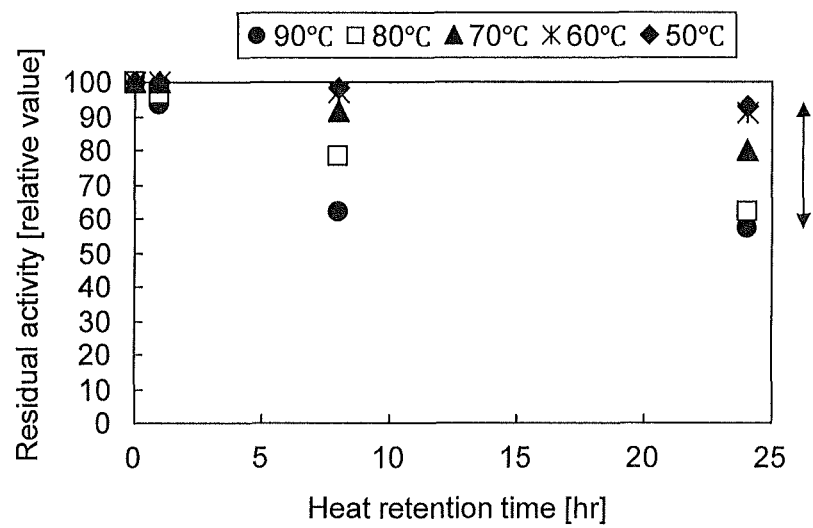
FIG. 9 is a graph showing the results of evaluation of enzyme heat stability by measuring the changes in the residual activity of the glycosylated mutant AggBGY (relative value to 0 hour of heating) in cellobiose degradation at a heat retention time of 50 to 90° C. in Example 12.
Figure 10:
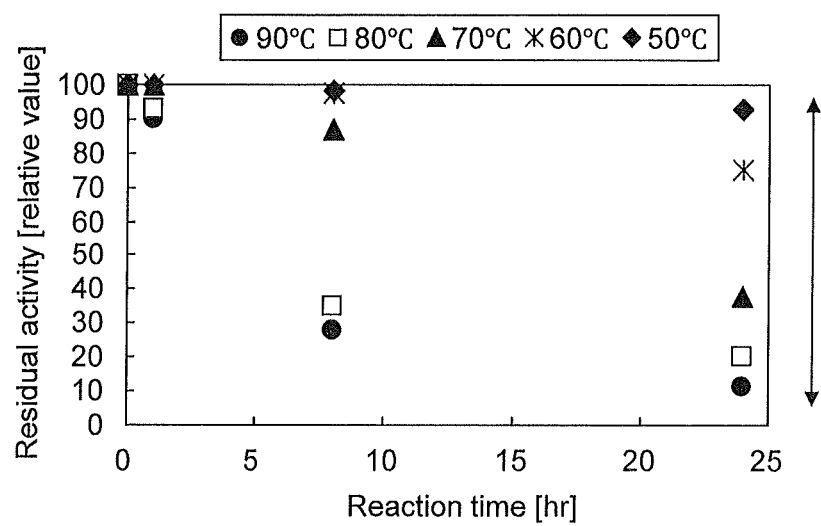
FIG. 10 is a graph showing the results of evaluation of enzyme heat stability by measuring the changes in the residual activity of CmGHFP (relative value to 0 hour of heating) in cellobiose degradation at a heat retention time of 50 to 90° C. in Example 12.
Figure 11:
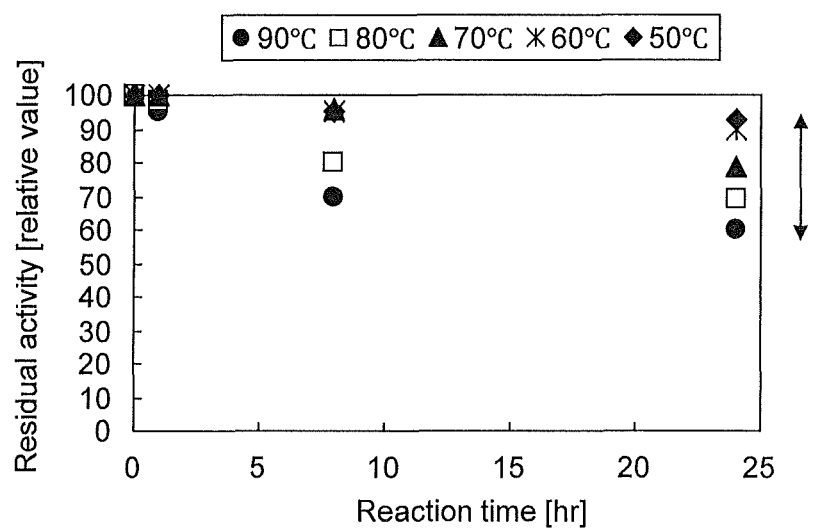
FIG. 11 is a graph showing the results of evaluation of enzyme heat stability by measuring the changes in the residual activity of the glycosylated mutant CmGHFP (relative value to 0 hour of heating) in cellobiose degradation at a heat retention time of 50 to 90° C. in Example 12.
Figure 12:
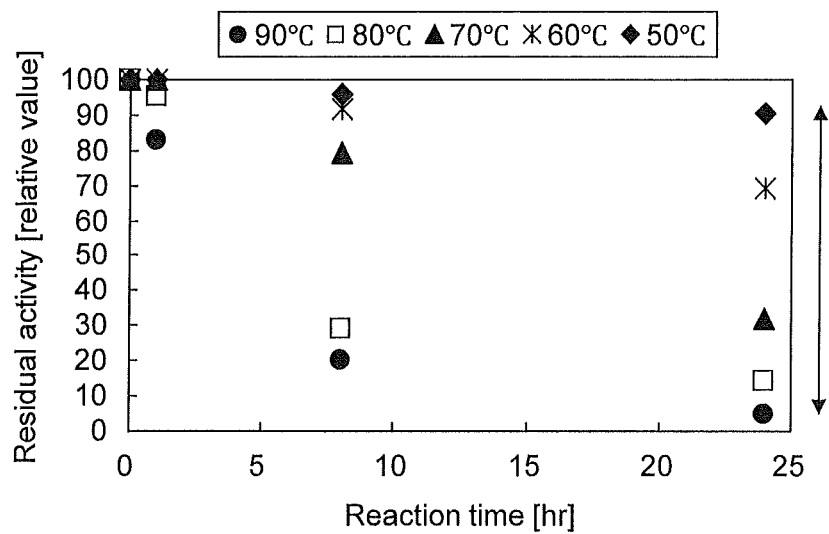
FIG. 12 is a graph showing the results of evaluation of enzyme heat stability by measuring the changes in the residual activity of SaBGAL (relative value to 0 hour of heating) in cellobiose degradation at a heat retention time of 50 to 90° C. in Example 12.
Figure 13:
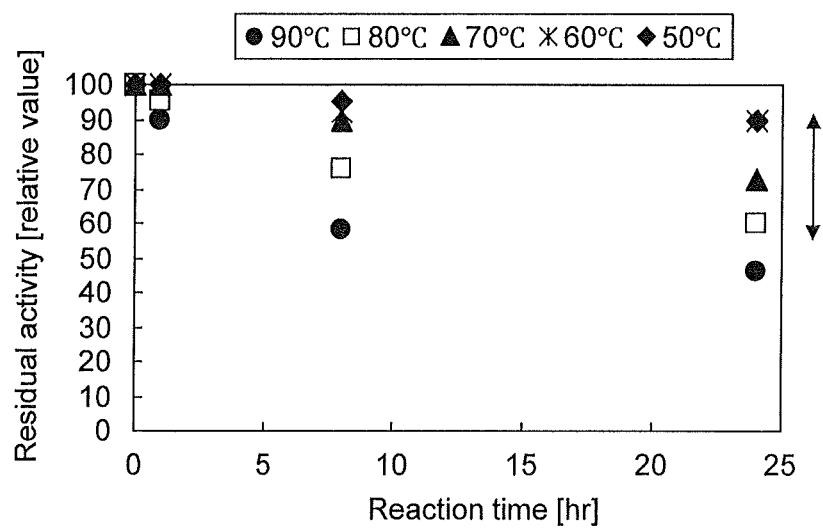
FIG. 13 is a graph showing the results of evaluation of enzyme heat stability by measuring the changes in the residual activity of the glycosylated mutant SaBGAL (relative value to 0 hour of heating) in cellobiose degradation at a heat retention time of 50 to 90° C. in Example 12.
Figure 14:
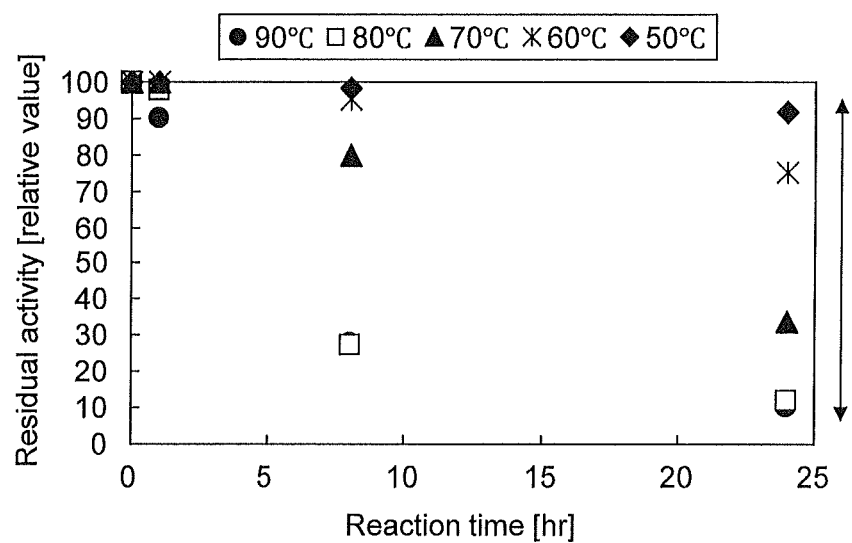
FIG. 14 is a graph showing the results of evaluation of enzyme heat stability by measuring the changes in the residual activity of SsoBGAL (relative value to 0 hour of heating) in cellobiose degradation at a heat retention time of 50 to 90° C. in Example 12.
Figure 15:
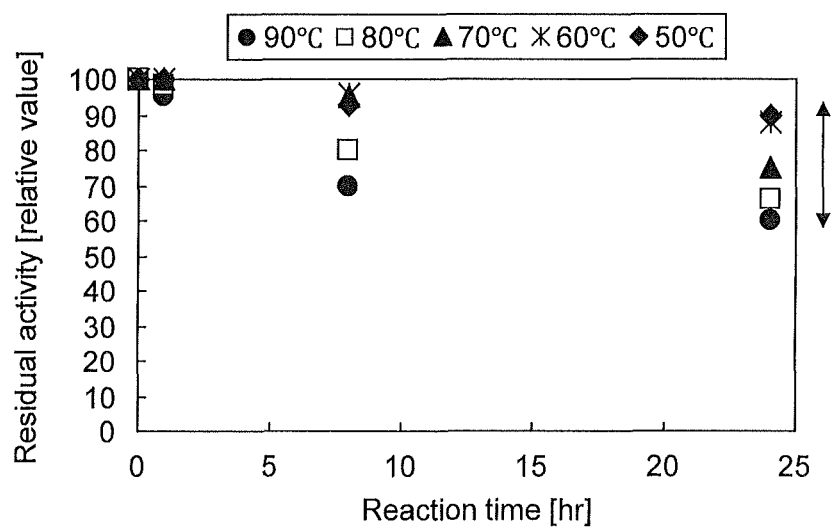
FIG. 15 is a graph showing the results of evaluation of enzyme heat stability by measuring the changes in the residual activity of the glycosylated mutant SsoBGAL (relative value to 0 hour of heating) in cellobiose degradation at a heat retention time of 50 to 90° C. in Example 12.
Figure 16:
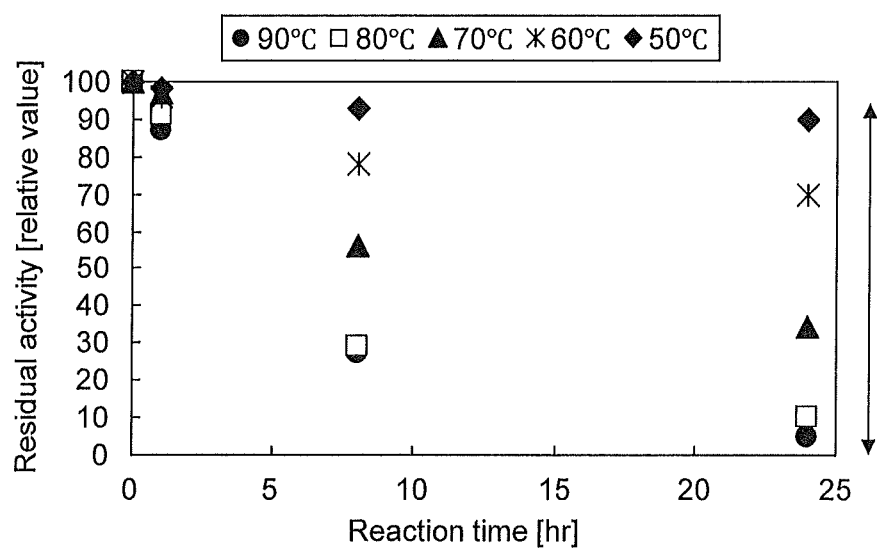
FIG. 16 is a graph showing the results of evaluation of enzyme heat stability by measuring the changes in the residual activity of PtBGAL (relative value to 0 hour of heating) in cellobiose degradation at a heat retention time of 50 to 90° C. in Example 12.
Figure 17:
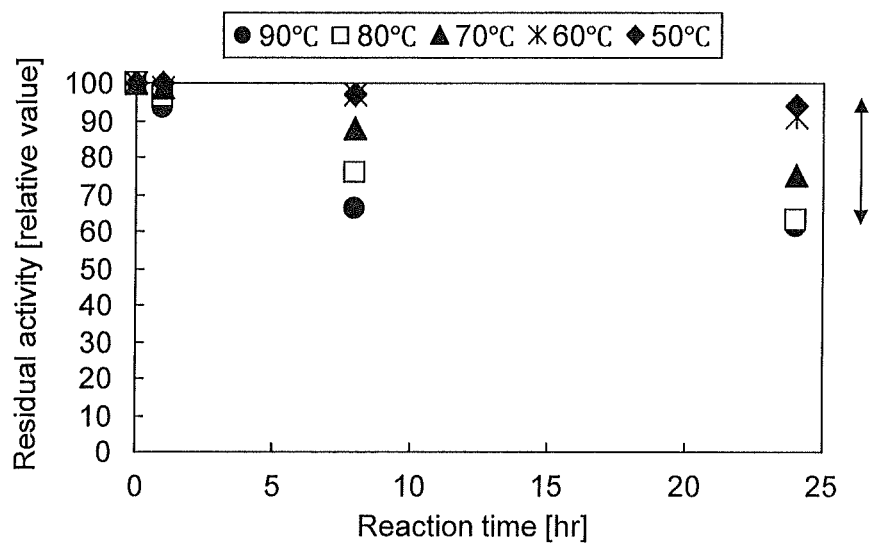
FIG. 17 is a graph showing the results of evaluation of enzyme heat stability by measuring the changes in the residual activity of the glycosylated mutant PtBGAL (relative value to 0 hour of heating) in cellobiose degradation at a heat retention time of 50 to 90° C. in Example 12.
Figure 18:
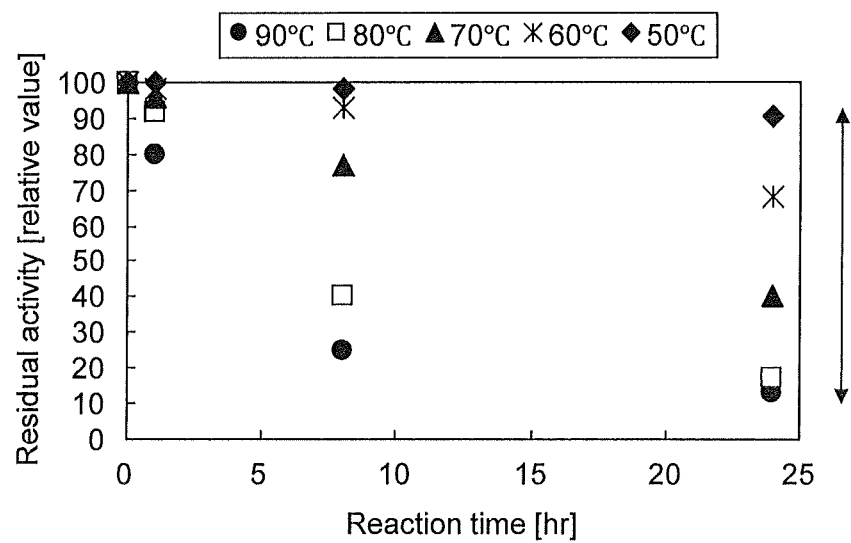
FIG. 18 is a graph showing the results of evaluation of enzyme heat stability by measuring the changes in the residual activity of TvBGAL (relative value to 0 hour of heating) in cellobiose degradation at a heat retention time of 50 to 90° C. in Example 12.
Figure 19:
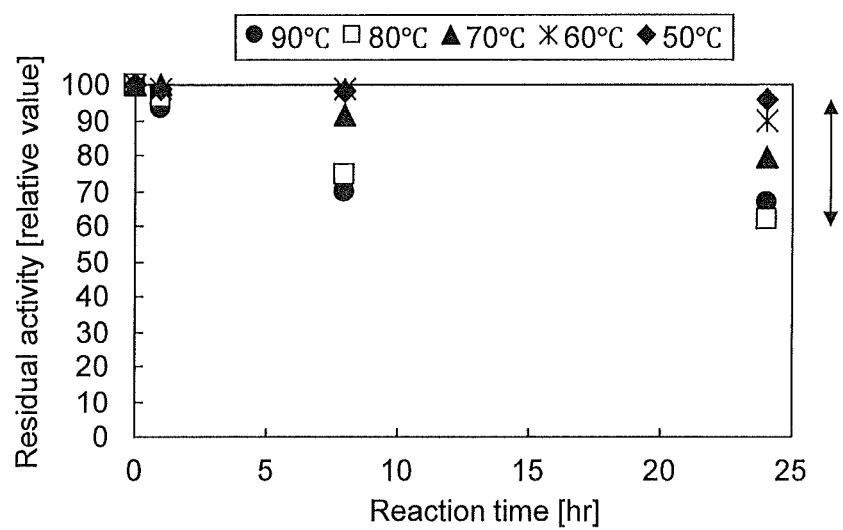
FIG. 19 is a graph showing the results of evaluation of enzyme heat stability by measuring the changes in the residual activity of the glycosylated mutant TvBGAL (relative value to 0 hour of heating) in cellobiose degradation at a heat retention time of 50 to 90° C. in Example 12.
Figure 20:
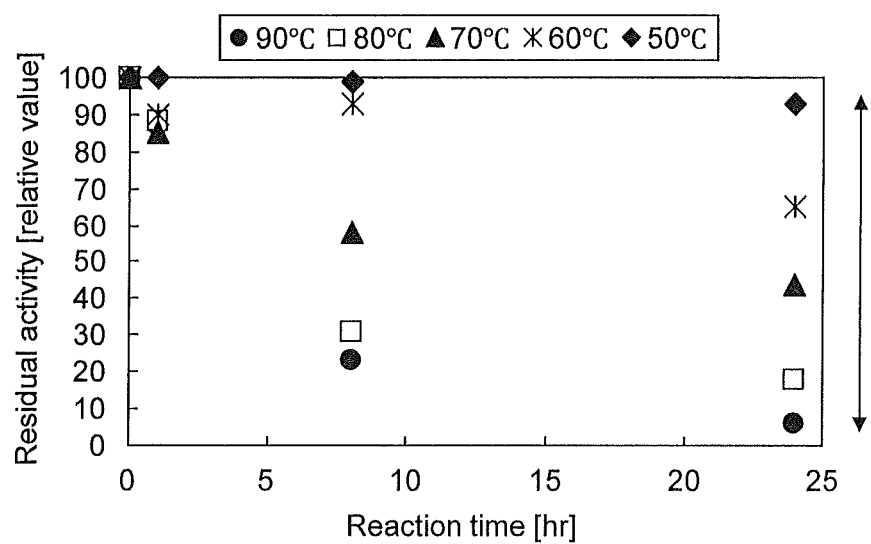
FIG. 20 is a graph showing the results of evaluation of enzyme heat stability by measuring the changes in the residual activity of FnGHFP (relative value to 0 hour of heating) in cellobiose degradation at a heat retention time of 50 to 90° C. in Example 12.
Figure 21:
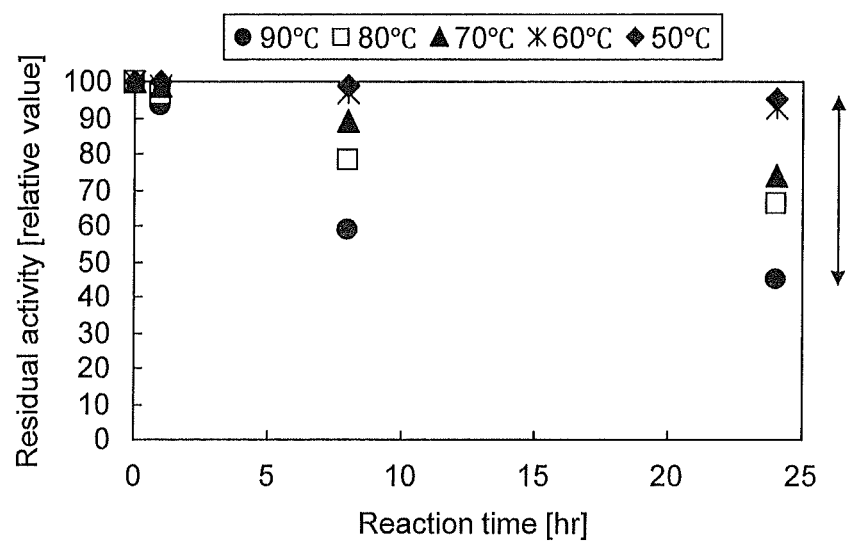
FIG. 21 is a graph showing the results of evaluation of enzyme heat stability by measuring the changes in the residual activity of the glycosylated mutant FnGHFP (relative value to 0 hour of heating) in cellobiose degradation at a heat retention time of 50 to 90° C. in Example 12.

A sugar chain is mainly classified into an N-linked sugar chain, which binds to the asparagine side chain, and an O-linked sugar chain, which binds to the serine and threonine side chains, and the sugar chain is preferably an N-linked sugar chain. For an N-linked sugar chain, a structure having a basic skeleton having two N-acetylglucosamine residues and three mannose residues with respect to the asparagine side chain is given as an example (FIG. 7). Sugar molecules are additionally bound to this basic structure by the enzymatic action, whereby various sugar chain structures are composed. The sugar chain structure varies depending on the kind of a microorganism used as a host, the culture condition of the host, and the like. The glycosylated glucosidase derived from a thermophile refers to a compound to which various sugar chain structures are attached.

Whether the sugar chain bonded to the glucosidase derived from a thermophile is either N-linked or O-linked can be confirmed by, for example, allowing each of N-linked glycanase that specifically hydrolyzes the terminal portion of an N-linked sugar chain and O-linked glycanase that specifically hydrolyzes the terminal portion of an O-linked sugar chain to act on the glucosidase, performing SDS electrophoresis, and then comparing the changes in the molecular weight of the glucosidase. As the N-linked glycanase employed here, N-glycosidase F derived from *Flavobacterium meningosepticum* (PNGaseF), endo-β-N-acetylglucosaminidase derived from *Streptomyces plicatus*, and the like can be used. Also, as the O-linked glycanase, endo-α-N-acetylgalactosaminidase derived from *Streptococcus* and the like can be used.

The sugar chain in the mutant glucosidase of the present invention is preferably a high mannose type. Here, the term "high mannose type" refers to an N-linked sugar chain in which four or more mannose residues are linked per two N-acetylglucosamine residues or glucosamine residues that compose the sugar chain. As the sugar other than mannose, other monosaccharides such as glucose may be contained. When glucose is contained, it is normally bound to the non-reducing end of mannose of a high mannose type sugar chain.

Examples of an N-linked sugar chain other than a high mannose type include a complex type sugar chain. A complex type is characterized by containing, as a sugar other than mannose and N-acetylglucosamine, various kinds of sugars such as fructose and sialic acid as its components. Compared to a high mannose type, the ratio of N-acetylglucosamine in a sugar chain is increased, and the ratio of mannose to two N-acetylglucosamine residues is three or less.

Whether or not a given N-linked sugar chain is a high mannose type or a hybrid type can be confirmed by, for example, transferring glucosidase having been subjected to electrophoresis to a PVDF membrane, reacting it with sugar chain-specific lectin, and examining the color development. Examples of the sugar chain-specific lectin used here include Concanavalin A (ConA), lectin from *Ricinus communis* (RCA12), lectin from *Ulex europaeus* (UEA-1), and peanut lectin (PNA). If the glucosidase is stained with ConA, it can be confirmed as a high mannose type N-linked sugar chain, while if it is stained with RCA120, it can be confirmed as a hybrid type N-linked sugar chain. Also, as another judgment technique, the sugar chain structure can be confirmed by separating the sugar chain-composing sugar from sufficiently purified glucosidase and quantitating the monosaccharide component of the sugar thus separated by analyzing it with MALDI-TOF/MS or HPLC.

The "glycosylation sequence" refers to the amino acid sequence of the part that is subjected to glycosylation in the process of expression and translation in a eukaryotic organism.

Examples of the glycosylation sequence include the consensus sequence of an N-linked sugar chain, which is Asn-X-Ser or Asn-X-Thr (wherein, X is any amino acid except proline), and the consensus sequence of an O-linked sugar chain, which is Cys-X-Ser-X-Pro-Cys (wherein, X is any amino acid except proline) (SEQ ID NO: 63); however, the glycosylation sequence is not limited thereto. Preferably, the glycosylation sequence is the consensus sequence of an N-linked sugar chain. Here, examples of amino acid except proline include Gly, Ala, Val, Leu, Ile, Phe, Tyr, Trp, Met, Cys, Ser, Thr, Asp, Glu, His, Lys, Arg, Asn, and Gln.

The glycosylated mutant glucosidase derived from a thermophile according to the present invention (hereinbelow, referred to as a "mutant glucosidase") refers to a mutant glucosidase resulting from introduction of the amino acid sequence composing the aforementioned glycosylation sequence into the aforementioned amino acid sequence of a glucosidase derived from a thermophile, wherein the amino acid sequence is selectively glycosylated. One or two or more glycosylation sequences may be introduced, and these sequences may be all the same or contain multiple kinds of glycosylation sequences.

As the glycosylation sequence-introduction site, such a position that does not inactivate the original enzyme activity by the introduction is preferably selected. The method for determining such a glycosylation sequence-introduction site can be carried out by the following step 1) and step 2).

Step 1) Perform the amino acid sequence alignment analysis between a glucosidase derived from filamentous fungi naturally possessing a glycosylation sequence and a glucosidase derived from a thermophile that is naturally devoid of a glycosylation sequence to clarify a relative positional relationship of the glycosylation sequence of the glucosidase derived from filamentous fungi in the glucosidase derived from a thermophile to specify the glycosylation sequence-introduction site. As the alignment tool, a plenty of well-known software such as ClustalW can be used. The glucosidase derived from filamentous fungi naturally possessing a glycosylation sequence is preferably a glucosidase derived from the genus *Trichoderma* or a glucosidase derived from the genus *Aspergillosis*. The amino acid sequences of these glucosidases derived from filamentous fungi are publicly known, and preferably, a β-glucosidase derived from *Trichoderma reesei* having the amino acid sequence of SEQ ID NO: 1 or a β-glucosidase derived from *Aspergillus niger* having the amino acid sequence of SEQ ID NO: 2 is used.

Step 2) Next, confirm if the glycosylation sequence-introduction site in the glucosidase derived from a thermophile that has been specified by the aforementioned alignment analysis is present on the surface of the enzyme. Whether or not it is present on the surface of the enzyme can be found out by using the crystal structure of the objective glucosidase derived from a thermophile. Such a crystal structure can be retrieved from a database such as Protein Data Bank if it is known. Also, a crystal structure may be obtained by actually performing X-ray crystallography, etc.

In the present invention, the glycosylation sequence-introduction site is preferably selected in accordance with the aforementioned step 1) and step 2); however, as another technique, it can be selected in accordance with the following step 3) and step 4).

Step 3) Obtain the Accessible Surface Area (ASA) (Å$^2$) of the amino acid residue by analytical software, and based on the value thus obtained, select the amino acid residue that is exposed near the surface of the glucosidase derived from a thermophile. The ASA of each amino acid residue can be calculated using ASA analytical software such as AREAIMOL (ccp4 package) (Collaborative Computing Project Number 4 (CCP4) of UK Science and Engineering Research Council), SURFace (Barry Honig's group, the Department of Biochemistry and Molecular Biophysics and Center of Computational Biology and Bioinformatics of Columbia), and ASAP (Institute for Molecular Bioscience, University of Queensland and the ARC Centre in Bioinformatics), all of which are obtainable from websites. If an amino acid residue is calculated as having an ASA of 1 Å$^2$ or greater, then it is assumed to be exposed to the surface, and as the glycosylation sequence-introduction site, an amino acid residue with an ASA of 2 Å$^2$ or greater is preferably selected. Particularly, in order to introduce the three amino acid residues (Asn-X-Ser or Asn-X-Thr: X is any amino acid except proline), which form the consensus sequence for an N-linked sugar chain, it is preferable to select a part containing three or more consecutive amino acids with an ASA of 2 Å$^2$ or greater.

Step 4) Select, from among the glycosylation sequence-introduction sites in a glucosidase derived from a thermophile selected by the step 3) above, a position that is too far from the enzyme active site of the glucosidase derived from a thermophile to cause a reduction in the enzyme activity by introduction of the glycosylation sequence. The distance from the enzyme active site can be found out by using the crystal structure of the objective glucosidase derived from a thermophile in a similar manner to the above. Specifically, after excluding the amino acid residues within a distance of 3.5 Å from the enzyme active site, the amino acid residue that is further apart than this distance is preferably selected.

For example, application of the aforementioned step 3) and step 4) to PfuBGL represented by the amino acid sequence of SEQ ID NO: 4 will be as follows. First of all, using AREAIMOL (ccp4 package), ASA is calculated by assuming that the solvent molecule has 1.4 Å, and the amino acid residue with an ASA of 2 Å$^2$ or greater is extracted (Table 1 (i)). Subsequently, a part containing three or more consecutive amino acids with an ASA of 2 Å$^2$ or greater is extracted (Table 1 (ii)). Further, based on the information of the crystal structure of PfuBGL, the amino acid residues within a distance of 3.5 Å from the enzyme active site are specified (23 residues of S13, R78, N207, I263, I303, G304, V305, N306, Y307, S343, D344, L367, I370, I371, T372, D378, R384, Y387, H391, D404, V405, R406, N407, Y408, L409, H410, W411, and F427) and then excluded. As a result, the glycosylation sequence-introduction site can be selected (Table 1 (iii)).

TABLE 1

Example of selection of the glycosylation sequence-introduction site in PfuBGL (i) Amino acid residues with an ASA of 2 Å$^2$ or greater M1-M9, F17-F19, G22-G25, E27-V34, H37-E40, I42-L51, E53, N54, Y58-Q64, D67, I68, E70, I68, E70, K71, G73, D75, E82-R85, P88-P90, TABLE 1-continued Example of selection of the glycosylation sequence-introduction site in PfuBGL F92-D110, P112-115, K117, E118, E120-A127, E129, H130, R132, K133, S136, D137, K139-F145, Y150-W152, P155-D160, I162, A163, R165-L167, P169-P173, W176-T181, V183, E184, K187, Y194, H195, D197-L199, D201, M202, E208, N210-Q215, Y217-S222, F224, P225, G227-K236, K238-N240, I242, I246, Y249, D250, K253-S259, A265-E279, E281-D287, E289, T292, I293, H295-W302, Y308, R310-Y313, A315-Y326, F328-R340, D344, F345, W374, Y350-E352, E355, N356, K359, Y360, N362-P368, I370, E373, M376, A379-Y383, P385-Y387, S390, K363, A394, Y396, N397, M399-R406, W411, E418-Q421, F423-F427, Y431, D433, P443, L446, R449, E450, T453-E460, A462-K473

(ii) Among (i), a part containing three or more consecutive amino acid residues

M1-M9, F17-F19, G22-G25, E27-V34, H37-E40, I42-L51, Y58-Q64, E82-R85, P88-P90, F92-D110, P112-115, E120-A127, K139-F145, Y150-W152, P155-D160, R165-L167, P169-P173, W176-T181, D197-L199, N210-Q215, Y217-S222, G227-K236, K238-N240, K253-S259, A265-E279, E281-D287, H295-W302, R310-Y313, A315-Y326, F328-R340, Y350-E352, N362-P368, A379-Y383, P385-Y387, M399-R406, E418-Q421, F423-F427, T453-E460, A462-K473

(iii) Among (ii), an amino acid residue away from the enzyme active site by 3.5 Å or more M1-M9, F17-F19, G22-G25, E27-V34, H37-E40, I42-L51, Y58-Q64, E82-R85, P88-P90, F92-D110, P112-115, E120-A127, K139-F145, Y150-W152, P155-D160, R165-L167, P169-P173, W176-T181, D197-L199, N210-Q215, Y217-S222, G227-K236, K238-N240, K253-S259, A265-E279, E281-D287, H295-W302, R310-Y313, A315-Y326, F328-R340, Y350-E352, N362-E366, A379-Y383, M399-A403, E418-Q421, F423-R426, T453-E460, A462-K473

The glycosylation sequence-introduction site is present at one site or preferably at two to five sites.

In the present invention, the term "introduction" indicates that the aforementioned glycosylation sequence is translated into a polypeptide. That is, in the original amino acid sequence of a glucosidase derived from a thermophile, the aforementioned glycosylation sequence may substitute for the existing amino acid sequence, or it may be inserted into the existing amino acid sequence. That is, in the case of substitution, the length of polypeptide remains unchanged relative to before mutation, while in the case of insertion, the length of polypeptide becomes longer by the length of the inserted glycosylation sequence. However, from the viewpoint of retention of the enzyme activity, the introduction of the glycosylation sequence preferably takes place by substitution of the existing amino acid sequence.

Also, as the glycosylation sequence to be introduced, any of the aforementioned glycosylation sequences may be adopted, and as X, any amino acid except proline can be used; however, a glycosylation sequence and an amino acid that are expected to bring little impact when introduced as a mutation should be selected. For example, in the case of an amino acid substitution, a conservative amino acid substitution is desirable. The conservative amino acid substitution refers to substitution that takes place between the amino acids having similar electrical properties, structural properties, polarity or hydrophobicity, etc., and the substitution between these similar amino acids is expected not to alter the phenotype of protein. Examples include a basic amino acid (Lys, Arg, and His), an acidic amino acid (Glu and Asp), an aromatic amino acid (Trp, Phe, Tyr, and His), a branched amino acid (Val, Ile, and Thr), a polar amino acid (Ser, Thr, Tyr, Cys, Met, Gln, Asn, and Gly), and a hydrophobic amino acid (Ala, Val, Leu, and Ile).

In one embodiment, using the aforementioned technique, the glycosylation sequence-introduction site in the amino acid sequence (SEQ ID NO: 4) of the β-glucosidase derived from *Pyrococcus furiosus* can be specified as H60-L61-Y62 (FIG. 1).

Also, according to the present invention, using the amino acid sequence of the glucosidase derived from a thermophile in which the glycosylation sequence-introduction site is determined in the aforementioned technique, the glycosylation sequence-introduction site can be determined also in another glucosidase derived from a thermophile having the amino acid sequence that is highly identical to the above amino acid sequence. For example, after determining the glycosylation sequence-introduction site in the β-glucosidase derived from *Pyrococcus furiosus* shown in SEQ ID NO: 4 by the aforementioned technique, an alignment analysis is performed with respect to another enzyme having the amino acid sequence having high identity with the β-glucosidase shown in the SEQ ID NO: 4, and the position in the amino acid sequence of this enzyme that corresponds to the determined introduction site in SEQ ID NO: 4 (for example, H60-L61-Y62) can be determined as the glycosylation sequence-introduction site. Examples of another enzyme having the amino acid sequence having high identity with the β-glucosidase shown in the SEQ ID NO: 4 include the enzymes having the amino sequences shown in SEQ ID NO: 8, SEQ ID NO: 10, SEQ ID NO: 12, SEQ ID NO: 14, SEQ ID NO: 16, SEQ ID NO: 18, and SEQ ID NO: 20.

In one embodiment, using the aforementioned technique, the glycosylation sequence-introduction site in the amino acid sequences shown in SEQ ID NO: 8, SEQ ID NO: 10, SEQ ID NO: 12, SEQ ID NO: 14, SEQ ID NO: 16, SEQ ID NO: 18, and SEQ ID NO: 20 can be specified as N60-L61-N62, D60-L61-Y62, G61-N62-Y63, G61-N62-Y63, D58-L59-Y60, N63-N64-Y65, and K63-Q64-Y65, respectively (FIG. 2-1 and FIG. 2-2).

In one embodiment, the mutant glucosidase according to the present invention comprises, for example, the amino acid sequence shown in SEQ ID NO: 6. Preferably, the mutant glucosidase according to the present invention consists of, for example, the amino acid sequence shown in SEQ ID NO: 6.

In the present invention, the glucosidase activity refers to the cellobiose degradation activity. That is, it is an activity of catalyzing the reaction for producing glucose by hydrolysis of cellobiose, when it is used as a substrate. The mutant glucosidase of the present invention retains preferably 40% or more, more preferably 50% or more, even more preferably 60% or more, and particularly preferably 70% or more activity relative to the cellobiose degradation activity of the wild-type glucosidase. The cellobiose degradation activity of the mutant glucosidase of the present invention relative to the wild-type can be evaluated by, for example, adding the mutant glucosidase or the wild-type glucosidase to a 10 mM cellobiose/50 mM acetate buffer solution, carrying out the enzymatic reaction at 50° C., and then measuring the amount of glucose produced. Here, the amount of glucose produced can be quantitated in accordance with a publicly known technique such as the enzymic method and HPLC.

The mutant glucosidase according to the present invention may be one obtained by any method; however, in order for the introduced glycosylation sequence to be selectively glycosylated, the mutant glucosidase is desirably provided by culturing a eukaryotic cell containing DNA encoding the mutant glucosidase.

DNA encoding the mutant glucosidase can be produced by the following method. That is, it can be produced by determining the glycosylation sequence-introduction site in the amino acid sequence of a glucosidase derived from a thermophile by the aforementioned technique, and then introducing DNA encoding the glycosylation sequence into the part of the nucleotide sequence in DNA encoding the glucosidase that corresponds to the introduction site. Here, the term "DNA" encompasses any nucleic acid that encodes the glucosidase or the glycosylation sequence, which can be cDNA, genomic DNA, a gene, and the like.

Examples of DNA encoding a glucosidase derived from a thermophile include DNA encoding the aforementioned glucosidase derived from a thermophile, for example, DNA comprising the nucleotide sequence shown in SEQ ID NOs: 3, 7, 9, 11, 13, 15, 17, and 19, preferably DNA consisting of the above nucleotide sequences. Also, DNA encoding a glucosidase derived from a thermophile encompasses DNA comprising a nucleotide sequence capable of hybridizing with DNA consisting of a nucleotide sequence complementary to the nucleotide sequence shown in SEQ ID NOs: 3, 7, 9, 11, 13, 15, 17, and 19 under stringent conditions, preferably DNA consisting of the above nucleotide sequence, and encoding a protein having the β-glucosidase activity. The stringent condition may be a low stringent condition, a medium stringent condition, or a high stringent condition. The stringent condition includes, for example, carrying out hybridization in 2 to 5×SSC and 0.2% SDS (wherein, 1×SSC indicates 150 mM sodium chloride, 15 mM sodium citrate, and pH 7.0) at 45 to 70° C., followed by washing with 0.1 to 1×SSC and 0.1 to 0.2% SDS at 45 to 65° C. The stringent condition is described in, for example, Sambrook et al., Molecular Cloning, A Laboratory Manual, 2nd edition, 1989, Cold Spring Harbor Laboratory Press. Further, DNA encoding a glucosidase derived from a thermophile encompasses DNA comprising the nucleotide sequence shown in SEQ ID NOs: 3, 7, 9, 11, 13, 15, 17 and 19 that has been subjected to one or multiple deletion, substitution, addition, or insertion, or deletion, substitution, addition, or insertion of one or a plurality of nucleotides and encoding a protein having the β-glucosidase activity. Here, the range of "one or a plurality" is not particularly limited; however, it is preferably 10 or less, more preferably five or less, particularly preferably four or less, or one or two. Furthermore, DNA encoding a glucosidase derived from a thermophile encompasses DNA comprising a nucleotide sequence having 85% or more, more preferably 90% or more, and most preferably 95% or more identity with the nucleotide sequence shown in SEQ ID NOs: 3, 7, 9, 11, 13, 15, 17, and 19 according to calculation using BLAST and the like (for example, default parameter(s), i.e., the initially set parameter(s)), preferably DNA consisting of the above nucleotide sequence, and encoding a protein having the β-glucosidase activity.

Examples of DNA encoding the glycosylation sequence include DNA encoding the aforementioned glycosylation sequence, and it can be appropriately determined in consideration of the host organisms and the degeneracy of the genetic code.

DNA encoding the glycosylation sequence can be introduced into DNA encoding a glucosidase by a publicly known technique such as site-directed mutagenesis and specific mutation introduction by PCR (Sambrook et al., described above).

In one embodiment, examples of DNA encoding the mutant glucosidase include DNA comprising the nucleotide sequence shown in SEQ ID NO: 5. Preferably, examples of DNA encoding the mutant glucosidase include DNA consisting of the nucleotide sequence shown in SEQ ID NO: 5. In SEQ ID NO: 5, DNA encoding the glycosylation sequence is introduced as -aaccgcact- in the positions 178 to 186.

Further, DNA encoding a secretion signal sequence that is suitable for the host may be added to DNA encoding the aforementioned mutant glucosidase. The secretion signal sequence can be appropriately added to the 5' terminus or 3' terminus of DNA encoding the mutant glucosidase, and preferably, it is added to the 5' terminus. DNA encoding the secretion signal sequence may also be incorporated in an expression vector in advance. For example, when the host is yeast, the α factor signal sequence, the α-amylase signal sequence, the glucoamylase signal sequence, the serum albumin signal sequence, the inulinase-derived signal sequence, the invertase signal sequence, the killer protein signal sequence, the lysozyme signal sequence, and the like are used. Particularly in *Pichia pastoris*, the α factor secretion signal sequence is preferred. The α factor secretion signal sequence is publicly known, and for example, it is registered at GenBank under NP_015137, which can be used in the present invention.

When the genus *Trichoderma* is used as the host, the cellulase-related signal sequence can be used. The genus *Trichoderma* has a characteristic of secreting, as cellulase, cellobiohydrolase, xylanase, endoglucanase, xylosidase, and xyloglucanase outside the cell, and these enzymes each have a secretion signal sequence. These signal sequences are publicly known, and peptide sequences containing these signal sequences can be used by functionally linking them to the mutant glucosidase.

DNA encoding the mutant glucosidase having one or more glycosylation sequences that can be subjected to glycosylation by a eukaryotic cell prepared as above is linked to the downstream of the promoter in an appropriate expression vector using a restriction enzyme and a DNA ligase, whereby an expression vector carrying the DNA can be produced.

Examples of the expression vector include a bacterial plasmid, a yeast plasmid, DNA of a phage (such as lambda phage), DNA of a virus such as a retrovirus, a baculovirus, a vaccinia virus, and an adenovirus, a derivative of SV40, and an *agrobacterium* as a vector for a plant cell, and any other vector can be used as long as it is replicable and viable, and glycosylation is feasible in the host cell. Examples of the expression vector include, when the host is yeast, pPink-HC, pPink-LC, pPinkα-HC, pPCIZ, pPCIZα, pPCI6, pPCI6α, pFLD1, pFLD1α, pGAPZ, pGAPZα, pPIC9K, and pPIC9.

As the promoter, any promoter may be used as long as it is a suitable promoter corresponding to the host to be used for gene expression, and it may be either a constitutive promoter or an inducible promoter. Examples of the promoter include, when the host is yeast, the AOX1 promoter, the TEF1 promoter, the ADE2 promoter, the CYC1 promoter, the GAL-L1 promoter, the AOX2 promoter, the YPT1 promoter, the GAP promoter, and the FLD promoter.

The host cell to be used in the present invention may be any host cell as long as it has the glycosylation mechanism. Preferred examples of the host cell include a yeast cell, a fungal cell, an insect cell, a plant cell, and an animal cell. Examples of the yeast cell include the genus *Pichia*, the genus *Saccharomyces*, and the genus *Schizosaccharomyces*. Examples of the fungal cell include the genus *Aspergillus* and the genus *Trichoderma*. Examples of the insect cell include Sf9. Examples of the plant cell include the dicotyledons. Examples of the animal cell include CHO, HeLa, and HEK293. More preferably, the host cell is a yeast cell, and even more preferably, it is *Pichia pastoris*.

Transformation or transfection can be carried out by a publicly known method such as the calcium phosphate method and electroporation. The mutant glucosidase can be obtained by expressing it in the host cell that has been transformed or transfected as described above under the control of the promoter, and then collecting the expression product. For expression of the mutant glucosidase, the host cell is allowed to proliferate or grow to an appropriate cell density, and the promoter is induced by a temperature shift or chemical induction means such as the addition of isopropyl-1-thio-β-D-galactoside (IPTG), and then the cell is further cultured for a certain period of time.

When the mutant glucosidase is excreted out of the cell, it is directly purified from the medium. When the mutant glucosidase is present outside the cell, the cell is disrupted by physical means such as ultrasonic disintegration and mechanical disintegration or by chemical means such as a cell lysis agent, and then the mutant glucosidase is purified. The mutant glucosidase can be partially or completely purified from the medium of the recombinant cell by a combination of techniques such as ammonium sulfate precipitation or ethanol precipitation, acid extraction, anion or cation exchange chromatography, reverse-phase high-performance chromatography, affinity chromatography, gel filtration chromatography, and electrophoresis.

In the hydrolysis of cellulosic biomass, the glycosylated mutant glucosidase of the present invention has higher heat resistance and can achieve a cellulose degradation efficiency that is 1.2 times, 1.3 time, 1.4 times, 1.5 times, 1.6 times, 1.7 times, 1.8 times, 1.9 times, and twice or more as high as the cellulose degradation efficiency achieved when a glucosidase derived from a thermophile is used with an unglycosylated cellulase mixture. The mutant glucosidase of the present invention can be applied to cellulosic biomass such as cellulosic biomass containing a lignin component, Avicel containing almost no lignin component, Solka Floc, and industrial pulp, and it can achieve profound cellulose degradation efficiency particularly in cellulosic biomass containing a lignin component.

The mutant glucosidase obtained as above can be used as an enzyme composition for saccharification of biomass by mixing with cellulase. The "cellulose" as used herein is not particularly limited as long as it is an enzyme having a cellulose degradation activity, and it may be a mixture of one or more kinds of cellulases. Examples of such an enzyme include cellulase, hemicellulase, cellobiohydrolase, endoglucanase, exoglucanase, xylanase, and mannanase.

The cellulase used in the present invention is preferably a mixture of cellulases derived from filamentous fungi. The mixture of cellulases derived from filamentous fungi is a mixture containing at least both endoglucanase and cellobiohydrolase. In order to carry out more efficient saccharification of cellulose, a mixture of cellulases derived from filamentous fungi containing two or more kinds of endoglucanases and/or two or more kinds of cellobiohydrolases is preferred. Examples of the microorganism producing the aforementioned mixture of cellulases derived from filamentous fungi include the genus *Trichoderma*, the genus *Aspergillus*, the genus *Cellulomonas*, the genus *Clostridium*, the genus *Streptomyces*, the genus *Humicola*, the genus *Acremonium*, the genus *Irpex*, the genus *Mucor*, and the genus *Talaromyces*. Because these microorganisms produce a cellulase in the liquid culture medium, the liquid culture medium may be directly used as an unpurified mixture of cellulases derived from filamentous fungi, or a preparation obtained from a purified product of the liquid culture medium may be used as the mixture of cellulases derived from filamentous fungi. The mixture of cellulases derived from filamentous fungi may simultaneously contain a β-glucosidase produced by the microorganism; however, considering that it does not exist in an adequate amount for cellulose degradation, and also, it is clearly distinguishable from the β-glucosidase derived from the genus *Pyrococcus* as will be described later, the β-glucosidase produced by the cellulase-producing microorganism is also encompassed by cellulase in the present invention. When a preparation obtained from a purified product of the aforementioned liquid culture medium is used, a substance other than an enzyme such as a protease inhibitor, a dispersant, a solubilizing agent, and a stabilizer can be added and the resulting product may be used as a cellulase preparation.

The mixture of cellulases derived from filamentous fungi used in the present invention is preferably a mixture of cellulases produced by the genus *Trichoderma*. The genus *Trichoderma* produces a mixture of cellulases containing at least two kinds of endoglucanases and at least two kinds of cellobiohydrolases into the liquid culture medium, and a mixture of cellulases prepared from such a liquid culture medium is preferably used in the present invention. Among the organisms belonging to the genus *Trichoderma*, a mixture of cellulases derived from *Trichoderma reesei* is more preferred. Examples of the mixture of cellulases derived from *Trichoderma reesei* include a mixture of cellulases derived from *Trichoderma reesei* QM9414, *Trichoderma reesei* QM9123, *Trichoderma reesei* RutC-30, *Trichoderma reesei* PC3-7, *Trichoderma reesei* ATCC66589, *Trichoderma reesei* CL-847, *Trichoderma reesei* MCG77, *Trichoderma reesei* MCG80, and *Trichoderma viride* QM9123. Also, a mutant strain derived from the aforementioned genus *Trichoderma* that has achieved improved cellulose productivity through mutagenic treatment using a mutagen, ultraviolet ray irradiation, or the like may also be used.

The mixture of cellulases derived from the genus *Trichoderma* used in the present invention is an enzyme composition containing a plurality of enzyme components such as cellobiohydrolase, endoglucanase, exoglucanase, β-glucosidase, xylanase, and xylosidase. The mixture of cellulases derived from the genus *Trichoderma* can carry out effective hydrolysis of cellulose owing to the concerted effect or the complementary effect of a plurality of enzyme components in cellulose hydrolysis.

Cellobiohydrolase is a generic term for cellulase that is characterized by starting hydrolysis from the terminal portion of cellulose, and a group of enzymes belonging to cellobiohydrolase is listed under EC No: EC3.2.1.91.

Endoglucanase is a generic term for cellulase that is characterized by starting hydrolysis from the middle part of the cellulose molecular chain, and a group of enzymes belonging to endoglucanase is listed under EC NOs: EC3.2.1.4, EC3.2.1.6, EC3.2.1.39, and EC3.2.1.73.

Exoglucanase is a generic term for cellulase that is characterized by starting hydrolysis from the terminus of the cellulose molecular chain, and a group of enzymes belonging to exoglucanase is listed under EC NOs: EC3.2.1.74 and EC3.2.1.58.

β-glucosidase is a generic term for cellulase that is characterized by acting on cellooligosaccharides or cellobiose, and a group of enzymes belonging to β-glucosidase is listed under EC No: EC3.2.1.21.

Xylanase is a generic term for cellulase that is characterized by acting on hemicellulose or, particularly, xylan, and a group of enzymes belonging to xylanase is listed under EC No: EC3.2.1.8.

Xylosidase is a generic term for cellulase that is characterized by acting on xylooligosaccharides, and a group of enzymes belonging to xylosidase is listed under EC No: EC3.2.1.37.

In the present invention, cellulose-containing biomass is used as a substrate of the enzymatic reaction. Cellulose-containing biomass is cellulose that is widely derived from plant biomass. More specifically, cellulose-containing biomass is bagasse, corn stover, corncob, switchgrass, rice straw, wheat straw, trees, wood materials, building material waste, newspaper, used paper, pulp, and the like. Although the above cellulose-containing biomass contains an impurity such as the macromolecular aromatic compound lignin and hemicellulose, cellulose-containing biomass in which lignin and hemicellulose are partially degraded by using an acid, an alkali, pressurized hot water, and the like as pre-treatment may also be used as cellulose. Here, pre-treated cellulose-containing biomass as described above is provided as "lignocellulose", which can be used as a substrate of the enzymatic reaction.

As the cellulose-containing biomass used in the present invention, one that has been subjected to pre-treatment such as ammonia treatment, diluted sulfuric acid treatment, and hydrothermal treatment by a publicly known technique can be used.

For ammonia treatment, the methods described in JP Patent Publication (Kokai) No. 2008-161125 A and JP Patent Publication (Kokai) No. 2008-535664 A can be applied. Specifically, to biomass, ammonia is added at a concentration of 0.1 to 15 wt. %, and treatment is carried out at 4 to 200° C., preferably at 90 to 150° C. Ammonia to be added may be either in the liquid state or in the gaseous state. When ammonia is in the liquid state, either liquid ammonia or an aqueous solution of ammonia may be used. The number of treatment is not particularly limited, and it may be performed at least once. When the treatment is performed twice or more, the first treatment and the second treatment may be performed under different conditions. The product obtained by the ammonia treatment needs to be subjected to neutralization of ammonia or removal of ammonia before performing the hydrolysis reaction. Neutralization may be performed on a liquid that still contains a solid content or a liquid fraction from which the solid content has been separated. An acid reagent used for neutralization is not particularly limited. Ammonia can also be removed by volatilization in the gaseous state by keeping the ammonia-treated product under the reduced pressure condition. In that case, ammonia that has been removed may be recovered and recycled.

The hydrothermal treatment may be performed by, for example, adding water so that the cellulose-containing biomass is 0.1 to 50 wt. %, and treating the resulting solution at a temperature of 100 to 400° C. for one second to 60 minutes. The number of treatment is not particularly limited, and it may be performed at least once. When the treatment is performed twice or more, the first treatment and the second treatment may be performed under different conditions.

For diluted sulfuric acid treatment, for example, the concentration of sulfuric acid is preferably 0.1 to 15 wt. %, more preferably 0.5 to 5 wt. %. The reaction temperature can be set in a range of 100 to 300° C., preferably at 120 to 250° C. The reaction time can be set in a range of one second to 60 minutes. The number of treatment is not particularly limited, and it may be performed at least once. When the treatment is performed twice or more, the first treatment and the second treatment may be performed under different conditions. Because the hydrolysate obtained by the diluted sulfuric acid treatment contains an acid, it needs to be neutralized before using it in the hydrolysis reaction.

Regarding the condition of the enzymatic treatment of cellulose-containing biomass in the present invention, when an enzyme composition for saccharification of biomass containing a cellulase derived from filamentous fungi and the mutant glucosidase of the present invention is used, the treatment is preferably carried out at a temperature of 40° C. to 60° C., pH of 3 to 7, and a cellulose-containing biomass solid content concentration of 0.1 to 30%. By setting the condition of the enzymatic treatment in the above range, the cellulose degradation efficiency of a cellulase derived from filamentous fungi and a glucosidase derived from a thermophile can be maximized. Some of the glucosidase derived from a thermophile naturally have an optimum reaction temperature of near 100° C.; however, the glucosidase derived from a thermophile used in the present invention exhibits a sufficiently high specific activity even at 40° C. to 60° C. and can efficiently degrade cellulose-containing biomass in the co-presence of a cellulase derived from filamentous fungi. This enzymatic treatment may be carried out batch-wise or in a continuous manner.

Owing to a high β-glucosidase activity of the enzyme composition for saccharification of biomass containing the mutant glucosidase of the present invention, a sugar liquid obtained by hydrolysis of cellulosic biomass using this enzyme composition has characteristics of having small content of cellobiose but a large amount of glucose. Accordingly, a sugar liquid obtained by using the enzyme composition for saccharification of biomass according to the present invention can be favorably utilized as a carbon source for the growth of microorganisms or cultured cells or for fermentative production using these microorganisms or cultured cells. Examples of the microorganism or the cultured cell used here include yeast such as baker's yeast used in the fermentation industry, bacteria such as E. coli and the coryneform group of bacteria, filamentous fungi, actinomycetes, animal cells, and insect cells. The microorganisms and the cells to be used may be those isolated from natural environments or those having partially modified properties by mutation and genetic recombination. Also, because a sugar liquid derived from cellulose-containing biomass contains pentose such as xylose, a microorganism having an enhanced pentose metabolism pathway is preferably used. Also, using such a sugar liquid as the fermentation raw material, a chemical product can be produced. Specific examples of the chemical product include a substance that is mass-produced in the fermentation industry such as an alcohol, an organic acid, an amino acid, and a nucleic acid, for example, an alcohol such as ethanol, 1,3-propanediol, 1,4-butanediol, and glycerol, an organic acid such as acetic acid, lactic acid, pyruvic acid, succinic acid, malic acid, itaconic acid, and citric acid, a nucleoside such as inosine and guanosine, a nucleotide such as inosinic acid and guanylic acid, and an amine compound such as cadaverine. Further, the sugar liquid can also be applied to the production of an enzyme, an antibiotic, a recombinant protein, and so on.

The sugar liquid obtained by the hydrolysis of cellulosic biomass using the enzyme composition for saccharification of biomass according to the present invention can be used as a sugar liquid after removing the undegraded solid residues as needed, or be directly used as a sugar liquid with the solid residues still contained therein.

In the method for hydrolyzing biomass using the enzyme composition for saccharification of biomass according to the present invention, the used enzyme composition can be separated and recovered from the sugar liquid obtained by the enzymatic treatment of cellulose-containing biomass. Although the method of separation and recovery is not particularly limited, compared to a conventional unglycosylated glucosidase, the mutant glucosidase of the present invention has a characteristic of having a greatly reduced adsorptivity for cellulose-containing biomass, particularly for lignocellulose, and also for an ultrafiltration membrane. Therefore, for separation and recovery of the used enzyme composition, a method of subjecting the hydrolysate to solid-liquid separation as needed, filtering the sugar liquid thus obtained through an ultrafiltration membrane, and separating and recovering the enzyme composition as a non-permeable liquid is preferably used.

As the solid-liquid separation technique in the method for hydrolyzing biomass according to the present invention, either the filtration method or the centrifugation method can be used. Examples of the device for carrying out the solid-liquid separation include, but are not limited to, a belt filter, a screw decanter, a continuous centrifuge, a filter press, and a drum filter.

In the method for hydrolyzing biomass according to the present invention, as the ultrafiltration membrane used for separation and recovery of the enzyme composition, ones made of polyethersulfone (PES), polysulfone (PS), polyacrylonitrile (PAN), poly vinylidene difluoride (PVDF), regenerated cellulose, cellulose, a cellulose ester, sulfonated polysulfone, sulfonated polyethersulfone, polyolefin, polyvinyl alcohol, polymethyl methacrylate, polytetrafluoroethylene and the like can be used. Among them, from the viewpoint of long-term use, an ultrafiltration membrane made of a synthetic polymer other than cellulose is preferred. Generally, an ultrafiltration membrane made of a synthetic polymer has a problem that an enzyme (protein) has high adsorptivity for such a membrane. However, the enzyme composition separated and recovered in the present invention has reduced adsorptivity owing to the effect of glycosylation, and thus is preferably used. With regard to the molecular weight cutoff of the ultrafiltration membrane used in the present invention, an ultrafiltration membrane having a molecular weight cutoff of 500 Da to 100000 Da can be used. Among such ultrafiltration membranes, particularly, one with a molecular weight cutoff ranging from 10000 Da to 30000 Da, which can separate and recover both of the mutant glucosidase of the present invention and the cellulase component derived from filamentous fungi with good yield can be most preferably used.

The filtration method using an ultrafiltration membrane includes dead-end filtration and cross-flow filtration, and from the viewpoint of inhibition of membrane fouling, cross-flow filtration is preferred. Also, as the form of the membrane of ultrafiltration membrane to be used, an appropriately formed membrane such as a flat type membrane, a spiral type membrane, a tubular type membrane, and a hollow yarn type membrane can be used. Specific examples include G-5 type, G-10 type, G-20type, G-50 type, PW type, and HWS UF type, all of which are supplied by DESAL, HFM-180, HFM-183, HFM-251, HFM-300, HFM-116, HFM-183, HFM-300, HFK-131, HFK-328, MPT-U20, MPS-U20P, and MPS-U20S, all of which are supplied by Koch Membrane Systems Inc., SPE1, SPE3, SPE5, SPE10, SPE30, SPV5, SPV50, and SOW30, all of which are supplied by Synder Filtration, the product of microza(R) UF series manufactured by Asahi Kasei Corporation corresponding to a molecular weight cutoff of 3000 to 100000, and NTR7410 and NTR7450 manufactured by Nitto Denko Corporation.

EXAMPLES

Hereinbelow, the present invention will be specifically described with reference to Examples. However, the present invention is not limited to these Examples.

Comparative Example 1

Preparation of β-Glucosidase Derived from
*Pyrococcus furiosus* (1)

A β-glucosidase derived from the hyperthermophilic archaea *Pyrococcus furiosus* (hereinbelow, referred to as "PfuBGL") is so heat resistant that it is still active at 100° C. or higher, and it hydrolyzes various kinds of cellooligosaccharides to produce glucose; therefore, PfuBGL is anticipated for effective utilization of cellulosic biomass.

As to the PfuBGL gene, the gene shown in SEQ ID NO: 3 was entirely synthetized and linked to NcoI and BamHI of pET-11d using Ligation High (Toyobo Co., Ltd.), and the resulting vector was used for transformation of JM109 (Takara Bio Inc.). Screening was performed using an LB agar medium containing ampicillin as an antibiotic. From the transformed JM109 strain, the vector pET-PfuBGL thus prepared was isolated by the miniprep kit (QIAGEN) and subjected to a nucleotide sequence analysis. The pET-PfuBGL was used for transformation of the expression E. coli BL21 (DE3)pLysS strain, whereby a BL21-PfuBGL strain was prepared. The BL21-PfuBGL strain was inoculated into 10 mL of an ampicillin-containing LB agar medium, followed by shaking culture (preculture) at 37° C. overnight. As the main culture, the bacteria obtained by the preculture were inoculated into 1 L of an ampicillin-containing LB agar medium, and shaking culture was performed until OD 600, the absorbance at a wavelength of 600 nm, reached 0.8. Subsequently, isopropyl-1-thio-β-D-galactoside (IPTG) was added so that the final concentration was 0.4 mM, and shaking culture was further continued at 25° C. overnight. After culturing, the bacteria were collected by centrifugation and resuspended in a 50 mM tris-HCl buffer (pH 8.0). The resulting solution was subjected to ultrasonic disintegration while ice-cooling, and the supernatant was collected by centrifugation as a cell-free extract. The cell-free extract thus obtained was kept warm at 85° C. for 15 minutes, and coagulation sedimentation of E. coli-derived proteins other than the glucosidase took place. The sediment was removed by centrifugation and the supernatant was dialyzed against a 50 mM acetate buffer (pH 5.0) through a dialysis membrane made of regenerated cellulose with a molecular weight cutoff of 10000 (manufactured by Spectrum Laboratories, Inc.). The protein solution thus obtained was used as the wild-type PfuBGL.

Example 1

Determination of the N-Linked Glycosylation Sequence-Introduction Site in PfuBGL First of all, the determination of the primary sequence and the tertiary structure was attempted to search for the glycosylation sequence-introduction site in PfuBGL.

To perform alignment with respect to a PfuBGL homologue, the homologue search server FUGUE was used. As a result, in terms of ZSCORE, which indicates the homology of the sequence, PfuBGL exhibited a maximum score of 71.65 with respect to Glycosyl hydrolase family 1 (ZSCORE≥6.0 indicates 99% confidence). In order to form the alignment of the Glycosyl hydrolase family 1 thus obtained, the JOY server was used. As a result, the sequence of PfuBGL corresponding to the position of the N-linked glycosylation sequence that is present at three sites in the β-glucosidase derived from Aspergillus niger (AspNgBGL) and in the β-glucosidase derived from Trichoderma reesei (TriReBGL) was found not to be the N-linked glycosylation sequence (three sites: H60, L61, and Y62, N148, L149, and Y150, and N374, G375, and M376).

An incomplete x-ray crystal structure of PfuBGL is reported (Thijis K. et al., Biochem. vol. 39, No. 17 (2000)), which has degradation ability of as low as 3.3 Å. A complete structural model has not yet been constructed, and such a model has not yet been registered at Protein Data Bank (PDB) either. In light of the above, in order to determine the tertiary structure of PfuBGL, detailed X-ray crystallography was attempted using new crystal conditions. New crystallization conditions were searched and crystallization was successfully achieved using phosphoric acid as a precipitating agent. An X-ray diffraction experiment was performed in the large synchrotron radiation facility SPring-8, and the structure of PfuBGL was determined with degradation ability of 2.5 Å, whereby a complete model of PfuBGL was successfully constructed. For structural determination, the molecular replacement method was used, and as a model molecule, the β-glucosidase derived from Themosphaera aggregans shown in SEQ ID NO: 8 (ThAggBGY, PDB ID: 1QVB) was used.

From the tertiary structure of PfuBGL thus obtained, in the aforementioned three sites corresponding to the position of the N-linked glycosylation sequence, a site that is exposed to the enzyme surface and not located near the active site, thereby presumably having a little impact on the enzyme activity, was only found in H60, L61, and Y62. Accordingly, this site was determined as the N-linked glycosylation sequence-introduction site, and a mutation of H60N, L61R, and Y62T was introduced by substitution, whereby the amino acid sequence shown in SEQ ID NO: 6 was obtained as the glycosylation mutant PfuBGL.

Example 2

Determination of the N-Linked Glycosylation Sequence-Introduction Site in a Glucosidase Having a Homologous Amino Acid Sequence to PfuBGL To perform alignment between SEQ ID NO: 6 obtained in Example 1 and SEQ ID NO: 8, SEQ ID NO: 10, SEQ ID NO: 12, SEQ ID NO: 14, SEQ ID NO: 16, SEQ ID NO: 18, and SEQ ID NO: 20, an alignment was formed using ClustalW and BOXSHADE, both of which are software that is well-known to those skilled in the art (FIG. 2-1 and FIG. 2-2). In SEQ ID NO: 8, SEQ ID NO: 10, SEQ ID NO: 12, SEQ ID NO: 14, SEQ ID NO: 16, SEQ ID NO: 18, or SEQ ID NO: 20, a site corresponding to the glycosylation sequence Asn-Arg-Thr (N-R-T) in SEQ ID NO: 6 was determined as the glycosylation sequence-introduction site in each sequence.

Example 3

Preparation of the Glycosylated Mutant PfuBGL (1)

The glycosylated mutant PfuBGL shown in SEQ ID NO: 6 was prepared.

First of all, using the mutation-introducing primers 5'-CCACATATTGGCACCTCTATAAGCAAGATCATG-3' (SEQ ID NO: 21) and 5'-CATGATCTTGCTTAGTGCGGT-TCCAATATGCTGG-3' (SEQ ID NO: 22) for introducing the glycosylation sequence determined in Example 1 into PfuBGL shown in SEQ ID NO: 4, a N-linked glycosylation sequence mutation was introduced by site-directed mutagenesis. After confirming the sequence of the gene thus obtained, it was inserted between the EcoRI and NotI sites in the yeast expression vector pPIC9, which originally possesses the α factor secretion signal sequence. The mutation-introduced gene was used for transformation of E. coli, and the colony having the gene having the desired mutation was confirmed by a sequencer.

Yeast competent cells produced by a general technique were mixed with the mutant plasmids, whereby transformation was performed using GENE PULSERII (Bio-Rad Laboratories, Inc.) under the conditions of 1.7 kV, 25 μF, and 200Ω. The transformed yeast was streaked onto a RDB plate. Three days later, from the colonies that appeared on the plate, 10 colonies were selected and checked for the expression. A clone in which the expression of the desired protein was confirmed by polyacrylamide gel electrophoresis was selected.

As the seed culture, the yeast colony on the plate was inoculated into 2 mL of a BMGY medium and cultured for two days. Subsequently, as the main culture, 2 mL of the yeast seed culture liquid was added to 1 L of a BMGY medium and cultured for two days so as to allow yeast to sufficiently proliferate. Then, 1 L of the culture liquid was subjected to centrifugation once to precipitate yeast, and the BMGY medium was exchanged for a 2% methanol-containing BMMY medium. The yeast was then resuspended in the medium, followed by culturing for 48 hours. The medium containing the expressed protein was collected by centrifugation and filtered through a filter, followed by ammonium sulfate precipitation using 70% (w/v) ammonium sulfate. The precipitate was collected by centrifugation and dissolved in a buffer, and dialysis was performed and the desired protein was obtained.

The enzyme thus obtained was treated with EndoH and subjected to polyacrylamide gel electrophoresis (FIG. 3). The preparation of the N-linked glycosylated mutant PfuBGL was confirmed by a band shift before and after the EndoH treatment.

Example 4

Enzyme Activity of the Glycosylated Mutant PfuBGL (2)

The glycosylated mutant PfuBGL and PfuBGL were compared for the β-glucosidase activity. Using a 10 mM cellobiose/50 mM acetate buffer solution as a substrate, the enzymes prepared in Example 2 and Comparative Example 1 were each added at a final concentration of 0.23 mg/mL and the enzymatic reaction was carried out at 50° C. For quantitation of the product, Glucose Test Wako II (Wako Pure Chemical Industries, Inc.) was used.

One unit (U) of the β-glucosidase activity was calculated in accordance with the following formula.

One unit (U) of the β-glucosidase activity=the concentration of glucose produced upon completion of the reaction (g/L)×1000/180/30

Further, a specific β-glucosidase activity per the amount of β-glucosidase (mg) was calculated by the following formula.

Specific β-glucosidase activity (U/mg protein)=β-glucosidase activity (U)/the amount of β-glucosidase added for the activity measurement PfuBGL produced 1.58 g/L, while the glycosylated mutant PfuBGL produced 1.34 g/L glucose upon completion of the reaction. Also, the specific activity of the glycosylated mutant PfuBGL was 85% relative to the specific activity of PfuBGL, clearing indicating that the introduction of the glycosylation sequence mutation into the site determined in Examine 1 did not cause a loss of the enzyme activity. From this, it was confirmed that the glycosylated mutant PfuBGL is utilizable in place of PfuBGL.

Example 5

Heat Stability of the Glycosylated Mutant PfuBGL

The changes in the amount of glucose produced up to 24 hours when the product was kept warm at 50° C., 60° C., 70° C., 80° C., and 90° C. were measured.

Figure 4:
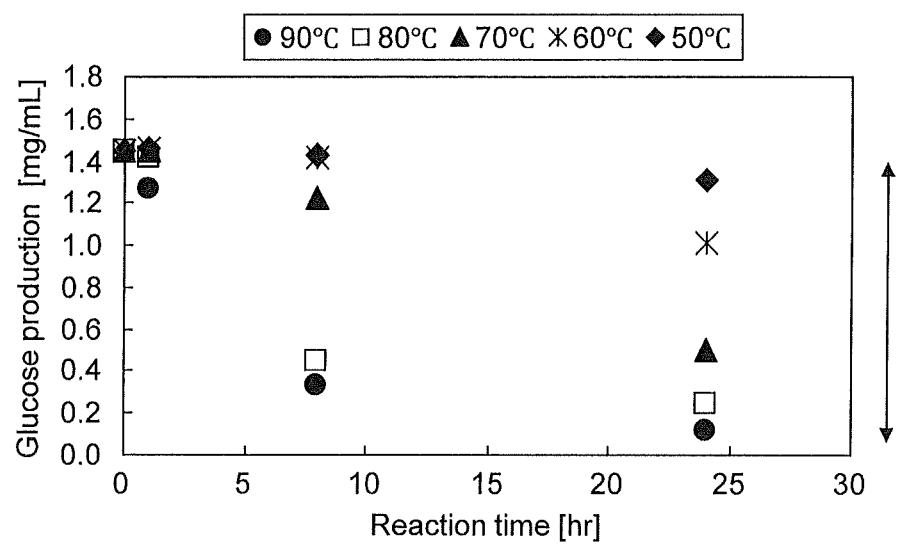
FIG. 4 is a graph showing the results of evaluation of enzyme heat stability by measuring the changes in the amount of glucose produced by cellobiose degradation by PfuBGL at a heat retention time of 50 to 90° C. in Example 4.
Figure 5:
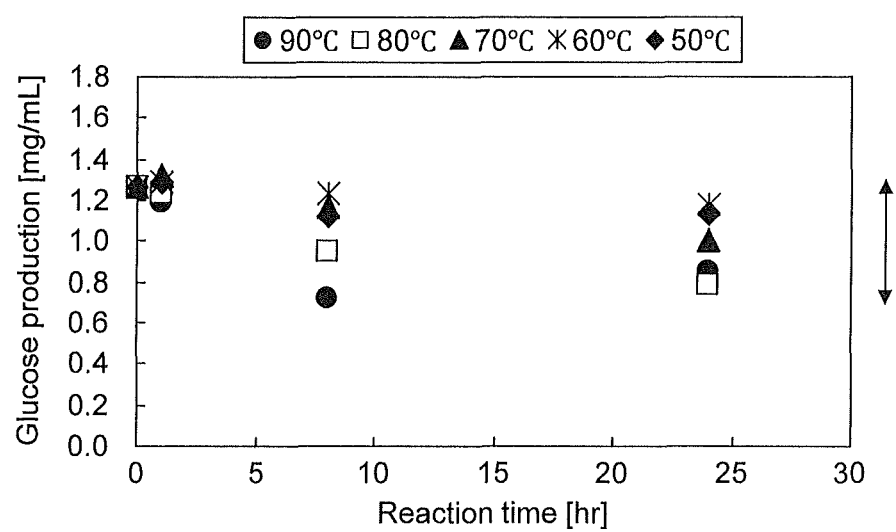
FIG. 5 is a graph showing the results of evaluation of enzyme heat stability by measuring the changes in the amount of glucose produced by cellobiose degradation by the glycosylated mutant PfuBGL at a heat retention time of 50 to 90° C. in Example 4.

The enzymes prepared in Example 2 and Comparative Example 1 (protein concentration of 1.0 mg/mL) were each kept warm at 50° C., 60° C., 70° C., 80° C., or 90° C. At each heat retention time, a substrate, which was a 10 mM cellobiose/50 mM acetate buffer solution, was added, and the enzymatic reaction was carried out for 30 minutes at the heat retention temperature. The solution after the reaction was collected and the product was quantitated using Glucose Test Wako II (Wako Pure Chemical Industries, Inc.) (FIG. 4 and FIG. 5).

By heating up to 24 hours, compared to PfuBGL, the glycosylated mutant PfuBGL exhibited more reduced enzyme inactivation at a high temperature. This finding confirmed that the glycosylated mutant PfuBGL achieved improved enzyme stability by acquiring a higher heat resistance than PfuBGL.

Reference Example 1

Preparation of Lignocellulose

Lignocelluloses 1 to 3 to be used for the hydrolysis using an enzyme composition containing the glycosylated mutant glucosidase were prepared as follows.

1. Preparation of Lignocellulose 1 (Ammonia Treatment)

As cellulose, rice straw was used. The above cellulose was placed in a small reactor (manufactured by Taiatsu Techno, TVS-N2 30 ml) and cooled with liquid nitrogen. To this reactor, ammonia gas was infused and the sample was completely immersed in liquid ammonia. The reactor was capped and left at room temperature for about 15 minutes. Further, it was treated in an oil bath of 150° C. for one hour. After the treatment, the reactor was taken out of the oil bath and ammonia gas was immediately leaked in a draft chamber. Subsequently, the inside of the reactor was dried by vacuuming down to 10 Pa by a vacuum pump. The resulting product was used in the following Examples as lignocellulose 1.

2. Preparation of Lignocellulose 2 (Diluted Sulfuric Acid Treatment)

As cellulose, rice straw was used. The cellulose was immersed in a 1% aqueous solution of sulfuric acid, followed by autoclave treatment (manufactured by Nitto koatsu K.K.) at 150° C. for 30 minutes. After the treatment, solid-liquid separation was performed to separate an aqueous solution of sulfuric acid (hereinbelow, diluted sulfuric acid treatment liquid) from sulfuric acid-treated cellulose. Subsequently, sulfuric acid-treated cellulose and the diluted sulfuric acid treatment liquid were mixed by stirring so that the solid content concentration was 10 wt. %. Subsequently, pH was adjusted to around 5 with sodium hydroxide. The resulting product was used in the following Examples as lignocellulose 2.

3. Preparation of Lignocellulose 3 (Hydrothermal Treatment)

As cellulose, rice straw was used. The above cellulose was immersed in water and subjected to autoclave treatment (manufactured by Nitto koatsu K.K.) at 180° C. for 20 minutes while stirring. In this treatment, the pressure was 10 MPa. After the treatment, the resulting product was subjected to solid-liquid separation by centrifugation (3000 G) to separate the solution component (hereinbelow, the hydrothermal treatment solution) from the treated biomass component. The resulting treated biomass component was used in the following Examples as lignocellulose 3.

Example 6

Hydrolysis of Lignocellulose Using the Enzyme Composition Composed of a Mixture of Cellulases Derived from Filamentous Fungi and the Glycosylated Mutant PfuBGL (1)

Figure 6:
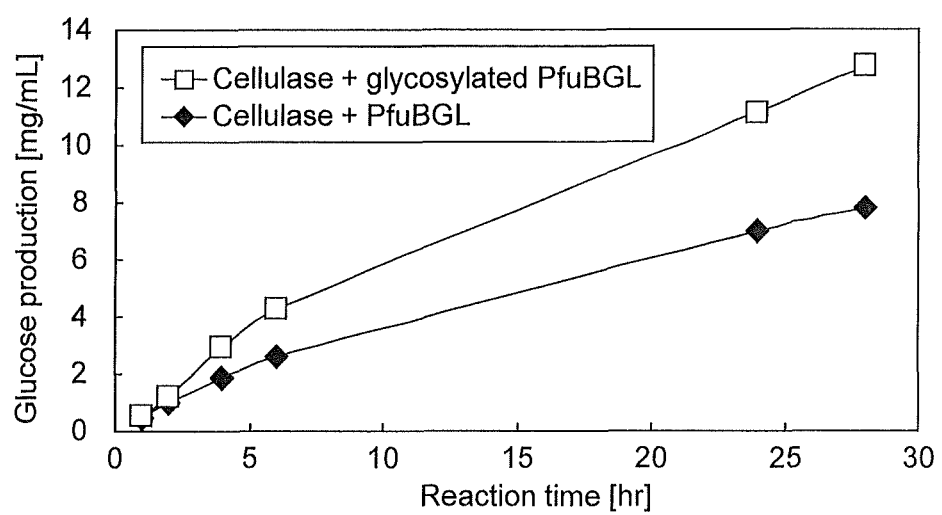
FIG. 6 is a graph showing the results of comparison of the changes in the amount of glucose produced between the case in which an enzyme composition containing a cellulase derived from the genus *Trichoderma*+the glycosylated mutant PfuBGL was allowed to act on the lignocellulose substrate and the case in which an enzyme composition containing a cellulase derived from the genus *Trichoderma*+PfuBGL was allowed to act on the lignocellulose substrate in Example 5. As the substrate, 5 wt. % lignocellulose was used, and the reactions were allowed to proceed up to 28 hours at 50° C., and the reaction product was sampled as appropriate and measured for the glucose concentration. Cellulase was added at 0.5 mg/mL and glucosidase was added at 0.005 mg/mL (1/100 of the amount of cellulase).

The changes in the amount of glucose produced by allowing the enzyme composition to act on the lignocellulose substrate were compared. A 50 mM acetate buffer (pH 5.0) in which 5 wt. % lignocellulose 1 (prepared in Reference Example 1) was suspended was used as a substrate. The reaction was allowed to proceed up to 28 hours at 50° C., and the reaction product was sampled as appropriate and measured for the glucose concentration (FIG. 6). As the mixture of cellulases derived from filamentous fungi, commercially available cellulase derived from *Trichoderma reesei* (Celluclast, Sigma) was used. As glucosidase, the glycosylated mutant PfuBGL prepared in Example 2 and PfuBGL prepared in Comparative Example 1 were each used. Cellulase was added at 0.5 mg/mL and glucosidase was added at 0.005 mg/mL (1/100 of the amount of cellulase).

Comparing the use of PfuBGL and the use of the glycosylated mutant PfuBGL, the amount of glucose produced by the glycosylated mutant PfuBGL after 28 hours of reaction was greatly increased, and it was 1.6 times as much as the amount produced by PfuBGL. It was revealed that the addition of the glycosylated mutant PfuBGL only in an amount of 1/100 the mount of cellulase was tremendously effective for increasing the production amount of glucose.

Reference Example 2

**Preparation of a Cellulase Derived from *Trichoderma***

A cellulase derived from *Trichoderma* was prepared by the following method.

1. Preculture

The following substances were added to distilled water in the amounts indicated below; corn steep liquor 5% (w/vol), glucose 2% (w/vol), ammonium tartrate 0.37% (w/vol), ammonium sulfate 0.14% (w/vol), potassium dihydrogen phosphate 0.2% (w/vol), calcium chloride dihydrate 0.03% (w/vol), magnesium sulfate heptahydrate 0.03% (w/vol), zinc chloride 0.02% (w/vol), iron (III) chloride hexahydrate 0.01% (w/vol), copper(II) sulfate pentahydrate 0.004% (w/vol), manganese chloride tetrahydrate 0.0008% (w/vol), boric acid 0.0006% (w/vol), and hexaammonium heptamolybdate tetrahydrate 0.0026% (w/vol). Then, 100 mL of the resulting solution was poured into a 500 mL triangle flask with a baffle and sterilized by autoclaving at 121° C. for 15 minutes. After naturally cooling, PE-M and Tween 80, which were each separately sterilized by autoclaving at 121° C. for 15 minutes, were each added at 0.1%. To the resulting preculture medium, *Trichoderma reesei* ATCC66589 was inoculated at 1×10⁵/mL, and preculture was performed by shaking at 28° C. for 72 hours at 180 rpm (shaker: BIO-SHAKER BR-40LF manufactured by Taitec Corporation).

2. Main Culture

The following substances were added to distilled water in the amounts indicated below; corn steep liquor 5% (w/vol), glucose 2% (w/vol), cellulose (Avicel) 10% (w/vol), ammonium tartrate 0.37% (w/vol), ammonium sulfate 0.14% (w/vol), potassium dihydrogen phosphate 0.2% (w/vol), calcium chloride dihydrate 0.03% (w/vol), magnesium sulfate heptahydrate 0.03% (w/vol), zinc chloride 0.02% (w/vol), iron (III) chloride hexahydrate 0.01% (w/vol), copper(II) sulfate pentahydrate 0.004% (w/vol), manganese chloride tetrahydrate 0.0008% (w/vol), boric acid 0.0006% (w/vol), and hexaammonium heptamolybdate tetrahydrate 0.0026% (w/vol). Then, 2.5 L of the resulting solution was poured into a 5 L stirring jar (DPC-2A manufactured by ABLE & Biott Co., Ltd.) and sterilized by autoclaving at 121° C. for 15 minutes. After naturally cooling, PE-M and Tween 80, which were each separately sterilized by autoclaving at 121° C. for 15 minutes, were each added at 0.1%. In this, 250 mL of *Trichoderma reesei* ATCC66589 that had been precultured in the liquid culture medium by the aforementioned method was inoculated. Thereafter, the fungi were cultured at 28° C. for 87 hours at 300 rpm with an aeration rate of 1 vvm, followed by centrifugation, and the supernatant was filtered through a membrane (STERICUP-GV, material: PVDF, manufactured by Millipore Corporation).

Example 7

Hydrolysis of Lignocellulose Using the Enzyme Composition Composed of a Mixture of Cellulases Derived from Filamentous Fungi and the Glycosylated Mutant PfuBGL (2)

Hydrolysis of lignocelluloses 1 to 3 was performed in the same manner as Example 6 except for using lignocelluloses 1 to 3 prepared in Reference Example 1 as the substrate, the culture liquid of *Trichoderma reesei* prepared in Reference Example 2 as the mixture of cellulases derived from filamentous fungi, and adding cellulase at 1.0 mg/mL and glucosidase at 0.005 mg/mL (1/100 of the amount of cellulase).

In Table 2, the concentrations of glucose (g/L) produced after 28 hours of reaction were compared.

TABLE 2

| | Concentration of glucose produced (g/L) | |
|---|---|---|
| Substrate | Wild-type PfuBGL | Glycosylated mutant PfuBGL |
| Lignocellulose 1 (Ammonia treatment) | 5 g/L | 15 g/L |
| Lignocellulose 2 (Diluted sulfuric acid treatment) | 3 g/L | 16 g/L |
| Lignocellulose 3 (Hydrothermal treatment) | 4 g/L | 18 g/L |

Comparing the use of PfuBGL and the use of the glycosylated mutant PfuBGL, the amount of glucose produced by the glycosylated mutant PfuBGL after 28 hours of reaction was greatly increased, and it was 1.8 times as much as the amount produced by PfuBGL. It was revealed that the addition of the glycosylated mutant PfuBGL only in an amount of 1/200 the mount of cellulase produced an effect of greatly increasing the production amount of glucose. It was revealed that not only commercially available cellulase such as the one used in Example 6 but also the culture liquid of *Trichoderma reesei* exerted an effect in use with a glycosylated mutant.

Example 8

Hydrolysis of Lignocellulose Using the Enzyme Composition Composed of a Mixture of Cellulases Derived from Filamentous Fungi and the Glycosylated Mutant PfuBGL (3)

Using the enzyme composition composed of a cellulase derived from filamentous fungi and the glycosylated mutant PfuBGL, the amounts of glucose produced were comparatively studied by varying the reaction temperature conditions of hydrolysis. By setting the reaction temperature at 30° C., 40° C., 50° C. (Example 7), or 60° C., the hydrolysis was performed by a similar procedure to Example 7, and the amount of glucose produced after 28 hours was measured. As the substrate, lignocellulose 1 was used.

TABLE 3

| Reaction temperature of hydrolysis (° C.) | Concentration of glucose produced (g/L) |
| --- | --- |
| 30° C. | 5 g/L |
| 40° C. | 13 g/L |
| 50° C. (Example 7) | 15 g/L |
| 60° C. | 7 g/L |

As shown in Table 3, it was revealed that it was preferable to set the reaction temperature in a range of 40° C. to 50° C. when a cellulase derived from filamentous fungi, particularly a cellulase derived from *Trichoderma* was used. This result reflects the fact that the optimum reaction temperature for a cellulase derived from *Trichoderma* is 40° C. to 50° C. That is, it was revealed that although the glucosidase derived from a thermophile according to the present invention was still highly active at 50° C. or higher, when it is used as an enzyme composition for saccharification of biomass containing a cellulase derived from filamentous fungi, the reaction was preferably carried out within a range of the optimum reaction temperature for the cellulase derived from filamentous fungi.

Example 9

Hydrolysis of Lignocellulose Using the Enzyme Composition Composed of a Mixture of Cellulases Derived from Filamentous Fungi and the Glycosylated Mutant PfuBGL (4)

Using the enzyme composition composed of a cellulase derived from filamentous fungi and the glycosylated mutant PfuBGL, the amounts of glucose produced were comparatively studied by varying the pH conditions of the hydrolysis reaction. By setting the pH of the hydrolysis reaction to 1.2, 3.5, 5.0 (Example 7), 7.0, or 8.2 by the addition of diluted sulfuric acid, the hydrolysis was performed by a similar procedure to Example 7, and the amount of glucose produced after 28 hours was measured. As the substrate, lignocellulose 1 was used.

TABLE 4

| Reaction pH of hydrolysis | Concentration of glucose produced (g/L) |
| --- | --- |
| 1.2 | 2 g/L |
| 3.5 | 12 g/L |
| 5 (Example 7) | 15 g/L |
| 7 | 10 g/L |
| 8.2 | 5 g/L |

As shown in Table 4, it was revealed that it was preferable to carry out the hydrolysis in a range of pH 3.5 to pH 7 when a cellulase derived from filamentous fungi, particularly a cellulase derived from *Trichoderma* is used.

Comparative Example 2

Preparation of a Glucosidase Homologous to PfuBGL (2)

Seven kinds of glucosidases having homologous amino acid sequences to PfuBGL prepared in Comparative Example 1 were prepared as follows.

DNA sequences of SEQ ID NOs: 23, 25, 27, 29, 31, 33, and 35 were each entirely synthesized and incorporated into the cloning site of pET-11d (between NcoI and BamHI), whereby the expression vector for each of the above DNA was constructed. Subsequently, in a similar manner to Comparative Example 1, the wild-type glucosidases represented by SEQ ID NOs: 24, 26, 28, 30, 32, 34, and 36 (ThAggBGY, CmGHFP, SaBGAL, SsoBGAL, PtBGAL, TvBGAL, and FnGHFP) were obtained.

Example 10

Preparation of a Glycosylated Mutant Glucosidase Homologous to PfuBGL

Based on the information of glycosylation sequence-introduction site in PfuBGL determined in Example 2, the sugar chain-introduction site in the wild-type glucosidases obtained in Comparative Example 2 (ThAggBGY, CmGHFP, SaBGAL, SsoBGAL, PtBGAL, TvBGAL, and FnGHFP) were determined, whereby the glycosylated mutant glucosidases were each prepared.

DNA sequences of SEQ ID NOs: 37, 39, 41, 43, 45, 47, and 49 encoding glycosylated mutant glucosidase were each entirely synthesized and incorporated between EcoRI and NotI of the pCU9 vector, whereby the expression vector for each of the above DNA was constructed. Subsequently, in a similar manner to Example 3, glycosylated mutant glucosidases represented by the amino acid sequences SEQ ID NOs: 38, 40, 42, 44, 46, 48, and 50 were obtained.

Example 11

Enzyme Activity of the Glycosylated Mutant Glucosidase

The enzyme activity of the glycosylated mutant glucosidases obtained in Example 10 was measured in a similar manner to Example 4 and compared with the enzyme activity of each wild-type glucosidase obtained in Comparative Example 2. Setting the enzyme activity of each wild-type glucosidase at 100, the enzyme activity of the glycosylated mutant was shown as relative activity (%) in Table 5.

TABLE 5

| Entry No. | SEQ ID NO | Glucosidase | Relative activity (%) of glycosylated mutant glucosidase to wild-type |
| --- | --- | --- | --- |
| 1 (Example 4) | 6 | PfuBGL | 85% |
| 2 | 38 | ThAggBGY | 90% |
| 3 | 40 | CmGHFP | 83% |
| 4 | 42 | SaBGAL | 87% |
| 5 | 44 | SsoBGAL | 81% |
| 6 | 46 | PtBGAL | 85% |
| 7 | 48 | TvBGAL | 93% |
| 8 | 50 | FnGHFP | 78% |

In Table 5, the glycosylated mutant glucosidases were found to retain the enzyme activity in comparison with the wild-type glucosidase before glycosylation.

Example 12

Heat Stability of the Glycosylated Mutant Glucosidase

In a similar manner to Example 5, a heat stability test was performed on each wild-type glucosidase obtained in Comparative Example 2 and on each glycosylated mutant glucosidase obtained in Example 10. Regarding the heat stability, by setting the enzyme activity before applying heat at 100, the residual activity at each a heat retention time was shown as relative activity in FIGS. 8 to 20. It was revealed that in all glucosidases, the glycosylated mutants (FIG. 9, FIG. 11, FIG. 13, FIG. 15, FIG. 17, FIG. 19, and FIG. 21) exhibited improved heat stability compared to the wild-type (FIG. 8, FIG. 10, FIG. 12, FIG. 14, FIG. 16, FIG. 18, and FIG. 20).

Example 13

Hydrolysis of Lignocellulose Using the Enzyme Composition Composed of a Mixture of Cellulases Derived from Filamentous Fungi and the Glycosylated Mutant Glucosidase (5)

In a similar manner to Example 6, using each wild-type glucosidase obtained in Comparative Example 2 and each glycosylated mutant glucosidase obtained in Example 10, hydrolysis of lignocellulose 1 (ammonia treatment) prepared in Reference Example 1 was carried out. The amount of glucose produced by each glucosidase after 28 hours of reaction (g/L) was shown in Table 6.

TABLE 6

| | | Concentration of glucose produced (g/L) | |
|---|---|---|---|
| Entry No. | Glucosidase | Wild-type glucosidase (Comparative Example 2) | Glycosylated mutant glucosidase (Example 10) |
| 2 | ThAggBGY | 5 g/L | 10 g/L |
| 3 | CmGHFP | 4 g/L | 9 g/L |
| 4 | SaBGAL | 5 g/L | 11 g/L |
| 5 | SsoBGAL | 6 g/L | 12 g/L |
| 6 | PtBGAL | 5 g/L | 9 g/L |
| 7 | TvBGAL | 4 g/L | 10 g/L |
| 8 | FnGHFP | 6 g/L | 13 g/L |

As shown in Table 6, in the hydrolysis of ammonia-treated lignocellulose 1, the sugar production by the glycosylated mutant glucosidases per unit time was greatly increased compared to the wild-type, confirming that the glycosylated mutant glucosidases had excellent cellulose degradation efficiency.

Example 14

Hydrolysis of Lignocellulose Using the Enzyme Composition Composed of a Mixture of Cellulases Derived from Filamentous Fungi and the Glycosylated Mutant Glucosidase (6)

In a similar manner to Example 6, using each wild-type glucosidase obtained in Comparative Example 2 and each glycosylated mutant glucosidase obtained in Example 10, hydrolysis of lignocellulose 2 (diluted sulfuric acid treatment) prepared in Reference Example 1 was carried out. The amount of glucose produced by each glucosidase after 28 hours of reaction (g/L) was shown in Table 7.

TABLE 7

| | | Concentration of glucose produced (g/L) | |
|---|---|---|---|
| Entry No. | Glucosidase | Wild-type glucosidase (Comparative Example 2) | Glycosylated mutant glucosidase (Example 10) |
| 2 | ThAggBGY | 5 g/L | 10 g/L |
| 3 | CmGHFP | 4 g/L | 9 g/L |
| 4 | SaBGAL | 5 g/L | 11 g/L |
| 5 | SsoBGAL | 6 g/L | 12 g/L |
| 6 | PtBGAL | 5 g/L | 9 g/L |
| 7 | TvBGAL | 4 g/L | 10 g/L |
| 8 | FnGHFP | 6 g/L | 13 g/L |

As shown in Table 7, in the hydrolysis of diluted sulfuric acid-treated lignocellulose 2, the sugar production by the glycosylated mutant glucosidases per unit time was greatly increased compared to the wild-type, confirming that the glycosylated mutant glucosidases had excellent cellulose degradation efficiency.

Example 15

Hydrolysis of Lignocellulose Using the Enzyme Composition Composed of a Mixture of Cellulases Derived from Filamentous Fungi and the Glycosylated Mutant Glucosidase (7)

In a similar manner to Example 6, using each wild-type glucosidase obtained in Comparative Example 1 and Comparative Example 2 and each glycosylated mutant glucosidase obtained in Example 1 and Example 10, hydrolysis of lignocellulose 3 (hydrothermal treatment) prepared in Reference Example 1 was carried out. The amount of glucose produced by each glucosidase after 28 hours of reaction (g/L) was shown in Table 8.

TABLE 8

| | | Concentration of glucose produced (g/L) | |
|---|---|---|---|
| Entry No. | Glucosidase | Wild-type glucosidase (Comparative Example 1, 2) | Glycosylated mutant glucosidase (Example 1, 10) |
| 1 | PfuBGL | 4 g/L | 11 g/L |
| 2 | ThAggBGY | 4 g/L | 12 g/L |
| 3 | CmGHFP | 5 g/L | 14 g/L |
| 4 | SaBGAL | 5 g/L | 14 g/L |
| 5 | SsoBGAL | 4 g/L | 12 g/L |
| 6 | PtBGAL | 5 g/L | 15 g/L |
| 7 | TvBGAL | 4 g/L | 13 g/L |
| 8 | FnGHFP | 6 g/L | 15 g/L |

As shown in Table 8, in the hydrolysis of hydrothermally treated lignocellulose 3, the sugar production by the glycosylated mutant glucosidases per unit time was greatly increased compared to the wild-type, confirming that the glycosylated mutant glucosidases had excellent cellulose degradation efficiency.

Example 16

Hydrolysis of Industrial Pulp Using the Enzyme Composition Composed of a Mixture of Cellulases Derived from Filamentous Fungi and the Glycosylated Mutant Glucosidase In the hydrolysis of industrial pulp, the amount of glucose produced by the action of each wild-type glucosidase obtained in Comparative Example 1 and Comparative Example 2 and that produced by the action of each glycosylated mutant glucosidase obtained in Example 1 and Example 10 were comparatively studied. Hydrolysis was performed in the same manner as Example 6 except for using a 50 mM acetate buffer (pH 5.0) in which 5 wt. % industrial pulp (manufactured by To a Kasei Co., Ltd.) was suspended as a substrate. The amount of glucose produced by each glucosidase after 28 hours of reaction (g/L) was shown in Table 9.

TABLE 9

| | | Concentration of glucose produced (g/L) | |
|---|---|---|---|
| Entry No. | Glucosidase | Wild-type glucosidase (Comparative Example 1, 2) | Glycosylated mutant glucosidase (Example 1, 10) |
| 1 | PfuBGL | 9 g/L | 12 g/L |
| 2 | ThAggBGY | 8 g/L | 11 g/L |
| 3 | CmGHFP | 8 g/L | 11 g/L |
| 4 | SaBGAL | 10 g/L | 13 g/L |
| 5 | SsoBGAL | 10 g/L | 12 g/L |
| 6 | PtBGAL | 9 g/L | 11 g/L |
| 7 | TvBGAL | 8 g/L | 10 g/L |
| 8 | FnGHFP | 11 g/L | 13 g/L |

As shown in Table 9, also in the hydrolysis of industrial pulp, the sugar production by the glycosylated mutant glucosidases per unit time was greatly increased compared to the wild-type, confirming that the glycosylated mutant glucosidases had excellent cellulose degradation efficiency.

Example 17

Selection of the Glycosylation Mutation-Induction Site

Based on the information of the tertiary structure of PfuBGL obtained in Example 1, a further search for glycosylation site was conducted. Protection of the catalytic site by glycosylation was attempted by introducing the glycosylation sequence around the cleft where the enzymatic reaction takes place. First of all, the potential glycosylation mutation-introduction site was limited to, in the part other than the sugar chain mutation-introduction site in PfuBGL described in Example 1, the part that is exposed to the surface of the enzyme. Subsequently, such a position that would not cause the steric hindrance and/or structural deformation by introduction of mutation of the glycosylation sequence Asn-Xaa-Thr (N—X-T) was searched. Also, in the part where the active site of glucosidase was avoided, three mutation-introduction sites were selected.

As a result, in addition to the glycosylation site selected in Example 1, three mutation-introduction sites were newly selected, which were H37-D38-K39 (mutation A), S230-F231-E232 (mutation C), and A364-Y365-E366 (mutation E).

Example 18

Preparation of the Glycosylated Mutant PfuBGL (2)

In order to introduce the glycosylation sequence into the mutation-introduction site determined in Example 17 in the glycosylated mutant PfuBGL shown in SEQ ID NO: 6, using primers for introducing mutation A shown in SEQ ID NO: 57 and SEQ ID NO: 58, N-linked glycosylation sequence mutation was introduced by site-directed mutagenesis. As a result, the glycosylated mutant PfuBGL2A gene of SEQ ID NO: 51 was obtained. Also, as to mutation C and mutation E, using primers for introducing mutation C shown in SEQ ID NO: 59 and SEQ ID NO: 60 and primers for introducing mutation E shown in SEQ ID NO: 61 and SEQ ID NO: 62, respectively, N-linked glycosylation sequence mutation was introduced by site-directed mutagenesis in a similar manner, whereby the glycosylated mutant PfuBGL2C gene shown in SEQ ID NO: 53 and the glycosylated mutant PfuBGL2E gene shown in SEQ ID NO: 55 were each obtained. Using the glycosylated mutant genes prepared as above, the glycosylated mutant PfuBGL2A represented by SEQ ID NO: 52, the glycosylated mutant PfuBGL2C represented SEQ ID NO: 54, and the glycosylated mutant PfuBGL2E represented by SEQ ID NO:56 were each obtained by following the same steps as in Example 3.

Example 19

Enzyme Activity of the Glycosylated Mutant PfuBGL (2)

In a similar manner to Example 4, the enzyme activity of the glycosylated mutant glucosidase PfuBGL2A (SEQ ID NO: 52), the glycosylated mutant PfuBGL2C (SEQ ID NO: 54), and the glycosylated mutant PfuBGL2E (SEQ ID NO: 56) obtained in Example 18 was measured in comparison with the wild-type PfuBGL. Setting the enzyme activity of the wild-type PfuBGL at 100, the enzyme activity of the glycosylated mutant was shown as relative activity (%) in Table 10.

TABLE 10

| Entry No. | SEQ ID NO | Glucosidase | Relative activity (%) of glycosylated mutant glucosidase to wild-type |
|---|---|---|---|
| 9 | 52 | PfuBGL2A | 84 |
| 10 | 54 | PfuBGL2C | 81 |
| 11 | 56 | PfuBGL2E | 85 |

As shown in Table 10, it was found that the mutant glucosidase having two or more sugar chains attached thereto retained the enzyme activity in comparison with the wild-type glucosidase before glycosylation.

Example 20

Hydrolysis of Lignocellulose Using the Enzyme Composition Composed of a Mixture of Cellulases Derived from Filamentous Fungi and Various Kinds of Glycosylated Mutant Glucosidases (8)

In a similar manner to Example 6, using the glycosylated mutant glucosidases (PfuBGL2A, PfuBGL2C, and PfuBGL2E) obtained in Example 18, hydrolysis of lignocellulose 2 (diluted sulfuric acid treatment) prepared in Reference Example 1 was carried out. The amount of glucose produced after 28 hours of reaction (g/L) was shown in Table 11.

TABLE 11

| Entry No. | Glucosidase | Concentration of glucose produced (g/L) | |
|---|---|---|---|
| | | Wild-type glucosidase (Comparative Example 1) | Glycosylated mutant glucosidase (Example 18) |
| 1 | PfuBGL | 3 g/L | — |
| 9 | PfuBGL2A | — | 18 g/L |
| 10 | PfuBGL2C | — | 18 g/L |
| 11 | PfuBGL2E | — | 19 g/L |

As shown in Table 11, it was revealed that the mutant glucosidases having two or more sugar chains attached thereto (SEQ ID NO: 52, SEQ ID NO: 54, and SEQ ID NO: 56) also had greatly improved lignocellulose degradation efficiency compared to an unglycosylated wild-type glucosidase (Comparative Example 1; the amount of glucose produced: 3 g/L).

Example 21

Evaluation of the Adsorptivity of the Glycosylated Mutant Glucosidase to Lignocellulose The adsorptivity of the glycosylated mutant glucosidase to crystalline cellulose (Avicel) and to lignocelluloses 1 to 3 prepared in Reference Example 1 was evaluated. As the glucosidase, the glycosylated mutant PfuBGL prepared in Example 1 and the wild-type PfuBGL prepared in Comparative Example 1 were used, and the enzyme solutions were adjusted so as to have equal specific activities, and further prepared at a final concentration of 100 mM by the addition of an acetate buffer (pH 5). The resulting enzyme solutions were each added to the crystalline cellulose and to lignocelluloses 1 to 3 at a final concentration (solid concentration) of 7.5 wt. %, and the resulting mixtures were kept warm and stirred at 50° C. for one hour. Subsequently, the mixtures after reaction were centrifuged at 15000 rpm for 10 minutes, and the supernatant thus obtained was measured for the cellobiose degradation activity. Setting the enzyme activity of an enzyme solution without crystalline cellulose and lignocelluloses 1 to 3 at 100, the cellobiose degradation activity was evaluated in terms of relative activity (%).

TABLE 12

| Cellulose | Relative activity (%) of cellobiose degradation activity (%) | |
|---|---|---|
| | Wild-type PfuBGL | Glycosylated mutant PfuBGL |
| Crystalline cellulose (Avicel) | 85% | 95% |
| Lignocellulose 1 (Diluted sulfuric acid treatment) | 23% | 84% |
| Lignocellulose 2 (Ammonia treatment) | 62% | 84% |
| Lignocellulose 3 (Hydrothermal treatment) | 34% | 81% |

As shown in Table 12, it was revealed that the cellobiose degradation activity in the supernatant of the glycosylated mutant glucosidase was increased in the presence of any of the lignocelluloses 1 to 3, compared to the wild-type glucosidase. Also, the cellobiose degradation activity in the supernatant was slightly increased also for Avicel, which was crystalline cellulose. From the above results, it was revealed that the glycosylated mutant glucosidase had low adsorptivity particularly for lignocellulose (pre-treatment cellulose product), and thus would be recovered with good yield from the supernatant after solid-liquid separation.

Example 22

Evaluation of the Adsorptivity of the Glycosylated Mutant Glucosidase to an Ultrafiltration Membrane The adsorptivity of the glycosylated mutant glucosidase to an ultrafiltration membrane was evaluated. As the ultrafiltration membrane, VIVASPIN20 (SARTORIUS K.K., made of polyethersulfone, a molecular weight cut off of 10000 Da) was used. As the glucosidase, the glycosylated mutant PfuBGL prepared in Example 1 and the PfuBGL prepared in Comparative Example 1 were used, and the enzyme solutions were adjusted so as to have equal specific activities, and further prepared at a final concentration of 50 mM by the addition of an acetate buffer (pH 5). From these enzyme solutions, 5 mL was transferred to the ultrafiltration membrane VIVASPIN20, followed by centrifugation at 4000 G for 10 minutes. After centrifugation, to the solution remained on the non-permeable side of the ultrafiltration membrane (about 100 µL or less), 3 mL of a 50 mM acetate buffer was added, and the residual products left on the surface of the ultrafiltration membrane and on the inner wall of the container were collected by pipetting. The residual product thus collected was made up to 5 mL, and from this, 10 µL was sampled for the cellobiose degradation activity. The above series of operations was repeated seven times, and setting the initial activity at 100(%), the cellobiose degradation activity was calculated as relative activity (%) at each operation. The results thus obtained are shown in Table 13.

TABLE 13

| Number of repetition of operation | Relative activity (%) of cellobiose degradation activity (%) | |
|---|---|---|
| | Wild-type PfuBGL | Glycosylated mutant PfuBGL |
| 0 (initial) | 100% | 100% |
| 1 | 21% | 114% |
| 2 | 5.4% | 115% |
| 3 | 1.8% | 112% |
| 4 | ND | 116% |
| 5 | ND | 110% |
| 6 | ND | 101% |
| 7 | ND | 98% |

As shown in Table 13, it was revealed that the activity of the unglycosylated wild-type PfuBGL was decreased as the number of repetition of the operation was increased (the activity disappeared at the fourth and subsequent operations). Meanwhile, the glycosylated mutant PfuBGL remained active even after seven repeated operations. That is, it was revealed that the glycosylated mutant glucosidase had low adsorptivity for the ultrafiltration membrane, and thus was recovered with good yield when it was recovered using an ultrafiltration membrane after the hydrolysis reaction.

Example 23

Recovery of the Enzyme Composition in the Hydrolysate Using an Ultrafiltration Membrane From the product of hydrolysis of lignocelluloses 1 to 3 in Example 7, the enzyme composition was recovered as follows. First of all, 10 mL of the hydrolysate was centrifuged and 5 mL of the supernatant was obtained. Subsequently, the supernatant was filtered through a precise membrane filter having an average pore diameter of 0.2 μm (PVDF membrane, manufactured by Millipore Corporation), and the filtrate was collected. The total volume of the filtrate thus obtained was transferred to the ultrafiltration membrane VIVASPIN20 (made of polyethersulfone, a molecular weight cutoff of 10000 Da), followed by centrifugation. The residual product remained on the non-permeable side of the ultrafiltration membrane was collected and measured for the cellobiose degradation activity. By setting the activity of the introduced enzyme at the initial enzyme activity of 100%, the enzyme activity of the enzyme composition recovered as the residual product was calculated in terms of relative value (%).

TABLE 14

| Cellulose | Relative activity (%) of cellobiose degradation activity of the recovered enzyme | |
|---|---|---|
| | Wild-type PfuBGL | Glycosylated mutant PfuBGL |
| Lignocellulose 1 (Diluted sulfuric acid treatment) | 21% | 69% |
| Lignocellulose 2 (Ammonia treatment) | 11% | 51% |
| Lignocellulose 3 (Hydrothermal treatment) | 7.7% | 48% |

As shown in Table 14, it was revealed that the activity of the recovered glycosylated mutant glucosidase was greatly increased compared to the mutant glucosidase. This was assumed to be attributable to decreased adsorptivity of the glycosylated mutant glucosidase for lignocellulose as demonstrated in Example 21, and also to decreased adsorptivity of the glycosylated mutant glucosidase for the ultrafiltration membrane as demonstrated in Example 22.

Example 24

Analysis of the Sugar Chain Component of the Glycosylated Mutant Glucosidase The sugar chain structure of the glycosylated PfuBGL described in Example 1 was analyzed. To 1.33 mg of a sample, which was freeze-dried (−80° C.) glycosylated PfuBGL, 1.33 mL of purified water was added to prepare a 1 mg/mL sample solution. The neutral sugar and amino sugar in this sample solution were quantitated by the following procedure.

1. Neutral Sugar

Into a test tube, 100 μL of the 1 mg/mL sample solution was transferred, which was dried under reduced pressure, to which 200 μL of 2 M trifluoroacetic acid was added. The resulting test tube was subjected to nitrogen substitution and then sealed under reduced pressure. Subsequently, the hydrolysis was performed at 100° C. for six hours, and the resulting product was dried again under reduced pressure. To the residue thus obtained, 200 μL of purified water was added, in which the residue was dissolved. The resulting solution was filtered through a filter of 0.22 μm. A sample obtained by diluting the filtrate 10-fold with purified water was analyzed under the following conditions.

As the analytical instrument, the HPLC system LC20A system (Shimadzu Corporation) and the spectrofluorometer RF-10AXL (Shimadzu Corporation) were used.

The analytical conditions were as follows; TSK-gel Sugar AXG 4.6 mm I.D.×15 cm (Tosoh Corporation), the column temperature, 70° C., the mobile phase, a 0.6 M potassium borate buffer (pH 8.7), and the mobile phase flow rate, 0.4 mL/min.

Using 1 wt. % arginine and 3 wt. % boric acid as the reaction reagent, post-column labeling was performed at a reaction reagent flow rate of 0.5 mL/min and a reaction temperature of 150° C. Also, as to the detection wavelength, the excitation and the detection were performed at 320 nm and 430 nm, respectively. The neutral sugar was quantitated in comparison with each standard product of neutral sugar.

2. Amino Sugar

Into a test tube, 100 μL of the 1 mg/mL sample solution was transferred, which was dried under reduced pressure, to which 200 μL of 4 M trihydrochloric acid was added. The resulting test tube was subjected to nitrogen substitution and then sealed under reduced pressure. Subsequently, the hydrolysis was performed at 100° C. for six hours, and then the resulting product was dried again under reduced pressure. To the residue thus obtained, 200 μL of purified water was added, in which the residue was dissolved. The resulting solution was filtered through a filter of 0.22 μm.

As the analytical instrument, the HPLC system LC20A system (Shimadzu Corporation) and the spectrofluorometer RF-10AXL (Shimadzu Corporation) were used.

The analytical conditions were as follows; TSK-gel SCX 6 mm I.D.×15 cm (Tosoh Corporation), the column temperature, 60° C., the mobile phase, a 0.16 M boric acid potassium borate buffer (pH 7.6), and the mobile phase flow rate, 0.3 mL/min.

Using 1 wt. % arginine and 3 wt. % boric acid as the reaction reagent, post-column labeling was performed at a reaction reagent flow rate of 0.5 mL/min and a reaction temperature of 150° C. Also, as to the detection wavelength, the excitation and the detection were performed at 320 nm and 430 nm, respectively. The neutral sugar was quantitated in comparison with each standard product of neutral sugar.

TABLE 15

| | Sugar | Concentration (nmol/mg) | Composition ratio (*1) |
|---|---|---|---|
| Neutral sugar | Rhamnose | 30 | 1 |
| | Ribose | ND | — |
| | Mannose | 576 | 18 |
| | Arabinose | 24 | 1 |
| | Galactose | 75 | 2 |
| | Xylose | ND | — |
| | Glucose | 54 | 2 |
| Amino sugar | Glucosamine | 62 | 2 |
| | Galactosamine | 37 | 1 |

(*1) By setting the value of the concentration B of glucosamine at "2" as the standard, the concentrations B of other sugars were calculated as relative ratio. In calculating, the digits after the decimal point were rounded to an integer.

As shown in Table 15, it was revealed that the main component of the neutral sugar composing the sugar chain of the sugar chain mutant PfuBGL obtained in Example 1 was mannose. Also, from the composition ratio of mannose to N-glucosamine, the sugar chain mutant PfuBGL was found to have a high mannose type sugar chain.

Industrial Applicability

The glycosylated mutant glucosidase derived from a thermophile according to the present invention can be used for the production of a sugar liquid by cellulose degradation. Because the glycosylated mutant glucosidase derived from a thermophile has an effect of greatly increasing the cellulose degradation efficiency, it is capable of considerably reducing the cost of enzyme. In light of the above, the glycosylated mutant glucosidase derived from a thermophile according to the present invention is extremely industrially beneficial.

All of the publications, patents, and patent applications cited in the present specification are hereby incorporated by reference in their entirety.

The invention claimed is:

1. A method of producing a mutant glucosidase derived from a thermophile having a sugar chain bound to an amino acid side chain of a peptide sequence of the mutant glucosidase by covalent binding and having glucosidase activity, wherein the mutant glucosidase demonstrates enhanced ability to increase saccharification of a lignocellulose substrate which has been subjected to pre-treatment when added to cellulase as compared to the corresponding unglycosylated wild-type glucosidase of SEQ ID NO: 4, SEQ ID NO: 8, SEQ ID NO: 10, SEQ ID NO: 12, SEQ ID NO: 14, SEQ ID NO: 16, SEQ ID NO: 18, and SEQ ID NO: 20, which comprises:

(i) preparing DNA encoding the mutant glucosidase derived from a thermophile by introducing a DNA sequence encoding Asn-X-Ser or Asn-X-Thr (wherein, X is any amino acid except proline) into DNA encoding a glucosidase derived from a thermophile originally devoid of a glycosylation sequence and adding a DNA sequence encoding a secretion signal sequence to the DNA encoding the mutant glucosidase, wherein the glucosidase derived from the thermophile is a protein comprising:

(a) any of the amino acid sequences shown in SEQ ID NO: 4, SEQ ID NO: 8, SEQ ID NO: 10, SEQ ID NO: 12, SEQ ID NO: 14, SEQ ID NO: 16, SEQ ID NO: 18, and SEQ ID NO: 20, or (b) an amino acid sequence having 95% or more identity with any of the amino acid sequences shown in SEQ ID NO: 4, SEQ ID NO: 8, SEQ ID NO: 10, SEQ ID NO: 12, SEQ ID NO: 14, SEQ ID NO: 16, SEQ ID NO: 18, and SEQ ID NO: 20,
and β-glucosidase activity, the DNA sequence encoding Asn-X-Ser or Asn-X-Thr is substituted for amino acids of the glucosidase derived from a thermophile corresponding to amino acids of H60-L61-Y62 in the amino acid sequence shown in SEQ ID NO: 4, (ii) introducing the DNA encoding the mutant glucosidase to which the DNA sequence encoding the secretion signal sequence has been added into an eukaryotic microorganism so that a mutant glucosidase encoded by the DNA of the mutant glucosidase is expressed as a secretory protein, and (iii) isolating and purifying the mutant glucosidase thus expressed as a secretory protein.

2. The method according to claim 1, wherein the sugar chain is a high mannose type sugar chain.

3. The method according to claim 2, wherein the eukaryotic microorganism is *Pichia pastoris*.

4. The method according to claim 2, wherein the secretion signal sequence is an α factor secretion signal sequence.

5. The method according to claim 1, wherein the eukaryotic microorganism is *Pichia pastoris*.

6. The method according to claim 1, wherein the secretion signal sequence is an α factor secretion signal sequence.

7. The method according to claim 1, wherein the mutant glucosidase derived from a thermophile comprises an amino acid sequence shown in any of SEQ ID NO: 6, SEQ ID NO: 38, SEQ ID NO: 40, SEQ ID NO: 42, SEQ ID NO: 44, SEQ ID NO: 46, SEQ ID NO: 48, and SEQ ID NO: 50.

8. The method according to claim 1, wherein the lignocellulose substrate is rice straw.

9. The method according to claim 1, wherein the pretreatment is ammonia treatment, diluted sulfuric acid treatment or hydrothermal treatment.

10. The method according to claim 1, wherein the cellulase is derived from *Trichoderma reesei*.

11. The method according to claim 1, in step (i), when the glucosidase derived from the thermophile is a protein comprising:

(a) the amino acid sequence shown in SEQ ID NO: 4, or (b) the amino acid sequence having 95% or more identity with the amino acid sequence shown in SEQ ID NO: 4 and a β glucosidase activity, the DNA sequence encoding Asn-X-Ser or Asn-X-Thr is substituted for amino acids of the glucosidase derived from a thermophile corresponding to amino acids selected from H37-D38-K39, S230-F231-E232, and A364-Y365-E366 in addition to H60-L61-Y62 in the amino acid sequence shown in SEQ ID NO: 4.

12. The method according to claim 11, wherein the mutant glucosidase derived from a thermophile comprises an amino acid sequence shown in any of SEQ ID NO: 52, SEQ ID NO: 54, and SEQ ID NO: 56.

* * * * *

SEQUENCE LISTING

```
<160> NUMBER OF SEQ ID NOS: 63

<210> SEQ ID NO 1
<211> LENGTH: 466
<212> TYPE: PRT
<213> ORGANISM: Trichoderma reesei

<400> SEQUENCE: 1

Met Leu Pro Lys Asp Phe Gln Trp Gly Phe Ala Thr Ala Ala Tyr Gln
1               5                   10                  15

Ile Glu Gly Ala Val Asp Gln Asp Gly Arg Gly Pro Ser Ile Trp Asp
                20                  25                  30

Thr Phe Cys Ala Gln Pro Gly Lys Ile Ala Asp Gly Ser Ser Gly Val
            35                  40                  45

Thr Ala Cys Asp Ser Tyr Asn Arg Thr Ala Glu Asp Ile Ala Leu Leu
        50                  55                  60

Lys Ser Leu Gly Ala Lys Ser Tyr Arg Phe Ser Ile Ser Trp Ser Arg
65                  70                  75                  80

Ile Ile Pro Glu Gly Gly Arg Gly Asp Ala Val Asn Gln Ala Gly Ile
                85                  90                  95

Asp His Tyr Val Lys Phe Val Asp Asp Leu Leu Asp Ala Gly Ile Thr
            100                 105                 110

Pro Phe Ile Thr Leu Phe His Trp Asp Leu Pro Glu Gly Leu His Gln
        115                 120                 125

Arg Tyr Gly Gly Leu Leu Asn Arg Thr Glu Phe Pro Leu Asp Phe Glu
    130                 135                 140

Asn Tyr Ala Arg Val Met Phe Arg Ala Leu Pro Lys Val Arg Asn Trp
145                 150                 155                 160

Ile Thr Phe Asn Glu Pro Leu Cys Ser Ala Ile Pro Gly Tyr Gly Ser
                165                 170                 175

Gly Thr Phe Ala Pro Gly Arg Gln Ser Thr Ser Glu Pro Trp Thr Val
            180                 185                 190

Gly His Asn Ile Leu Val Ala His Gly Arg Ala Val Lys Ala Tyr Arg
        195                 200                 205

Asp Asp Phe Lys Pro Ala Ser Gly Asp Gly Gln Ile Gly Ile Val Leu
    210                 215                 220

Asn Gly Asp Phe Thr Tyr Pro Trp Asp Ala Ala Asp Pro Ala Asp Lys
225                 230                 235                 240

Glu Ala Ala Glu Arg Arg Leu Glu Phe Phe Thr Ala Trp Phe Ala Asp
                245                 250                 255

Pro Ile Tyr Leu Gly Asp Tyr Pro Ala Ser Met Arg Lys Gln Leu Gly
            260                 265                 270

Asp Arg Leu Pro Thr Phe Thr Pro Glu Glu Arg Ala Leu Val His Gly
        275                 280                 285

Ser Asn Asp Phe Tyr Gly Met Asn His Tyr Thr Ser Asn Tyr Ile Arg
    290                 295                 300

His Arg Ser Ser Pro Ala Ser Ala Asp Asp Thr Val Gly Asn Val Asp
```

```
305                 310                 315                 320
Val Leu Phe Thr Asn Lys Gln Gly Asn Cys Ile Gly Pro Glu Thr Gln
                325                 330                 335

Ser Pro Trp Leu Arg Pro Cys Ala Ala Gly Phe Arg Asp Phe Leu Val
                340                 345                 350

Trp Ile Ser Lys Arg Tyr Gly Tyr Pro Pro Ile Tyr Val Thr Glu Asn
                355                 360                 365

Gly Thr Ser Ile Lys Gly Glu Ser Asp Leu Pro Lys Glu Lys Ile Leu
            370                 375                 380

Glu Asp Asp Phe Arg Val Lys Tyr Tyr Asn Glu Tyr Ile Arg Ala Met
385                 390                 395                 400

Val Thr Ala Val Glu Leu Asp Gly Val Asn Val Lys Gly Tyr Phe Ala
                405                 410                 415

Trp Ser Leu Met Asp Asn Phe Glu Trp Ala Asp Gly Tyr Val Thr Arg
                420                 425                 430

Phe Gly Val Thr Tyr Val Asp Tyr Glu Asn Gly Gln Lys Arg Phe Pro
            435                 440                 445

Lys Lys Ser Ala Lys Ser Leu Lys Pro Leu Phe Asp Glu Leu Ile Ala
    450                 455                 460

Ala Ala
465

<210> SEQ ID NO 2
<211> LENGTH: 434
<212> TYPE: PRT
<213> ORGANISM: Aspergillus niger

<400> SEQUENCE: 2

Met Leu Pro Lys Asp Leu Gln Trp Gly Phe Ala Lys Ala Ala Tyr Gln
1               5                   10                  15

Ile Glu Gly Ala Val Asp Gln Asp Gly Arg Gly Pro Ser Ile Trp Asp
                20                  25                  30

Thr Phe Cys Ala Gln Pro Gly Lys Ile Ala Asp Gly Ser Ser Gly Val
            35                  40                  45

Thr Ala Cys Asp Ser Tyr Asn Arg Thr Ala Glu Asp Ile Ala Leu Leu
        50                  55                  60

Lys Ser Leu Gly Ala Lys Ser Tyr Arg Phe Ser Ile Ser Ser Arg Ile
65              70                  75                  80

Pro Glu Gly Gly Arg Gly Asp Ala Val Asn Gln Ala Gly Ile Asp His
                85                  90                  95

Tyr Val Lys Phe Val Asp Asp Leu Leu Asp Ala Gly Ile Thr Pro Phe
                100                 105                 110

Ile Thr Leu Phe His Trp Asp Leu Leu His Gln Arg Tyr Gly Gly Leu
            115                 120                 125

Leu Asn Arg Thr Glu Phe Pro Leu Asp Phe Glu Asn Tyr Ala Arg Val
        130                 135                 140

Met Phe Arg Ala Leu Pro Lys Val Arg Asn Trp Asn Glu Pro Leu Cys
145                 150                 155                 160

Ser Ala Ile Pro Gly Tyr Gly Ser Gly Ser Phe Ala Pro Gly Arg Gln
                165                 170                 175

Ser Thr Ser Glu Pro Trp Thr Val Gly His Asn Ile Leu Val Ala His
            180                 185                 190

Gly Arg Ala Val Lys Ala Tyr Arg Asp Asp Phe Lys Pro Ala Ser Gly
        195                 200                 205
```

| | | | | | | | | | | | | |
|---|---|---|---|---|---|---|---|---|---|---|---|---|
|Asp|Gly|Gln|Ile|Gly|Ile|Val|Leu|Asn|Gly|Asp|Phe|Thr|Tyr|Pro|Trp|
| |210| | | |215| | | |220| | | | | | |

Asp Gly Gln Ile Gly Ile Val Leu Asn Gly Asp Phe Thr Tyr Pro Trp
    210             215             220

Asp Ala Asp Pro Ala Asp Lys Glu Arg Leu Glu Phe Phe Thr Ala
225             230             235             240

Trp Phe Ala Asp Pro Ile Tyr Leu Gly Asp Tyr Pro Ala Ser Met Arg
            245             250             255

Lys Gln Leu Gly Asp Arg Leu Pro Thr Phe Thr Pro Glu Glu Arg Ala
            260             265             270

Leu Val His Gly Ser Asn Asp Phe Tyr Gly Met Asn His Tyr Thr Ser
            275             280             285

Asn Tyr Ile Arg His Arg Ser Ser Pro Ala Ser Ala Asp Asp Thr Val
            290             295             300

Gly Asn Val Asp Val Leu Phe Thr Asn Lys Gln Gly Asn Cys Ile Gly
305             310             315             320

Pro Glu Thr Gln Ser Pro Trp Leu Arg Pro Cys Ala Ala Gly Phe Arg
            325             330             335

Asp Phe Leu Val Trp Thr Ser Lys Arg Tyr Gly Ser Pro Pro Ile Tyr
            340             345             350

Val Thr Glu Asn Gly Thr Ser Ile Lys Gly Glu Ser Asp Leu Pro Asn
            355             360             365

Glu Lys Ile Leu Glu Asp Asp Phe Arg Val Lys Tyr Tyr Asn Glu Tyr
            370             375             380

Ile Arg Ala Met Val Thr Ala Val Glu Leu Asp Gly Val Asn Val Arg
385             390             395             400

Phe Gly Val Thr Tyr Val Asp Tyr Glu Asn Gly Gln Lys Arg Phe Pro
            405             410             415

Lys Lys Ser Ala Lys Ser Leu Lys Pro Leu Phe Asp Glu Leu Ile Ala
            420             425             430

Ala Ala

<210> SEQ ID NO 3
<211> LENGTH: 1419
<212> TYPE: DNA
<213> ORGANISM: Pyrococcus furiosus

<400> SEQUENCE: 3

```
atggcaaagt tcccaaaaaa cttcatgttt ggatattctt ggtctggttt ccagtttgag    60
atgggactgc aggaagtga agtggaaagc gactggtggg tgtgggttca cgacaaggag   120
aacatagcat caggtctagt aagtggagat ctaccagaga acggcccagc atattggcac   180
ctctataagc aagatcatga cattgcagaa aagctaggaa tggattgtat tagaggtggc   240
attgagtggg caagaatttt tccaaagcca cattttgacg ttaaagttga tgtggaaaag   300
gatgaagaag gcaacataat ttccgtagac gttccagaga gtacaataaa agagctagag   360
aaaattgcca acatggaggc ccttgaacat tatcgcaaga tttactcaga ctggaaggag   420
aggggcaaaa ccttcatatt aaacctctac cactggcctc ttccattatg gattcatgac   480
ccaattgcag taaggaaact tggcccggat agggctcctg caggatggtt agatgagaag   540
acagtggtag agtttgtgaa gtttgccgcc ttcgttgctt atcaccttga tgacctcgtt   600
gacatgtgga gcacaatgaa cgaaccaaac gtagtctaca atcaaggtta cattaatcta   660
cgttcaggat tccaccagg atatctaagc tttgaagcag cagaaaaggc aaaattcaac   720
ttaattcagc tcacatcgg agcatatgat gccataaaag agtattcaga aaaatccgtg   780
ggagtgatat acgcctttgc ttggcacgat cctctagcgg aggagtataa ggatgaagta   840
```

```
gaggaaatca gaaagaaaga ctatgagttt gtaacaattc tacactcaaa aggaaagcta    900
gactggatcg gcgtaaacta ctactccagg ctggtatatg gagccaaaga tggacaccta    960
gttcctttac ctggatatgg atttatgagt gagagaggag gatttgcaaa gtcaggaaga   1020
cctgctagtg actttggatg ggaaatgtac ccagagggcc ttgagaacct tcttaagtat   1080
ttaaacaatg cctacgagct accaatgata attacagaga acggtatggc cgatgcagca   1140
gatagataca ggccacacta tctcgtaagc catctaaagg cagtttacaa tgctatgaaa   1200
gaaggtgctg atgttagagg gtatctccac tggtctctaa cagacaacta cgaatgggcc   1260
caagggttca ggatgagatt tggattggtt tacgtggatt tcgagacaaa gaagagatat   1320
ttaaggccaa gcgccctggt attcagagaa atagccactc aaaaagaaat tccagaagaa   1380
ttagctcacc tcgcagacct caaatttgtt acaagaaag                          1419
```

<210> SEQ ID NO 4
<211> LENGTH: 473
<212> TYPE: PRT
<213> ORGANISM: Pyrococcus furiosus

<400> SEQUENCE: 4

```
Met Ala Lys Phe Pro Lys Asn Phe Met Phe Gly Tyr Ser Trp Ser Gly
1               5                   10                  15

Phe Gln Phe Glu Met Gly Leu Pro Gly Ser Glu Val Glu Ser Asp Trp
            20                  25                  30

Trp Val Trp Val His Asp Lys Glu Asn Ile Ala Ser Gly Leu Val Ser
        35                  40                  45

Gly Asp Leu Pro Glu Asn Gly Pro Ala Tyr Trp His Leu Tyr Lys Gln
    50                  55                  60

Asp His Asp Ile Ala Glu Lys Leu Gly Met Asp Cys Ile Arg Gly Gly
65                  70                  75                  80

Ile Glu Trp Ala Arg Ile Phe Pro Lys Pro Thr Phe Asp Val Lys Val
                85                  90                  95

Asp Val Glu Lys Asp Glu Glu Gly Asn Ile Ile Ser Val Asp Val Pro
            100                 105                 110

Glu Ser Thr Ile Lys Glu Leu Glu Lys Ile Ala Asn Met Glu Ala Leu
        115                 120                 125

Glu His Tyr Arg Lys Ile Tyr Ser Asp Trp Lys Glu Arg Gly Lys Thr
    130                 135                 140

Phe Ile Leu Asn Leu Tyr His Trp Pro Leu Pro Leu Trp Ile His Asp
145                 150                 155                 160

Pro Ile Ala Val Arg Lys Leu Gly Pro Asp Arg Ala Pro Ala Gly Trp
                165                 170                 175

Leu Asp Glu Lys Thr Val Val Glu Phe Val Lys Phe Ala Ala Phe Val
            180                 185                 190

Ala Tyr His Leu Asp Asp Leu Val Asp Met Trp Ser Thr Met Asn Glu
        195                 200                 205

Pro Asn Val Val Tyr Asn Gln Gly Tyr Ile Asn Leu Arg Ser Gly Phe
    210                 215                 220

Pro Pro Gly Tyr Leu Ser Phe Glu Ala Ala Glu Lys Ala Lys Phe Asn
225                 230                 235                 240

Leu Ile Gln Ala His Ile Gly Ala Tyr Asp Ala Ile Lys Glu Tyr Ser
                245                 250                 255

Glu Lys Ser Val Gly Val Ile Tyr Ala Phe Ala Trp His Asp Pro Leu
            260                 265                 270
```

Ala Glu Glu Tyr Lys Asp Glu Val Glu Glu Ile Arg Lys Lys Asp Tyr
            275                 280                 285

Glu Phe Val Thr Ile Leu His Ser Lys Gly Lys Leu Asp Trp Ile Gly
            290                 295                 300

Val Asn Tyr Tyr Ser Arg Leu Val Tyr Gly Ala Lys Asp Gly His Leu
305                 310                 315                 320

Val Pro Leu Pro Gly Tyr Gly Phe Met Ser Glu Arg Gly Gly Phe Ala
                325                 330                 335

Lys Ser Gly Arg Pro Ala Ser Asp Phe Gly Trp Glu Met Tyr Pro Glu
            340                 345                 350

Gly Leu Glu Asn Leu Leu Lys Tyr Leu Asn Asn Ala Tyr Glu Leu Pro
            355                 360                 365

Met Ile Ile Thr Glu Asn Gly Met Ala Asp Ala Ala Asp Arg Tyr Arg
            370                 375                 380

Pro His Tyr Leu Val Ser His Leu Lys Ala Val Tyr Asn Ala Met Lys
385                 390                 395                 400

Glu Gly Ala Asp Val Arg Gly Tyr Leu His Trp Ser Leu Thr Asp Asn
                405                 410                 415

Tyr Glu Trp Ala Gln Gly Phe Arg Met Arg Phe Gly Leu Val Tyr Val
            420                 425                 430

Asp Phe Glu Thr Lys Lys Arg Tyr Leu Arg Pro Ser Ala Leu Val Phe
            435                 440                 445

Arg Glu Ile Ala Thr Gln Lys Glu Ile Pro Glu Glu Leu Ala His Leu
            450                 455                 460

Ala Asp Leu Lys Phe Val Thr Arg Lys
465                 470

<210> SEQ ID NO 5
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide encoding mutant beta-glucosidase
      having glycosylation site

<400> SEQUENCE: 5
atggcaaagt tcccaaaaaa cttcatgttt ggatattctt ggtctggttt ccagtttgag      60
atgggactgc aggaagtgaa gtggaaagcg actggtgggt gtgggttcac gacaaggag     120 aacatagcat caggtctagt aagtggagat ctaccagaga acggcccagc atattggaac    180
cgcactaagc aagatcatga cattgcagaa aagctaggaa tggattgtat tagaggtggc    240
attgagtggg caagaatttt tccaaagcca catttgacg ttaaagttga tgtggaaaag     300
gatgaagaag gcaacataat tccgtagac gttccagaga gtacaataaa agagctagag     360
aaaattgcca acatggaggc ccttgaacat tatcgcaaga tttactcaga ctggaaggag    420
aggggcaaaa ccttcatatt aaacctctac cactggcctc ttccattatg gattcatgac    480
ccaattgcag taaggaaact tggcccggat agggctcctg caggatggtt agatgagaag    540
acagtggtag agtttgtgaa gtttgccgcc ttcgttgctt atcaccttga tgacctcgtt    600
gacatgtgga gcacaatgaa cgaaccaaac gtagtctaca atcaaggtta cattaatcta    660
cgttcaggat ttccaccagg atatctaagc tttgaagcag cagaaaaggc aaaattcaac    720
ttaattcagg ctcacatcgg agcatatgat gccataaaag agtattcaga aaatccgtg     780 ggagtgatat acgcctttgc ttggcacgat cctctagcgg aggagtataa ggatgaagta    840

```
gaggaaatca gaaagaaaga ctatgagttt gtaacaattc tacactcaaa aggaaagcta    900
gactggatcg gcgtaaacta ctactccagg ctggtatatg gagccaaaga tggacaccta    960
gttcctttac ctggatatgg atttatgagt gagagaggag gatttgcaaa gtcaggaaga   1020
cctgctagtg actttggatg ggaaatgtac ccagagggcc ttgagaacct tcttaagtat   1080
ttaaacaatg cctacgagct accaatgata attacagaga acggtatggc cgatgcagca   1140
gatagataca ggccacacta tctcgtaagc catctaaagg cagtttacaa tgctatgaaa   1200
gaaggtgctg atgttagagg gtatctccac tggtctctaa cagacaacta cgaatgggcc   1260
caagggttca ggatgagatt tggattggtt tacgtggatt tcgagacaaa gaagagatat   1320
ttaaggccaa gcgccctggt attcagagaa atagccactc aaaaagaaat tccagaagaa   1380
ttagctcacc tcgcagacct caaatttgtt acaagaaag                          1419
```

<210> SEQ ID NO 6
<211> LENGTH: 473
<212> TYPE: PRT
<213> ORGANISM: Artificial Sequence
<220> FEATURE:
<223> OTHER INFORMATION: Description of Artificial Sequence: Synthetic
      mutant beta-glucosidase polypeptide having
      glycosylation site
<220> FEATURE:
<221> NAME/KEY: misc_feature
<222> LOCATION: (60)..(62)
<223> OTHER INFORMATION: CARBOHYD

<400> SEQUENCE: 6

```
Met Ala Lys Phe Pro Lys Asn Phe Met Phe Gly Tyr Ser Trp Ser Gly
1               5                   10                  15

Phe Gln Phe Glu Met Gly Leu Pro Gly Ser Glu Val Glu Ser Asp Trp
                20                  25                  30

Trp Val Trp Val His Asp Lys Glu Asn Ile Ala Ser Gly Leu Val Ser
            35                  40                  45

Gly Asp Leu Pro Glu Asn Gly Pro Ala Tyr Trp Asn Arg Thr Lys Gln
        50                  55                  60

Asp His Asp Ile Ala Glu Lys Leu Gly Met Asp Cys Ile Arg Gly Gly
    65                  70                  75                  80

Ile Glu Trp Ala Arg Ile Phe Pro Lys Pro Thr Phe Asp Val Lys Val
                85                  90                  95

Asp Val Glu Lys Asp Glu Glu Gly Asn Ile Ile Ser Val Asp Val Pro
            100                 105                 110

Glu Ser Thr Ile Lys Glu Leu Glu Lys Ile Ala Asn Met Glu Ala Leu
        115                 120                 125

Glu His Tyr Arg Lys Ile Tyr Ser Asp Trp Lys Glu Arg Gly Lys Thr
    130                 135                 140

Phe Ile Leu Asn Leu Tyr His Trp Pro Leu Pro Leu Trp Ile His Asp
145                 150                 155                 160

Pro Ile Ala Val Arg Lys Leu Gly Pro Asp Arg Ala Pro Ala Gly Trp
                165                 170                 175

Leu Asp Glu Lys Thr Val Val Glu Phe Val Lys Phe Ala Ala Phe Val
            180                 185                 190

Ala Tyr His Leu Asp Asp Leu Val Asp Met Trp Ser Thr Met Asn Glu
        195                 200                 205

Pro Asn Val Val Tyr Asn Gln Gly Tyr Ile Asn Leu Arg Ser Gly Phe
    210                 215                 220
```

```
Pro Pro Gly Tyr Leu Ser Phe Glu Ala Ala Glu Lys Ala Lys Phe Asn
225                 230                 235                 240

Leu Ile Gln Ala His Ile Gly Ala Tyr Asp Ala Ile Lys Glu Tyr Ser
            245                 250                 255

Glu Lys Ser Val Gly Val Ile Tyr Ala Phe Ala Trp His Asp Pro Leu
        260                 265                 270

Ala Glu Glu Tyr Lys Asp Glu Val Glu Glu Ile Arg Lys Lys Asp Tyr
    275                 280                 285

Glu Phe Val Thr Ile Leu His Ser Lys Gly Lys Leu Asp Trp Ile Gly
290                 295                 300

Val Asn Tyr Tyr Ser Arg Leu Val Tyr Gly Ala Lys Asp Gly His Leu
305                 310                 315                 320

Val Pro Leu Pro Gly Tyr Gly Phe Met Ser Glu Arg Gly Gly Phe Ala
                325                 330                 335

Lys Ser Gly Arg Pro Ala Ser Asp Phe Gly Trp Glu Met Tyr Pro Glu
            340                 345                 350

Gly Leu Glu Asn Leu Leu Lys Tyr Leu Asn Asn Ala Tyr Glu Leu Pro
        355                 360                 365

Met Ile Ile Thr Glu Asn Gly Met Ala Asp Ala Ala Asp Arg Tyr Arg
370                 375                 380

Pro His Tyr Leu Val Ser His Leu Lys Ala Val Tyr Asn Ala Met Lys
385                 390                 395                 400

Glu Gly Ala Asp Val Arg Gly Tyr Leu His Trp Ser Leu Thr Asp Asn
                405                 410                 415

Tyr Glu Trp Ala Gln Gly Phe Arg Met Arg Phe Gly Leu Val Tyr Val
            420                 425                 430

Asp Phe Glu Thr Lys Lys Arg Tyr Leu Arg Pro Ser Ala Leu Val Phe
        435                 440                 445

Arg Glu Ile Ala Thr Gln Lys Glu Ile Pro Glu Glu Leu Ala His Leu
    450                 455                 460

Ala Asp Leu Lys Phe Val Thr Arg Lys
465                 470

<210> SEQ ID NO 7
<211> LENGTH: 1446
<212> TYPE: DNA
<213> ORGANISM: Thermosphaera aggregans

<400> SEQUENCE: 7
atgaaattcc ccaaagactt catgataggc tactcatctt caccgtttca atttgaagct      60
ggtattcccg gtccgaggga tccgaatagt gattggtggg tatgggtgca tgatccggag     120
aacacagcag ctggactagt cagcggcgat tttcccgaga acggcccagg ttactgaat      180 ttaaaccaaa atgaccacga cctggctgag aagctggggg ttaacactat tagagtaggc     240
gttgagtgga gtaggatttt ccaaagcca actttcaatg ttaaagtccc tgtagagaga      300
gatgagaacg gcagcattgt tcacgtagat gtcgatgata agcggttga aagacttgat      360 gaattagcca acaaggaggc cgtaaaccat tacgtagaaa tgtataaaga ctgggttgaa     420
agaggtagaa aacttatact caatttatac cattggcccc tgcctctctg gcttcacaac     480
ccaatcatgg tgagaagaat gggcccggac agagcgccct caggctggct taacgaggag     540
tccgtggtgg agtttgccaa atacgccgca tacattgctt ggaaaatggg cgagctacct     600
gttatgtgga gcaccatgaa cgaacccaac gtcgtttatg agcaaggata catgttcgtt     660 aaaggggggtt tcccacccgg ctacttgagt ttggaagctg ctgataaggc caggagaaat     720
```

```
atgatccagg ctcatgcacg ggcctatgac aatattaaac gcttcagtaa gaaacctgtt    780
ggactaatat acgcttttcca atggttcgaa ctattagagg gtccagcaga agtatttgat    840
aagtttaaga gctctaagtt atactatttc acagacatag tatcgaaggg tagttcaatc    900
atcaatgttg aatacaggag agatcttgcc aataggctag actggttggg cgttaactac    960
tatagccgtt tagtctacaa aatcgtcgat gacaaaccta taatcctgca cgggtatgga   1020
ttcctttgta cacctggggg gatcagcccg gctgaaaatc cttgtagcga ttttgggtgg   1080
gaggtgtatc ctgaaggact ctacctactt ctaaaagaac tttacaaccg atacggggta   1140
gacttgatcg tgaccgagaa cggtgtttca gacagcaggg atgcgttgag accggcatac   1200
ctggtctcgc atgtttacag cgtatggaaa gccgctaacg agggcattcc cgtcaaaggc   1260
tacctccact ggagcttgac agacaattac gagtgggccc agggcttcag gcagaaattc   1320
ggtttagtca tggttgactt caaaactaag aaaaggtatc tccgcccaag cgccctagtg   1380
ttccgggaga tcgcaacgca taacggaata ccggatgagc tacagcatct tacactgatc   1440
cagtaa                                                               1446

<210> SEQ ID NO 8
<211> LENGTH: 481
<212> TYPE: PRT
<213> ORGANISM: Thermosphaera aggregans

<400> SEQUENCE: 8

Met Lys Phe Pro Lys Asp Phe Met Ile Gly Tyr Ser Ser Pro Phe
1               5                   10                  15

Gln Phe Glu Ala Gly Ile Pro Gly Ser Glu Asp Pro Asn Ser Asp Trp
            20                  25                  30

Trp Val Trp Val His Asp Pro Glu Asn Thr Ala Ala Gly Leu Val Ser
        35                  40                  45

Gly Asp Phe Pro Glu Asn Gly Pro Gly Tyr Trp Asn Leu Asn Gln Asn
    50                  55                  60

Asp His Asp Leu Ala Glu Lys Leu Gly Val Asn Thr Ile Arg Val Gly
65              70                  75                  80

Val Glu Trp Ser Arg Ile Phe Pro Lys Pro Thr Phe Asn Val Lys Val
            85                  90                  95

Pro Val Glu Arg Asp Glu Asn Gly Ser Ile Val His Val Asp Val Asp
        100                 105                 110

Asp Lys Ala Val Glu Arg Leu Asp Glu Leu Ala Asn Lys Glu Ala Val
    115                 120                 125

Asn His Tyr Val Glu Met Tyr Lys Asp Trp Val Glu Arg Gly Arg Lys
130             135                 140

Leu Ile Leu Asn Leu Tyr His Trp Pro Leu Pro Leu Trp Leu His Asn
145             150                 155                 160

Pro Ile Met Val Arg Arg Met Gly Pro Asp Arg Ala Pro Ser Gly Trp
            165                 170                 175

Leu Asn Glu Glu Ser Val Val Glu Phe Ala Lys Tyr Ala Ala Tyr Ile
        180                 185                 190

Ala Trp Lys Met Gly Glu Leu Pro Val Met Trp Ser Thr Met Asn Glu
    195                 200                 205

Pro Asn Val Val Tyr Glu Gln Gly Tyr Met Phe Val Lys Gly Gly Phe
210             215                 220

Pro Pro Gly Tyr Leu Ser Leu Glu Ala Ala Asp Lys Ala Arg Arg Asn
225             230                 235                 240
```

```
Met Ile Gln Ala His Ala Arg Ala Tyr Asp Asn Ile Lys Arg Phe Ser
                245                 250                 255
Lys Lys Pro Val Gly Leu Ile Tyr Ala Phe Gln Trp Phe Glu Leu Leu
            260                 265                 270
Glu Gly Pro Ala Glu Val Phe Asp Lys Phe Lys Ser Ser Lys Leu Tyr
        275                 280                 285
Tyr Phe Thr Asp Ile Val Ser Lys Gly Ser Ser Ile Ile Asn Val Glu
    290                 295                 300
Tyr Arg Arg Asp Leu Ala Asn Arg Leu Asp Trp Leu Gly Val Asn Tyr
305                 310                 315                 320
Tyr Ser Arg Leu Val Tyr Lys Ile Val Asp Asp Lys Pro Ile Ile Leu
                325                 330                 335
His Gly Tyr Gly Phe Leu Cys Thr Pro Gly Gly Ile Ser Pro Ala Glu
            340                 345                 350
Asn Pro Cys Ser Asp Phe Gly Trp Glu Val Tyr Pro Glu Gly Leu Tyr
        355                 360                 365
Leu Leu Leu Lys Glu Leu Tyr Asn Arg Tyr Gly Val Asp Leu Ile Val
    370                 375                 380
Thr Glu Asn Gly Val Ser Asp Ser Arg Asp Ala Leu Arg Pro Ala Tyr
385                 390                 395                 400
Leu Val Ser His Val Tyr Ser Val Trp Lys Ala Ala Asn Glu Gly Ile
                405                 410                 415
Pro Val Lys Gly Tyr Leu His Trp Ser Leu Thr Asp Asn Tyr Glu Trp
            420                 425                 430
Ala Gln Gly Phe Arg Gln Lys Phe Gly Leu Val Met Val Asp Phe Lys
        435                 440                 445
Thr Lys Lys Arg Tyr Leu Arg Pro Ser Ala Leu Val Phe Arg Glu Ile
    450                 455                 460
Ala Thr His Asn Gly Ile Pro Asp Glu Leu Gln His Leu Thr Leu Ile
465                 470                 475                 480
Gln

<210> SEQ ID NO 9
<211> LENGTH: 1461
<212> TYPE: DNA
<213> ORGANISM: Caldivirga maquilingensis

<400> SEQUENCE: 9
atgattaagt cccaagcga cttcagattc ggcttctcca cagtgggtac tcagcatgag        60
atgggtaccc ctggttctga attcgtaagt gactggtatg tgtggcttca tgaccctgag       120
aacattgctt cgggcttagt tagcggtgat ttacctgaac atgggccagg ttactgggac       180
ttgtataagc aggaccactc aatagctagg gatcttgggc ttgatgcagc atggataact       240
attgagtggg ctagggtgtt ccctaagccg acctttgacg ttaaggttaa ggttgatgag       300
gatgatggag gtaacgtggt tgacgttgag gttaatgaat cagcattaga ggagttacgc       360
aggctagctg acttaaatgc tgttaatcac tataggggga ttttaagtga ttggaaggag       420
agggggtggtt tactggtgat taacctttac cactgggcta tgcctacgtg gcttcatgac       480
ccaatagccg ttaggaagaa tggacctgat agagccccct ccggttggct tgataagaga       540
tccgttattg agttcactaa gttcgcagcc ttcatagccc atgagttagg tgacttagct       600
gacatgtggt atacgatgaa tgaacctggg gtagtgataa ctgagggtta cctttacgtt       660
aagtcaggct tcccaccagg ttacctggac ttaaactccc tagccactgc gggtaagcat       720
```

```
ttaattgagg ctcatgccag agcctacgac gccattaaag cctactcaag gaaaccagtg      780
ggcctagtct actccttcgc agactatcag ccgcttaggc agggtgatga ggaggctgtt      840
aaggaggcta agggacttga ctactcattc ttcgacgctc caattaaggg tgaattaatg      900
ggggttacta gggatgactt gaagggtagg cttgactgga ttggggtaaa ctactacact      960
agggccgtat tgaggaggag gcaggatgct ggtcgggcat cagtagccgt ggtggatgga     1020
ttcggctact cctgtgaacc tggaggcgta tctaatgata ggagaccatg cagtgacttc     1080
ggctgggaaa tataccctga gggtgtttac aatgtcttaa tggacctatg gaggaggtat     1140
aggatgccca tgtacatcac tgagaacggt atagctgatg agcatgataa gtggaggtca     1200
tggttcatag tatcgcacct gtatcaaatt cacagggcca tggaggaggg ggtggatgtt     1260
agagggtact ccactggaa cctaatagat aacttggagt gggctgcagg atataggatg     1320
aggttcggcc tagtttacgt tgactatgca accaagagga ggtattttag gccaagcgcc     1380
ctggttatga gggaggtggc taaacagaag gctataccgg attacttaga gcattacatt     1440
aaaccaccta gaattgaatg a                                                1461
```

<210> SEQ ID NO 10
<211> LENGTH: 486
<212> TYPE: PRT
<213> ORGANISM: Caldivirga maquilingensis

<400> SEQUENCE: 10

```
Met Ile Lys Phe Pro Ser Asp Phe Arg Phe Gly Phe Ser Thr Val Gly
1               5                   10                  15

Thr Gln His Glu Met Gly Thr Pro Gly Ser Glu Phe Val Ser Asp Trp
            20                  25                  30

Tyr Val Trp Leu His Asp Pro Glu Asn Ile Ala Ser Gly Leu Val Ser
        35                  40                  45

Gly Asp Leu Pro Glu His Gly Pro Gly Tyr Trp Asp Leu Tyr Lys Gln
    50                  55                  60

Asp His Ser Ile Ala Arg Asp Leu Gly Leu Asp Ala Ala Trp Ile Thr
65                  70                  75                  80

Ile Glu Trp Ala Arg Val Phe Pro Lys Pro Thr Phe Asp Val Lys Val
                85                  90                  95

Lys Val Asp Glu Asp Gly Gly Asn Val Val Asp Val Glu Val Asn
            100                 105                 110

Glu Ser Ala Leu Glu Glu Leu Arg Arg Leu Ala Asp Leu Asn Ala Val
        115                 120                 125

Asn His Tyr Arg Gly Ile Leu Ser Asp Trp Lys Glu Arg Gly Gly Leu
    130                 135                 140

Leu Val Ile Asn Leu Tyr His Trp Ala Met Pro Thr Trp Leu His Asp
145                 150                 155                 160

Pro Ile Ala Val Arg Lys Asn Gly Pro Asp Arg Ala Pro Ser Gly Trp
                165                 170                 175

Leu Asp Lys Arg Ser Val Ile Glu Phe Thr Lys Phe Ala Ala Phe Ile
            180                 185                 190

Ala His Glu Leu Gly Asp Leu Ala Asp Met Trp Tyr Thr Met Asn Glu
        195                 200                 205

Pro Gly Val Val Ile Thr Glu Gly Tyr Leu Tyr Val Lys Ser Gly Phe
    210                 215                 220

Pro Pro Gly Tyr Leu Asp Leu Asn Ser Leu Ala Thr Ala Gly Lys His
225                 230                 235                 240
```

```
Leu Ile Glu Ala His Ala Arg Ala Tyr Asp Ala Ile Lys Ala Tyr Ser
                245                 250                 255

Arg Lys Pro Val Gly Leu Val Tyr Ser Phe Ala Asp Tyr Gln Pro Leu
            260                 265                 270

Arg Gln Gly Asp Glu Glu Ala Val Lys Glu Ala Lys Gly Leu Asp Tyr
        275                 280                 285

Ser Phe Phe Asp Ala Pro Ile Lys Gly Glu Leu Met Gly Val Thr Arg
    290                 295                 300

Asp Asp Leu Lys Gly Arg Leu Asp Trp Ile Gly Val Asn Tyr Tyr Thr
305                 310                 315                 320

Arg Ala Val Leu Arg Arg Gln Asp Ala Gly Arg Ala Ser Val Ala
                325                 330                 335

Val Val Asp Gly Phe Gly Tyr Ser Cys Glu Pro Gly Gly Val Ser Asn
            340                 345                 350

Asp Arg Arg Pro Cys Ser Asp Phe Gly Trp Glu Ile Tyr Pro Glu Gly
        355                 360                 365

Val Tyr Asn Val Leu Met Asp Leu Trp Arg Arg Tyr Arg Met Pro Met
    370                 375                 380

Tyr Ile Thr Glu Asn Gly Ile Ala Asp Glu His Asp Lys Trp Arg Ser
385                 390                 395                 400

Trp Phe Ile Val Ser His Leu Tyr Gln Ile His Arg Ala Met Glu Glu
                405                 410                 415

Gly Val Asp Val Arg Gly Tyr Phe His Trp Asn Leu Ile Asp Asn Leu
            420                 425                 430

Glu Trp Ala Ala Gly Tyr Arg Met Arg Phe Gly Leu Val Tyr Val Asp
        435                 440                 445

Tyr Ala Thr Lys Arg Arg Tyr Phe Arg Pro Ser Ala Leu Val Met Arg
    450                 455                 460

Glu Val Ala Lys Gln Lys Ala Ile Pro Asp Tyr Leu Glu His Tyr Ile
465                 470                 475                 480

Lys Pro Pro Arg Ile Glu
                485

<210> SEQ ID NO 11
<211> LENGTH: 1476
<212> TYPE: DNA
<213> ORGANISM: Sulfolobus acidocaldarius

<400> SEQUENCE: 11
atgttatcat tcccaaaggg tttcaaattt ggctggtctc agtcgggatt ccagtctgaa       60
atgggaactc caggtagcga ggatccgaac agcgattggc acgtctgggt tcatgacagg      120
gagaacatag tctcacaggt tgtcagtgga gatttacccg aaaatggtcc agggtactgg      180 ggaactata agagatttca tgacgaagca gagaaaatag actaaatgc agtgagaatt        240 aacgtagagt gggtagaat atttcccaga ccactaccca agcctgaaat gcaaacaggg       300
actgataaag agaacagtcc tgtcattagc gtagacttaa atgagtctaa gctgagagaa      360
atggacaact acgctaatca tgaagcgtta tcacattaca ggcaaatact ggaggatcta      420
agaaacagag gatttcacat agtactgaac atgtatcatt ggactttgcc catatggttg      480
cacgacccta tcagagtgag gagaggagac tttacaggac caacaggttg gttaaactcc      540
aggacagttt atgagttcgc taggttctcg gcttacgtag cctggaaatt agatgatttg      600
gcgagtgaat atgcaacaat gaatgaacct aacgtggttt ggggagcagg ttacgctttt      660
```

```
cctagagcag gctttccacc taattacctt agcttcaggc tttcagaaat agctaaatgg    720
aatataattc aggctcatgc gagggcttat gacgccatca agagcgtatc aaaaaagagt    780
gtaggtataa tatatgcaaa cacatcatat tacccactca gaccacaaga taacgaagct    840
gtggaaatag cagagagatt gaacagatgg agtttctttg actccattat aaagggagag    900
ataactagtg agggacaaaa tgtcagagag gacttaagga acaggttaga ctggattggc    960
gtaaactatt acacgaggac tgtggtaaca aaagctgaga gtggttattt aacccttccg   1020
ggttatggag atcgttgtga aggaactca ttgagtttag ctaacctccc taccagtgat   1080
ttcggttggg agttctttcc tgagggtcta tatgatgtac ttttgaagta ttggaatagg   1140
tatgggttac cattatacgt aatggagaac ggtatcgctg atgacgctga ctaccaaaga   1200
ccgtattact tagtatcaca tatctaccag gtgcacaggg ctttaaacga gggagtagat   1260
gtaagaggtt atcttcattg gtctttggca gataattatg agtggtcgtc aggttttca   1320
atgaggttcg gtctacttaa ggtagattat ctaacaaaga gattgtactg gagaccttct   1380
gcattagttt acagggagat tactaggagt aacggtattc ctgaggagct ggaacatcta   1440
aacagagtac caccaataaa acctttgaga cattaa                              1476
```

<210> SEQ ID NO 12
<211> LENGTH: 491
<212> TYPE: PRT
<213> ORGANISM: Sulfolobus acidocaldarius

<400> SEQUENCE: 12

```
Met Leu Ser Phe Pro Lys Gly Phe Lys Phe Gly Trp Ser Gln Ser Gly
1               5                   10                  15

Phe Gln Ser Glu Met Gly Thr Pro Gly Ser Glu Asp Pro Asn Ser Asp
            20                  25                  30

Trp His Val Trp Val His Asp Arg Glu Asn Ile Val Ser Gln Val Val
        35                  40                  45

Ser Gly Asp Leu Pro Glu Asn Gly Pro Gly Tyr Trp Gly Asn Tyr Lys
    50                  55                  60

Arg Phe His Asp Glu Ala Glu Lys Ile Gly Leu Asn Ala Val Arg Ile
65                  70                  75                  80

Asn Val Glu Trp Ser Arg Ile Phe Pro Arg Pro Leu Pro Lys Pro Glu
                85                  90                  95

Met Gln Thr Gly Thr Asp Lys Glu Asn Ser Pro Val Ile Ser Val Asp
            100                 105                 110

Leu Asn Glu Ser Lys Leu Arg Glu Met Asp Asn Tyr Ala Asn His Glu
        115                 120                 125

Ala Leu Ser His Tyr Arg Gln Ile Leu Glu Asp Leu Arg Asn Arg Gly
    130                 135                 140

Phe His Ile Val Leu Asn Met Tyr His Trp Thr Leu Pro Ile Trp Leu
145                 150                 155                 160

His Asp Pro Ile Arg Val Arg Arg Gly Asp Phe Thr Gly Pro Thr Gly
                165                 170                 175

Trp Leu Asn Ser Arg Thr Val Tyr Glu Phe Ala Arg Phe Ser Ala Tyr
            180                 185                 190

Val Ala Trp Lys Leu Asp Asp Leu Ala Ser Glu Tyr Ala Thr Met Asn
        195                 200                 205

Glu Pro Asn Val Val Trp Gly Ala Gly Tyr Ala Phe Pro Arg Ala Gly
    210                 215                 220

Phe Pro Pro Asn Tyr Leu Ser Phe Arg Leu Ser Glu Ile Ala Lys Trp
```

```
                225                 230                 235                 240
Asn Ile Ile Gln Ala His Ala Arg Ala Tyr Asp Ala Ile Lys Ser Val
                245                 250                 255
Ser Lys Lys Ser Val Gly Ile Ile Tyr Ala Asn Thr Ser Tyr Tyr Pro
                260                 265                 270
Leu Arg Pro Gln Asp Asn Glu Ala Val Glu Ile Ala Glu Arg Leu Asn
                275                 280                 285
Arg Trp Ser Phe Phe Asp Ser Ile Ile Lys Gly Glu Ile Thr Ser Glu
                290                 295                 300
Gly Gln Asn Val Arg Glu Asp Leu Arg Asn Arg Leu Asp Trp Ile Gly
305                 310                 315                 320
Val Asn Tyr Tyr Thr Arg Thr Val Val Thr Lys Ala Glu Ser Gly Tyr
                325                 330                 335
Leu Thr Leu Pro Gly Tyr Gly Asp Arg Cys Glu Arg Asn Ser Leu Ser
                340                 345                 350
Leu Ala Asn Leu Pro Thr Ser Asp Phe Gly Trp Glu Phe Phe Pro Glu
                355                 360                 365
Gly Leu Tyr Asp Val Leu Leu Lys Tyr Trp Asn Arg Tyr Gly Leu Pro
                370                 375                 380
Leu Tyr Val Met Glu Asn Gly Ile Ala Asp Ala Asp Tyr Gln Arg
385                 390                 395                 400
Pro Tyr Tyr Leu Val Ser His Ile Tyr Gln Val His Arg Ala Leu Asn
                405                 410                 415
Glu Gly Val Asp Val Arg Gly Tyr Leu His Trp Ser Leu Ala Asp Asn
                420                 425                 430
Tyr Glu Trp Ser Ser Gly Phe Ser Met Arg Phe Gly Leu Leu Lys Val
                435                 440                 445
Asp Tyr Leu Thr Lys Arg Leu Tyr Trp Arg Pro Ser Ala Leu Val Tyr
                450                 455                 460
Arg Glu Ile Thr Arg Ser Asn Gly Ile Pro Glu Glu Leu Glu His Leu
465                 470                 475                 480
Asn Arg Val Pro Pro Ile Lys Pro Leu Arg His
                485                 490
```

<210> SEQ ID NO 13
<211> LENGTH: 1470
<212> TYPE: DNA
<213> ORGANISM: Sulfolobus solfataricus

<400> SEQUENCE: 13

```
atgtactcat tccaaatag ctttaggttt ggttggtccc aggccggatt tcaatcagaa      60
atgggaacac agggtcaga agatccaaat actgactggt ataaatgggt tcatgatcca     120
gaaaacatgg cagcgggatt agtaagtgga gatctaccag aaaatgggcc aggctactgg     180
ggaaactata agacatttca cgataatgca caaaaaatgg gattaaaaat agctagacta     240
aatgtggaat ggtctaggat atttcctaat ccattaccaa ggccacaaaa ctttgatgaa     300
tcaaaacaag atgtgacaga ggttgagata acgaaaacg agttaaagag acttgacgag     360
tacgctaata aagacgcatt aaaccattac agggaaatat tcaaggatct taaaagtaga     420
ggactttact ttatactaaa catgtatcat tggccattac ctctatggtt acacgaccca     480
ataagagtaa aagaggaga ttttactgga ccaagtggtt ggctaagtac tagaacagtt     540
tacgaattcg ctagattctc agcttatata gcttggaaat tcgatgatct agtggatgag     600
tactcaacaa tgaatgaacc taacgttgtt ggaggtttag atacgttggg tgttaagtcc     660
```

```
ggttttcccc caggatacct aagctttgaa ctttcccgta gggcaatgta taacatcatt      720
caagctcacg caagagcgta tgatgggata aagagtgttt ctaaaaaacc agttggaatt      780
atttacgcta atagctcatt ccagccgtta acggataaag atatggaagc ggtagagatg      840
gctgaaaatg ataatagatg gtggttcttt gatgctataa taagaggtga gatcaccaga      900
ggaaacgaga agattgtaag agatgaccta aagggtagat tggattggat tggagttaat      960
tattacacta ggactgttgt gaagaggact gaaaagggga cgttagcttt aggaggttac     1020
ggtcacggat gtgagaggaa ttctgtaagt ttagcgggat taccaaccag cgacttcggc     1080
tgggagttct tcccagaagg tttatatgac gttttgacga atactggaa tagatatcat      1140 ctctatatgt acgttactga aatggtatt gcggatgatg ccgattatca aaggccctat      1200
tatttagtat ctcacgttta tcaagttcat agagcaataa atagtggtgc agatgttaga     1260
gggtatttac attggtctct agctgataat tacgaatggg cttcaggatt ctctatgagg     1320
tttggtctgt taaggtcga ttacaacact aagagactat actggagacc ctcagcacta     1380
gtatataggg aaatcgccac aaatggcgca ataactgatg aaatagagca cttaaatagc     1440
gtacctccag taaagccatt aaggcactaa                                      1470
```

<210> SEQ ID NO 14
<211> LENGTH: 489
<212> TYPE: PRT
<213> ORGANISM: Sulfolobus solfataricus

<400> SEQUENCE: 14

```
Met Tyr Ser Phe Pro Asn Ser Phe Arg Phe Gly Trp Ser Gln Ala Gly
1               5                   10                  15

Phe Gln Ser Glu Met Gly Thr Pro Gly Ser Glu Asp Pro Asn Thr Asp
            20                  25                  30

Trp Tyr Lys Trp Val His Asp Pro Glu Asn Met Ala Ala Gly Leu Val
        35                  40                  45

Ser Gly Asp Leu Pro Glu Asn Gly Pro Gly Tyr Trp Gly Asn Tyr Lys
    50                  55                  60

Thr Phe His Asp Asn Ala Gln Lys Met Gly Leu Lys Ile Ala Arg Leu
65                  70                  75                  80

Asn Val Glu Trp Ser Arg Ile Phe Pro Asn Pro Leu Pro Arg Pro Gln
                85                  90                  95

Asn Phe Asp Glu Ser Lys Gln Asp Val Thr Glu Val Glu Ile Asn Glu
            100                 105                 110

Asn Glu Leu Lys Arg Leu Asp Glu Tyr Ala Asn Lys Asp Ala Leu Asn
        115                 120                 125

His Tyr Arg Glu Ile Phe Lys Asp Leu Lys Ser Arg Gly Leu Tyr Phe
    130                 135                 140

Ile Leu Asn Met Tyr His Trp Pro Leu Pro Leu Trp Leu His Asp Pro
145                 150                 155                 160

Ile Arg Val Arg Arg Gly Asp Phe Thr Gly Pro Ser Gly Trp Leu Ser
                165                 170                 175

Thr Arg Thr Val Tyr Glu Phe Ala Arg Phe Ser Ala Tyr Ile Ala Trp
            180                 185                 190

Lys Phe Asp Asp Leu Val Asp Glu Tyr Ser Thr Met Asn Glu Pro Asn
        195                 200                 205

Val Val Gly Gly Leu Gly Tyr Val Gly Val Lys Ser Gly Phe Pro Pro
    210                 215                 220
```

```
Gly Tyr Leu Ser Phe Glu Leu Ser Arg Arg Ala Met Tyr Asn Ile Ile
225                 230                 235                 240

Gln Ala His Ala Arg Ala Tyr Asp Gly Ile Lys Ser Val Ser Lys Lys
            245                 250                 255

Pro Val Gly Ile Ile Tyr Ala Asn Ser Ser Phe Gln Pro Leu Thr Asp
        260                 265                 270

Lys Asp Met Glu Ala Val Glu Met Ala Glu Asn Asp Asn Arg Trp Trp
    275                 280                 285

Phe Phe Asp Ala Ile Ile Arg Gly Glu Ile Thr Arg Gly Asn Glu Lys
290                 295                 300

Ile Val Arg Asp Asp Leu Lys Gly Arg Leu Asp Trp Ile Gly Val Asn
305                 310                 315                 320

Tyr Tyr Thr Arg Thr Val Val Lys Arg Thr Glu Lys Gly Tyr Val Ser
                325                 330                 335

Leu Gly Gly Tyr Gly His Gly Cys Glu Arg Asn Ser Val Ser Leu Ala
            340                 345                 350

Gly Leu Pro Thr Ser Asp Phe Gly Trp Glu Phe Phe Pro Glu Gly Leu
        355                 360                 365

Tyr Asp Val Leu Thr Lys Tyr Trp Asn Arg Tyr His Leu Tyr Met Tyr
370                 375                 380

Val Thr Glu Asn Gly Ile Ala Asp Asp Ala Asp Tyr Gln Arg Pro Tyr
385                 390                 395                 400

Tyr Leu Val Ser His Val Tyr Gln Val His Arg Ala Ile Asn Ser Gly
                405                 410                 415

Ala Asp Val Arg Gly Tyr Leu His Trp Ser Leu Ala Asp Asn Tyr Glu
            420                 425                 430

Trp Ala Ser Gly Phe Ser Met Arg Phe Gly Leu Leu Lys Val Asp Tyr
        435                 440                 445

Asn Thr Lys Arg Leu Tyr Trp Arg Pro Ser Ala Leu Val Tyr Arg Glu
    450                 455                 460

Ile Ala Thr Asn Gly Ala Ile Thr Asp Glu Ile Glu His Leu Asn Ser
465                 470                 475                 480

Val Pro Pro Val Lys Pro Leu Arg His
                485

<210> SEQ ID NO 15
<211> LENGTH: 1488
<212> TYPE: DNA
<213> ORGANISM: Picrophilus torridus

<400> SEQUENCE: 15
atgttaccca agaacttttt acttggcttt tctctggctg gctttcagtc tgaaatgggc      60
atatcagatc ctgatagcaa ttcagattgg tggttatggg tacatgaccc ggtgaatata     120
aggactggac ttgtatctgg tgacttacct gaaaatggaa taggatactg ggatctttac     180
aaaaaatata atggtctggc tgttcaaaca ggaatgaatg ctgcaaggct tggagttgaa     240
tggagcagga tatttccaaa aagtactgaa gaagtaaagg tgatggaaga ttacaaagat     300
gatgatttaa tttccgtgga tgttaatgag ggaagtcttg aaaaacttga cagactggca     360
aatcaaaagg caattaatag atatatggaa atcttcaata atatcaagga aaataatatg     420
acgctaatag tgaatgttta ccattggcca ataccaatat atcttcacga tccaatagaa     480
gctaggaata gtggactttc aaataaaaga aatggctggc ttaatcataa aaccgttgtg     540
gaatttgtaa aatatgcaaa atatctggca tggaaattta gcgatgtggc agatatgttt     600
```

-continued

```
tctataatga atgagccaaa cgttgtattt ggtaatggat attttaatgt taaatcaggg    660
ttcccaccag catttccaag tgtgcatggc ggtttgcttg caaaaaaaca tgaaattgag    720
gctatagcaa gatcatacga cgccatgaag gagattacaa aaaaccagt tggtctaatt    780
atggcaaatt cagatgtaca accactaaca gatgaggata agaagcagc agaaatggct    840
acttacaatg atcgctattc attcatagat ccgctaagag ttggtgagat gaaatgggct    900
gatgaggtta ctgcaggtaa tccaattggt gaaagagca acatcgatag atctgatcta    960
aaaaataagc tagactggat aggtgttaac tattatacaa gggccgttgt aaaaaaatct   1020
ggaaacggat atacaacatt aaaaggatat ggacactctg caaccgctgg catgccaagt   1080
agggccggaa gggatgtaag tgactttggc tgggaattct atccagaagg tcttgtaaac   1140
gtcttatcat catactggaa aagatatcac attccaatga ttgtgactga aaatggtgtt   1200
gctgactcta ttgatagact tagaccaagg taccttgtgt cacatataaa gtctgttgaa   1260
aaggctttat ctatgggtat ggatattagg ggatatcttc actggtctct gattgataac   1320
tatgaatggg catcaggttt ttcaatgaaa tttgggcttt atggtattga tttgaacaat   1380
aaaaagattc aacacagacc aagtgcactg gtatttaaag aaattgcaaa tgccaacgga   1440
gtcccggagg aatttgaatg gatggcagac cagcatcaga attcatga                1488
```

<210> SEQ ID NO 16
<211> LENGTH: 495
<212> TYPE: PRT
<213> ORGANISM: Picrophilus torridus

<400> SEQUENCE: 16

```
Met Leu Pro Lys Asn Phe Leu Gly Phe Ser Leu Ala Gly Phe Gln
1               5                   10                  15

Ser Glu Met Gly Ile Ser Asp Pro Asp Ser Asn Ser Asp Trp Trp Leu
            20                  25                  30

Trp Val His Asp Pro Val Asn Ile Arg Thr Gly Leu Val Ser Gly Asp
        35                  40                  45

Leu Pro Glu Asn Gly Ile Gly Tyr Trp Asp Leu Tyr Lys Lys Tyr Asn
    50                  55                  60

Gly Leu Ala Val Gln Thr Gly Met Asn Ala Ala Arg Leu Gly Val Glu
65                  70                  75                  80

Trp Ser Arg Ile Phe Pro Lys Ser Thr Glu Glu Val Lys Val Met Glu
                85                  90                  95

Asp Tyr Lys Asp Asp Asp Leu Ile Ser Val Asp Val Asn Glu Gly Ser
            100                 105                 110

Leu Glu Lys Leu Asp Arg Leu Ala Asn Gln Lys Ala Ile Asn Arg Tyr
        115                 120                 125

Met Glu Ile Phe Asn Asn Ile Lys Glu Asn Asn Met Thr Leu Ile Val
    130                 135                 140

Asn Val Tyr His Trp Pro Ile Pro Ile Tyr Leu His Asp Pro Ile Glu
145                 150                 155                 160

Ala Arg Asn Ser Gly Leu Ser Asn Lys Arg Asn Gly Trp Leu Asn His
                165                 170                 175

Lys Thr Val Val Glu Phe Val Lys Tyr Ala Lys Tyr Leu Ala Trp Lys
            180                 185                 190

Phe Ser Asp Val Ala Asp Met Phe Ser Ile Met Asn Glu Pro Asn Val
        195                 200                 205

Val Phe Gly Asn Gly Tyr Phe Asn Val Lys Ser Gly Phe Pro Pro Ala
    210                 215                 220
```

```
Phe Pro Ser Val His Gly Gly Leu Leu Ala Lys Lys His Glu Ile Glu
225                 230                 235                 240

Ala Ile Ala Arg Ser Tyr Asp Ala Met Lys Glu Ile Thr Lys Lys Pro
            245                 250                 255

Val Gly Leu Ile Met Ala Asn Ser Asp Val Gln Pro Leu Thr Asp Glu
        260                 265                 270

Asp Lys Glu Ala Ala Glu Met Ala Thr Tyr Asn Asp Arg Tyr Ser Phe
    275                 280                 285

Ile Asp Pro Leu Arg Val Gly Glu Met Lys Trp Ala Asp Glu Val Thr
290                 295                 300

Ala Gly Asn Pro Ile Gly Glu Lys Ser Asn Ile Asp Arg Ser Asp Leu
305                 310                 315                 320

Lys Asn Lys Leu Asp Trp Ile Gly Val Asn Tyr Tyr Thr Arg Ala Val
            325                 330                 335

Val Lys Lys Ser Gly Asn Gly Tyr Thr Thr Leu Lys Gly Tyr Gly His
        340                 345                 350

Ser Ala Thr Ala Gly Met Pro Ser Arg Ala Gly Arg Asp Val Ser Asp
    355                 360                 365

Phe Gly Trp Glu Phe Tyr Pro Glu Gly Leu Val Asn Val Leu Ser Ser
370                 375                 380

Tyr Trp Lys Arg Tyr His Ile Pro Met Ile Val Thr Glu Asn Gly Val
385                 390                 395                 400

Ala Asp Ser Ile Asp Arg Leu Arg Pro Arg Tyr Leu Val Ser His Ile
            405                 410                 415

Lys Ser Val Glu Lys Ala Leu Ser Met Gly Met Asp Ile Arg Gly Tyr
        420                 425                 430

Leu His Trp Ser Leu Ile Asp Asn Tyr Glu Trp Ala Ser Gly Phe Ser
    435                 440                 445

Met Lys Phe Gly Leu Tyr Gly Ile Asp Leu Asn Asn Lys Lys Ile Gln
450                 455                 460

His Arg Pro Ser Ala Leu Val Phe Lys Glu Ile Ala Asn Ala Asn Gly
465                 470                 475                 480

Val Pro Glu Glu Phe Glu Trp Met Ala Asp Gln His Gln Asn Ser
            485                 490                 495

<210> SEQ ID NO 17
<211> LENGTH: 1446
<212> TYPE: DNA
<213> ORGANISM: Thermoplasma volcanium

<400> SEQUENCE: 17
atggtagaaa acaattttcc agaggatttc aaattttggtt ggtcacagtc aggttttcaa      60
tcggagatgg gctatgataa cgcaatggac gataaaagtg actggtatgt ctgggttcat     120
gataaagaaa acatccaatc agggcttgta agcggagaca tgcccgaaaa tggtccgggt     180
tactggaata actataaatc attccatgaa gctgcacaga atatgggatt aaaaatggca     240
agaatcggag ttgaatggtc aagattattc ccggaacctt tcccggaaaa ataatggca      300 gatgcaaaaa ataattcctt agaaataaac aataacattc tttcagaact tgataaatat     360
gtcaataaag atgcactcaa ccattacatt gagatattta tgatatcaa aaatagaaat      420 atagatttaa taattaatat gtaccactgg ccacttcctg tatggctaag cgatcctgta     480
tctgttagaa aaggaataaa aacagaaaga tcaggctggc tgaatgacag gatagttcaa     540
ttgtttgctt tattctcctc gtatatagta tataaaatgg aagatctggc agttgcattt     600
```

```
tcaaccatga atgaacctaa tgttgtttat ggaaatggtt ttataaatat caaatcaggt      660
tttccgcctt cctatctcag ttcagaattt gcatctaaag ttaagaacaa tatattaaaa      720
gcacattctc ttgcatacga ttctatgaaa aaaattacgg ataaacctgt gggaataatt      780
tatgcaaaca catattttac gcctttggat ccggaaaaag ataatgatgc tattgctaaa      840
gcagacagtg atgcgaaatg gtcattttt gatccattaa taaaggaga taaatcactt       900
ggaattaatg gcaataaact agattggatc ggaattaatt attatacaag gacaatgtta      960
aggaaagacg gagatggcta tatttcatta aaaggctatg gtcattcagg ttctcctaat     1020
actgtaacaa cgataaaag accaacaagt gatataggat gggaattcta tccggaggga     1080
ttggaatatg taattatgaa ttactggaac aggtataaat tgcctatgta cgtaacagaa     1140
aatggcatag ccgataatgg ggattatcag aggccttatt atttagtttc acacattgca     1200
agtgtactga gggcaataaa taaggagcc aatgtaaagg gttatttgca ctggtcctta      1260
gttgataatt atgaatgggc attgggattt agcccgaaat ttggtttaat aggatacgat     1320
gaaaataaaa aactatactg gaggccaagt gctcttgttt ataaggaaat agcaacaaaa     1380
aattgcatat ccccagaatt aaagcacctc gattcaatac cgcctataaa tggtttaaga     1440
aaataa                                                                 1446

<210> SEQ ID NO 18
<211> LENGTH: 481
<212> TYPE: PRT
<213> ORGANISM: Thermoplasma volcanium

<400> SEQUENCE: 18

Met Val Glu Asn Asn Phe Pro Glu Asp Phe Lys Phe Gly Trp Ser Gln
1               5                   10                  15

Ser Gly Phe Gln Ser Glu Met Gly Tyr Asp Asn Ala Met Asp Asp Lys
                20                  25                  30

Ser Asp Trp Tyr Val Trp Val His Asp Lys Glu Asn Ile Gln Ser Gly
            35                  40                  45

Leu Val Ser Gly Asp Met Pro Glu Asn Gly Pro Gly Tyr Trp Asn Asn
        50                  55                  60

Tyr Lys Ser Phe His Glu Ala Ala Gln Asn Met Gly Leu Lys Met Ala
65                  70                  75                  80

Arg Ile Gly Val Glu Trp Ser Arg Leu Phe Pro Glu Pro Phe Pro Glu
                85                  90                  95

Lys Ile Met Ala Asp Ala Lys Asn Asn Ser Leu Glu Ile Asn Asn Asn
                100                 105                 110

Ile Leu Ser Glu Leu Asp Lys Tyr Val Asn Lys Asp Ala Leu Asn His
            115                 120                 125

Tyr Ile Glu Ile Phe Asn Asp Ile Lys Asn Arg Asn Ile Asp Leu Ile
        130                 135                 140

Ile Asn Met Tyr His Trp Pro Leu Pro Val Trp Leu Ser Asp Pro Val
145                 150                 155                 160

Ser Val Arg Lys Gly Ile Lys Thr Glu Arg Ser Gly Trp Leu Asn Asp
                165                 170                 175

Arg Ile Val Gln Leu Phe Ala Leu Phe Ser Ser Tyr Ile Val Tyr Lys
            180                 185                 190

Met Glu Asp Leu Ala Val Ala Phe Ser Thr Met Asn Glu Pro Asn Val
        195                 200                 205

Val Tyr Gly Asn Gly Phe Ile Asn Ile Lys Ser Gly Phe Pro Pro Ser
```

```
        210             215                 220
Tyr Leu Ser Ser Glu Phe Ala Ser Lys Val Lys Asn Ile Leu Lys
225                 230                 235                 240

Ala His Ser Leu Ala Tyr Asp Ser Met Lys Lys Ile Thr Asp Lys Pro
                245                 250                 255

Val Gly Ile Ile Tyr Ala Asn Thr Tyr Phe Thr Pro Leu Asp Pro Glu
            260                 265                 270

Lys Asp Asn Asp Ala Ile Ala Lys Ala Asp Ser Asp Ala Lys Trp Ser
                275                 280                 285

Phe Phe Asp Pro Leu Ile Lys Gly Asp Lys Ser Leu Gly Ile Asn Gly
        290                 295                 300

Asn Lys Leu Asp Trp Ile Gly Ile Asn Tyr Tyr Thr Arg Thr Met Leu
305                 310                 315                 320

Arg Lys Asp Gly Asp Gly Tyr Ile Ser Leu Lys Gly Tyr Gly His Ser
                325                 330                 335

Gly Ser Pro Asn Thr Val Thr Asn Asp Lys Arg Pro Thr Ser Asp Ile
                340                 345                 350

Gly Trp Glu Phe Tyr Pro Glu Gly Leu Glu Tyr Val Ile Met Asn Tyr
            355                 360                 365

Trp Asn Arg Tyr Lys Leu Pro Met Tyr Val Thr Glu Asn Gly Ile Ala
        370                 375                 380

Asp Asn Gly Asp Tyr Gln Arg Pro Tyr Tyr Leu Val Ser His Ile Ala
385                 390                 395                 400

Ser Val Leu Arg Ala Ile Asn Lys Gly Ala Asn Val Lys Gly Tyr Leu
                405                 410                 415

His Trp Ser Leu Val Asp Asn Tyr Glu Trp Ala Leu Gly Phe Ser Pro
            420                 425                 430

Lys Phe Gly Leu Ile Gly Tyr Asp Glu Asn Lys Lys Leu Tyr Trp Arg
        435                 440                 445

Pro Ser Ala Leu Val Tyr Lys Glu Ile Ala Thr Lys Asn Cys Ile Ser
            450                 455                 460

Pro Glu Leu Lys His Leu Asp Ser Ile Pro Pro Ile Asn Gly Leu Arg
465                 470                 475                 480

Lys

<210> SEQ ID NO 19
<211> LENGTH: 1404
<212> TYPE: DNA
<213> ORGANISM: Fervidobacterium nodosum

<400> SEQUENCE: 19
atgatgtttc cgaaagattt tttatttggt gtttcgatgt ctgggtttca gtttgagatg      60
ggaaatcctc aagatgcaga agaggttgat ctaaatacag attggtatgt atgggttagg     120
gatattggaa atattgtaaa tggagtcgta agtggggact tgcctgaaaa tggttcatgg     180
tactggaagc agtacggcaa agtccaccaa ttagctgccg attttgggat ggatgtaata     240
cgaattggaa ccgaatggtc taggattttc ccagttagta cgcaaagtgt tgagtacggc     300
tcaccggata tgctcgaaaa attggataaa ttagcaaacc aaaaagcggt aagtcattac     360
aggaaaataa tggaggatat aaaagcaaag gggttaaaat tgttcgttaa cctttaccac     420
tttactttac ctatttggtt gcacgaccct atagctgttc acaaaggtga agacagat      480 aaaattggtt ggatttctga tgctacacct attgagtttg cgaagtatgc agagtacatg     540
gcgtggaaat tgccgatat agttgatatg tgggcttcta tgaacgaacc acacgttgta     600
```

-continued

```
agtcagcttg gatattttgc aataaatgcg ggatttccac caagttattt taatccttca    660
tggtatatca aaagtttaga aaacgaagcg aaagcacata acttatctta tgatgctata    720
aaaaagtata caataatcc tgttggagtt atatactctt ttacatggta cgatactgtt    780
aataaagatg acaaggaatc ttttgaaaat gctatggatc tcacaaattg gcgatttata    840
gatatggtaa agataaaac tgattacata ggtgtaaatt attacacaag agcggttatc    900
gatagacttc ccaccactat tgactttggc gaatttaaaa tgaattggta tactttgaga    960
ggttacggtt attcttgcga agaaggagga ttctcactct ccggaaggcc ggcaagcgaa   1020
tttggatggg aaatataccc tgaagggctg tacaatattt tgatacatgt ttataataga   1080
tacaaaaaag atatttatgt tacggagaac ggtatagctg attcgaagga taaatacaga   1140
agtctttttta tcatatcgca tctttatgct atagaaaaag cattaaacga aggaatacca   1200
ataaaaggtt atttgcactg gtcgattata gacaatttcg aatgggcgaa gggctacagt   1260
aaaagatttg gacttgctta cacagatttg tcaaccaaaa aatatatacc tagaccttct   1320
atgtacattt ttagagagat aataaaggat aaatcaatcg acaaattcaa aggttacgat   1380
ccatataact tgatgaaatt ctga                                          1404
```

<210> SEQ ID NO 20
<211> LENGTH: 467
<212> TYPE: PRT
<213> ORGANISM: Fervidobacterium nodosum

<400> SEQUENCE: 20

```
Met Met Phe Pro Lys Asp Phe Leu Phe Gly Val Ser Met Ser Gly Phe
  1               5                  10                  15

Gln Phe Glu Met Gly Asn Pro Gln Asp Ala Glu Glu Val Asp Leu Asn
             20                  25                  30

Thr Asp Trp Tyr Val Trp Val Arg Asp Ile Gly Asn Ile Val Asn Gly
         35                  40                  45

Val Val Ser Gly Asp Leu Pro Glu Asn Gly Ser Trp Tyr Trp Lys Gln
     50                  55                  60

Tyr Gly Lys Val His Gln Leu Ala Ala Asp Phe Gly Met Asp Val Ile
 65                  70                  75                  80

Arg Ile Gly Thr Glu Trp Ser Arg Ile Phe Pro Val Ser Thr Gln Ser
                 85                  90                  95

Val Glu Tyr Gly Ser Pro Asp Met Leu Glu Lys Leu Asp Lys Leu Ala
            100                 105                 110

Asn Gln Lys Ala Val Ser His Tyr Arg Lys Ile Met Glu Asp Ile Lys
        115                 120                 125

Ala Lys Gly Leu Lys Leu Phe Val Asn Leu Tyr His Phe Thr Leu Pro
    130                 135                 140

Ile Trp Leu His Asp Pro Ile Ala Val His Lys Gly Glu Lys Thr Asp
145                 150                 155                 160

Lys Ile Gly Trp Ile Ser Asp Ala Thr Pro Ile Glu Phe Ala Lys Tyr
                165                 170                 175

Ala Glu Tyr Met Ala Trp Lys Phe Ala Asp Ile Val Asp Met Trp Ala
            180                 185                 190

Ser Met Asn Glu Pro His Val Val Ser Gln Leu Gly Tyr Phe Ala Ile
        195                 200                 205

Asn Ala Gly Phe Pro Pro Ser Tyr Phe Asn Pro Ser Trp Tyr Ile Lys
    210                 215                 220
```

Ser Leu Glu Asn Glu Ala Lys Ala His Asn Leu Ser Tyr Asp Ala Ile
225                 230                 235                 240

Lys Lys Tyr Thr Asn Asn Pro Val Gly Val Ile Tyr Ser Phe Thr Trp
            245                 250                 255

Tyr Asp Thr Val Asn Lys Asp Asp Lys Glu Ser Phe Glu Asn Ala Met
        260                 265                 270

Asp Leu Thr Asn Trp Arg Phe Ile Asp Met Val Lys Asp Lys Thr Asp
    275                 280                 285

Tyr Ile Gly Val Asn Tyr Tyr Thr Arg Ala Val Ile Asp Arg Leu Pro
290                 295                 300

Thr Thr Ile Asp Phe Gly Glu Phe Lys Met Asn Trp Tyr Thr Leu Arg
305                 310                 315                 320

Gly Tyr Gly Tyr Ser Cys Glu Glu Gly Phe Ser Leu Ser Gly Arg
                325                 330                 335

Pro Ala Ser Glu Phe Gly Trp Glu Ile Tyr Pro Glu Gly Leu Tyr Asn
            340                 345                 350

Ile Leu Ile His Val Tyr Asn Arg Tyr Lys Lys Asp Ile Tyr Val Thr
        355                 360                 365

Glu Asn Gly Ile Ala Asp Ser Lys Asp Lys Tyr Arg Ser Leu Phe Ile
370                 375                 380

Ile Ser His Leu Tyr Ala Ile Glu Lys Ala Leu Asn Glu Gly Ile Pro
385                 390                 395                 400

Ile Lys Gly Tyr Leu His Trp Ser Ile Ile Asp Asn Phe Glu Trp Ala
                405                 410                 415

Lys Gly Tyr Ser Lys Arg Phe Gly Leu Ala Tyr Thr Asp Leu Ser Thr
            420                 425                 430

Lys Lys Tyr Ile Pro Arg Pro Ser Met Tyr Ile Phe Arg Glu Ile Ile
        435                 440                 445

Lys Asp Lys Ser Ile Asp Lys Phe Lys Gly Tyr Asp Pro Tyr Asn Leu
450                 455                 460

Met Lys Phe
465

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccacatattg gcacctctat aagcaagatc atg                                33

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
catgatcttg cttagtgcgg ttccaatatg ctgg                               34

<210> SEQ ID NO 23
<211> LENGTH: 1446
<212> TYPE: DNA
<213> ORGANISM: Thermosphaera aggregans

<400> SEQUENCE: 23

```
atgggtaaat tccccaaaga cttcatgata ggctactcat cttcaccgtt tcaatttgaa      60
gctggtattc ccgggtccga agatccgaat agtgattggt gggtatgggt gcatgatccg     120
gagaacacag cagctggact agtcagcggc gattttcccg agaacggccc aggttactgg     180
aatttaaacc aaaatgacca cgacctggct gagaagctgg gggttaacac tattagagta     240
ggcgttgagt ggagtaggat ttttccaaag ccaactttca atgttaaagt ccctgtagag     300
agagatgaga acggcagcat tgttcacgta gatgtcgatg ataaagcggt tgaaagactt     360
gatgaattag ccaacaagga ggccgtaaac cattacgtag aaatgtataa agactgggtt     420
gaaagaggta gaaaacttat actcaattta taccattggc ccctgcctct ctggcttcac     480
aacccaatca tggtgagaag aatgggcccg gacagagcgc cctcaggctg cttaacgag      540
gagtccgtgg tggagtttgc caaatacgcc gcatacattg cttggaaaat gggcgagcta     600
cctgttatgt ggagcaccat gaacgaaccc aacgtcgttt atgagcaagg atacatgttc     660
gttaaagggg gtttcccacc cggctacttg agtttggaag ctgctgataa ggccaggaga     720
aatatgatcc aggctcatgc acgggcctat gacaatatta aacgcttcag taagaaacct     780
gttggactaa tatacgcttt ccaatggttc gaactattag agggtccagc agaagtattt     840
gataagttta gagctctaa gttatactat ttcacagaca tagtatcgaa gggtagttca     900
atcatcaatg ttgaatacag gagagatctt gccaataggc tagactggtt gggcgttaac     960
tactatagcc gtttagtcta caaaatcgtc gatgacaaac ctataatcct gcacgggtat    1020
ggattccttt gtacacctgg ggggatcagc ccggctgaaa tccttgtag cgattttggg    1080
tgggaggtgt atcctgaagg actctaccta cttctaaaag aactttacaa ccgatacggg    1140
gtagacttga tcgtgaccga gaacggtgtt tcagacagca gggatgcgtt gagaccggca    1200
tacctggtct cgcatgttta cagcgtatgg aaagccgcta acgagggcat tcccgtcaaa    1260
ggctacctcc actggagctt gacagacaat tacgagtggg cccagggctt caggcagaaa    1320
ttcggtttag tcatggttga cttcaaaact aagaaaaggt atctccgccc aagcgcccta    1380
gtgttccggg agatcgcaac gcataacgga ataccggatg agctacagca tcttacactg    1440
atccag                                                                1446
```

<210> SEQ ID NO 24
<211> LENGTH: 482
<212> TYPE: PRT
<213> ORGANISM: Thermosphaera aggregans

<400> SEQUENCE: 24

```
Met Gly Lys Phe Pro Lys Asp Phe Met Ile Gly Tyr Ser Ser Pro
1               5                   10                  15

Phe Gln Phe Glu Ala Gly Ile Pro Gly Ser Glu Asp Pro Asn Ser Asp
            20                  25                  30

Trp Trp Val Trp Val His Asp Pro Glu Asn Thr Ala Ala Gly Leu Val
        35                  40                  45

Ser Gly Asp Phe Pro Glu Asn Gly Pro Gly Tyr Trp Asn Leu Asn Gln
    50                  55                  60

Asn Asp His Asp Leu Ala Glu Lys Leu Gly Val Asn Thr Ile Arg Val
65                  70                  75                  80

Gly Val Glu Trp Ser Arg Ile Phe Pro Lys Pro Thr Phe Asn Val Lys
                85                  90                  95
```

```
Val Pro Val Glu Arg Asp Glu Asn Gly Ser Ile Val His Val Asp Val
            100                 105                 110

Asp Asp Lys Ala Val Glu Arg Leu Asp Glu Leu Ala Asn Lys Glu Ala
        115                 120                 125

Val Asn His Tyr Val Glu Met Tyr Lys Asp Trp Val Glu Arg Gly Arg
    130                 135                 140

Lys Leu Ile Leu Asn Leu Tyr His Trp Pro Leu Pro Leu Trp Leu His
145                 150                 155                 160

Asn Pro Ile Met Val Arg Arg Met Gly Pro Asp Arg Ala Pro Ser Gly
                165                 170                 175

Trp Leu Asn Glu Glu Ser Val Val Glu Phe Ala Lys Tyr Ala Ala Tyr
            180                 185                 190

Ile Ala Trp Lys Met Gly Glu Leu Pro Val Met Trp Ser Thr Met Asn
        195                 200                 205

Glu Pro Asn Val Val Tyr Glu Gln Gly Tyr Met Phe Val Lys Gly Gly
    210                 215                 220

Phe Pro Pro Gly Tyr Leu Ser Leu Glu Ala Ala Asp Lys Ala Arg Arg
225                 230                 235                 240

Asn Met Ile Gln Ala His Ala Arg Ala Tyr Asp Asn Ile Lys Arg Phe
                245                 250                 255

Ser Lys Lys Pro Val Gly Leu Ile Tyr Ala Phe Gln Trp Phe Glu Leu
            260                 265                 270

Leu Glu Gly Pro Ala Glu Val Phe Asp Lys Phe Lys Ser Ser Lys Leu
        275                 280                 285

Tyr Tyr Phe Thr Asp Ile Val Ser Lys Gly Ser Ser Ile Ile Asn Val
    290                 295                 300

Glu Tyr Arg Arg Asp Leu Ala Asn Arg Leu Asp Trp Leu Gly Val Asn
305                 310                 315                 320

Tyr Tyr Ser Arg Leu Val Tyr Lys Ile Val Asp Asp Lys Pro Ile Ile
                325                 330                 335

Leu His Gly Tyr Gly Phe Leu Cys Thr Pro Gly Gly Ile Ser Pro Ala
            340                 345                 350

Glu Asn Pro Cys Ser Asp Phe Gly Trp Glu Val Tyr Pro Glu Gly Leu
        355                 360                 365

Tyr Leu Leu Lys Glu Leu Tyr Asn Arg Tyr Gly Val Asp Leu Ile
    370                 375                 380

Val Thr Glu Asn Gly Val Ser Asp Ser Arg Asp Ala Leu Arg Pro Ala
385                 390                 395                 400

Tyr Leu Val Ser His Val Tyr Ser Val Trp Lys Ala Ala Asn Glu Gly
                405                 410                 415

Ile Pro Val Lys Gly Tyr Leu His Trp Ser Leu Thr Asp Asn Tyr Glu
            420                 425                 430

Trp Ala Gln Gly Phe Arg Gln Lys Phe Gly Leu Val Met Val Asp Phe
        435                 440                 445

Lys Thr Lys Lys Arg Tyr Leu Arg Pro Ser Ala Leu Val Phe Arg Glu
    450                 455                 460

Ile Ala Thr His Asn Gly Ile Pro Asp Glu Leu Gln His Leu Thr Leu
465                 470                 475                 480

Ile Gln

<210> SEQ ID NO 25
<211> LENGTH: 1461
<212> TYPE: DNA
<213> ORGANISM: Caldivirga maquilingensis
```

<400> SEQUENCE: 25

```
atgggtatta agttcccaag cgacttcaga ttcggcttct ccacagtggg tactcagcat    60
gagatgggta cccctggttc tgaatttgta agtgactggt atgtgtggct tcatgaccct   120
gagaacattg cttcgggctt agttagcggt gatttacctg aacatgggcc aggttactgg   180
gacttgtata agcaggacca ctcaatagct agggatcttg gcttgatgc agcatggata    240
actattgagt gggctagggt gttccctaag ccgacctttg acgttaaggt taaggttgat   300
gaggatgatg gaggtaacgt ggttgacgtt gaggttaatg aatcagcatt agaggagtta   360
cgcaggctag ctgacttaaa tgctgttaat cactataggg ggattttaag tgattggaag   420
gagaggggtg gtttactggt gattaacctt taccactggg ctatgcctac gtggcttcat   480
gacccaatag ccgttaggaa gaatggacct gatagagccc cctccggttg gcttgataag   540
agatccgtta ttgagttcac taagttcgca gccttcatag cccatgagtt aggtgactta   600
gctgacatgt ggtatacgat gaatgaacct ggggtagtga taactgaggg ttaccttttac  660
gttaagtcag gcttcccacc aggttacctg gacttaaact ccctagccac tgcgggtaag   720
catttaattg aggctcatgc cagagcctac gacgccatta agcctactc aaggaaacca    780
gtgggcctag tctactcctt cgcagactat cagccgctta ggcagggtga tgaggaggct   840
gttaaggagg ctaagggact tgactactca ttcttcgacg ctccaattaa gggtgaatta   900
atgggggtta ctagggatga cttgaagggt aggcttgact ggattggggt aaactactac   960
actagggccg tattgaggag gaggcaggat gctggtcggg catcagtagc cgtggtggat  1020
ggattcggct actcctgtga acctggaggc gtatctaatg ataggagacc atgcagtgac  1080
ttcggctggg aaatataccc tgagggtgtt tacaatgtct taatgaccct atggaggagg  1140
tataggatgc ccatgtacat cactgagaac ggtatagctg atgagcatga taagtggagg  1200
tcatggttca tagtatcgca cctgtatcaa attcacaggg caatggagga gggggtggat  1260
gttagagggt acttccactg gaacctaata gataacttgg agtgggctgc aggatatagg  1320
atgaggttcg gcctagttta cgttgactat gcaaccaaga ggaggtattt taggccaagc  1380
gccctggtta tgagggaggt ggctaaacag aaggctatac cggattactt agagcattac  1440
attaaaccac ctagaattga a                                            1461
```

<210> SEQ ID NO 26
<211> LENGTH: 487
<212> TYPE: PRT
<213> ORGANISM: Caldivirga maquilingensis

<400> SEQUENCE: 26

```
Met Gly Ile Lys Phe Pro Ser Asp Phe Arg Phe Gly Phe Ser Thr Val
1               5                   10                  15

Gly Thr Gln His Glu Met Gly Thr Pro Gly Ser Glu Phe Val Ser Asp
                20                  25                  30

Trp Tyr Val Trp Leu His Asp Pro Glu Asn Ile Ala Ser Gly Leu Val
            35                  40                  45

Ser Gly Asp Leu Pro Glu His Gly Pro Gly Tyr Trp Asp Leu Tyr Lys
        50                  55                  60

Gln Asp His Ser Ile Ala Arg Asp Leu Gly Leu Asp Ala Ala Trp Ile
65                  70                  75                  80

Thr Ile Glu Trp Ala Arg Val Phe Pro Lys Pro Thr Phe Asp Val Lys
                85                  90                  95
```

Val Lys Val Asp Glu Asp Gly Gly Asn Val Val Asp Val Glu Val
            100                 105                 110

Asn Glu Ser Ala Leu Glu Leu Arg Arg Leu Ala Asp Leu Asn Ala
        115                 120                 125

Val Asn His Tyr Arg Gly Ile Leu Ser Asp Trp Lys Glu Arg Gly
130                 135                 140

Leu Leu Val Ile Asn Leu Tyr His Trp Ala Met Pro Thr Trp Leu His
145                 150                 155                 160

Asp Pro Ile Ala Val Arg Lys Asn Gly Pro Asp Arg Ala Pro Ser Gly
                165                 170                 175

Trp Leu Asp Lys Arg Ser Val Ile Glu Phe Thr Lys Phe Ala Ala Phe
            180                 185                 190

Ile Ala His Glu Leu Gly Asp Leu Ala Asp Met Trp Tyr Thr Met Asn
        195                 200                 205

Glu Pro Gly Val Val Ile Thr Glu Gly Tyr Leu Tyr Val Lys Ser Gly
210                 215                 220

Phe Pro Pro Gly Tyr Leu Asp Leu Asn Ser Leu Ala Thr Ala Gly Lys
225                 230                 235                 240

His Leu Ile Glu Ala His Ala Arg Ala Tyr Asp Ala Ile Lys Ala Tyr
                245                 250                 255

Ser Arg Lys Pro Val Gly Leu Val Tyr Ser Phe Ala Asp Tyr Gln Pro
            260                 265                 270

Leu Arg Gln Gly Asp Glu Glu Ala Val Lys Glu Ala Lys Gly Leu Asp
        275                 280                 285

Tyr Ser Phe Phe Asp Ala Pro Ile Lys Gly Glu Leu Met Gly Val Thr
290                 295                 300

Arg Asp Asp Leu Lys Gly Arg Leu Asp Trp Ile Gly Val Asn Tyr Tyr
305                 310                 315                 320

Thr Arg Ala Val Leu Arg Arg Gln Asp Ala Gly Arg Ala Ser Val
                325                 330                 335

Ala Val Val Asp Gly Phe Gly Tyr Ser Cys Glu Pro Gly Gly Val Ser
            340                 345                 350

Asn Asp Arg Arg Pro Cys Ser Asp Phe Gly Trp Glu Ile Tyr Pro Glu
        355                 360                 365

Gly Val Tyr Asn Val Leu Met Asp Leu Trp Arg Arg Tyr Arg Met Pro
370                 375                 380

Met Tyr Ile Thr Glu Asn Gly Ile Ala Asp Glu His Asp Lys Trp Arg
385                 390                 395                 400

Ser Trp Phe Ile Val Ser His Leu Tyr Gln Ile His Arg Ala Met Glu
                405                 410                 415

Glu Gly Val Asp Val Arg Gly Tyr Phe His Trp Asn Leu Ile Asp Asn
            420                 425                 430

Leu Glu Trp Ala Ala Gly Tyr Arg Met Arg Phe Gly Leu Val Tyr Val
        435                 440                 445

Asp Tyr Ala Thr Lys Arg Arg Tyr Phe Arg Pro Ser Ala Leu Val Met
450                 455                 460

Arg Glu Val Ala Lys Gln Lys Ala Ile Pro Asp Tyr Leu Glu His Tyr
465                 470                 475                 480

Ile Lys Pro Pro Arg Ile Glu
                485

<210> SEQ ID NO 27
<211> LENGTH: 1476
<212> TYPE: DNA

<213> ORGANISM: Sulfolobus acidocaldarius

<400> SEQUENCE: 27

```
atgggtttat cattcccaaa gggtttcaaa tttggctggt ctcagtcggg attccagtct      60
gaaatgggaa ctccaggtag cgaagatccg aacagcgatt ggcacgtctg ggttcatgac     120
agggagaaca tagtctcaca ggttgtcagt ggagatttac ccgaaaatgg tccagggtac     180
tgggggaact ataagagatt tcatgacgaa gcagagaaaa taggactaaa tgcagtgaga     240
attaacgtag agtggagtag aatatttccc agaccactac ccaagcctga atgcaaaca      300
gggactgata agagaacag tcctgtcatt agcgtagact aaatgagtc taagctgaga       360
gaaatggaca actacgctaa tcatgaagcg ttatcacatt acaggcaaat actggaggat     420
ctaagaaaca gaggatttca catagtactg aacatgtatc attggacttt gcccatatgg     480
ttgcacgacc ctatcagagt gaggagagga gactttacag gaccaacagg ttggttaaac    540
tccaggacag tttatgagtt cgctaggttc tcggcttacg tagcctggaa attagatgat    600
ttggcgagtg aatatgcaac aatgaatgaa cctaacgtgg tttggggagc aggttacgct   660
tttcctagag caggctttcc acctaattac cttagcttca ggctttcaga aatagctaaa   720
tggaatataa ttcaggctca tgcgagggct tatgacgcca tcaagagcgt atcaaaaaag   780
agtgtaggta atatatgc aaacacatca tattacccac tcagaccaca agataacgaa     840
gctgtggaaa tagcagagag attgaacaga tggagtttct tgactccat tataaaggga   900
gagataacta gtgagggaca aaatgtcaga gaggacttaa ggaacaggtt agactggatt   960
ggcgtaaact attacacgag gactgtggta acaaaagctg agagtggtta tttaacccctt  1020
ccgggttatg gagatcgttg tgaaaggaac tcattgagtt tagctaacct ccctaccagt   1080
gatttcggtt gggagttctt tcctgagggt ctatatgatg tacttttgaa gtattggaat   1140
aggtatgggt taccattata cgtaatggag aacggtatcg ctgatgacgc tgactaccaa   1200
agaccgtatt acttagtatc acatatctac caggtgcaca gggctttaaa cgagggagta   1260
gatgtaagag gttatcttca ttggtctttg gcagataatt atgagtggtc gtcaggtttt   1320
tcaatgaggt tcggtctact taaggtagat tatctaacaa agagattgta ctggagacct   1380
tctgcattag tttacaggga gattactagg agtaacggta ttcctgagga gctggaacat   1440
ctaaacagag taccaccaat aaaacctttg agacat                               1476
```

<210> SEQ ID NO 28
<211> LENGTH: 492
<212> TYPE: PRT
<213> ORGANISM: Sulfolobus acidocaldarius

<400> SEQUENCE: 28

```
Met Gly Leu Ser Phe Pro Lys Gly Phe Lys Phe Gly Trp Ser Gln Ser
1               5                   10                  15

Gly Phe Gln Ser Glu Met Gly Thr Pro Gly Ser Glu Asp Pro Asn Ser
            20                  25                  30

Asp Trp His Val Trp Val His Asp Arg Glu Asn Ile Val Ser Gln Val
        35                  40                  45

Val Ser Gly Asp Leu Pro Glu Asn Gly Pro Gly Tyr Trp Gly Asn Tyr
    50                  55                  60

Lys Arg Phe His Asp Glu Ala Glu Lys Ile Gly Leu Asn Ala Val Arg
65                  70                  75                  80

Ile Asn Val Glu Trp Ser Arg Ile Phe Pro Arg Pro Leu Pro Lys Pro
                85                  90                  95
```

```
Glu Met Gln Thr Gly Thr Asp Lys Glu Asn Ser Pro Val Ile Ser Val
                100                 105                 110

Asp Leu Asn Glu Ser Lys Leu Arg Glu Met Asp Asn Tyr Ala Asn His
            115                 120                 125

Glu Ala Leu Ser His Tyr Arg Gln Ile Leu Glu Asp Leu Arg Asn Arg
        130                 135                 140

Gly Phe His Ile Val Leu Asn Met Tyr His Trp Thr Leu Pro Ile Trp
145                 150                 155                 160

Leu His Asp Pro Ile Arg Val Arg Arg Gly Asp Phe Thr Gly Pro Thr
                165                 170                 175

Gly Trp Leu Asn Ser Arg Thr Val Tyr Glu Phe Ala Arg Phe Ser Ala
            180                 185                 190

Tyr Val Ala Trp Lys Leu Asp Asp Leu Ala Ser Glu Tyr Ala Thr Met
        195                 200                 205

Asn Glu Pro Asn Val Val Trp Gly Ala Gly Tyr Ala Phe Pro Arg Ala
210                 215                 220

Gly Phe Pro Pro Asn Tyr Leu Ser Phe Arg Leu Ser Glu Ile Ala Lys
225                 230                 235                 240

Trp Asn Ile Ile Gln Ala His Ala Arg Ala Tyr Asp Ala Ile Lys Ser
                245                 250                 255

Val Ser Lys Lys Ser Val Gly Ile Ile Tyr Ala Asn Thr Ser Tyr Tyr
            260                 265                 270

Pro Leu Arg Pro Gln Asp Asn Glu Ala Val Glu Ile Ala Glu Arg Leu
        275                 280                 285

Asn Arg Trp Ser Phe Phe Asp Ser Ile Ile Lys Gly Glu Ile Thr Ser
290                 295                 300

Glu Gly Gln Asn Val Arg Glu Asp Leu Arg Asn Arg Leu Asp Trp Ile
305                 310                 315                 320

Gly Val Asn Tyr Tyr Thr Arg Thr Val Val Thr Lys Ala Glu Ser Gly
                325                 330                 335

Tyr Leu Thr Leu Pro Gly Tyr Gly Asp Arg Cys Glu Arg Asn Ser Leu
            340                 345                 350

Ser Leu Ala Asn Leu Pro Thr Ser Asp Phe Gly Trp Glu Phe Phe Pro
        355                 360                 365

Glu Gly Leu Tyr Asp Val Leu Leu Lys Tyr Trp Asn Arg Tyr Gly Leu
370                 375                 380

Pro Leu Tyr Val Met Glu Asn Gly Ile Ala Asp Asp Ala Asp Tyr Gln
385                 390                 395                 400

Arg Pro Tyr Tyr Leu Val Ser His Ile Tyr Gln Val His Arg Ala Leu
                405                 410                 415

Asn Glu Gly Val Asp Val Arg Gly Tyr Leu His Trp Ser Leu Ala Asp
            420                 425                 430

Asn Tyr Glu Trp Ser Ser Gly Phe Ser Met Arg Phe Gly Leu Leu Lys
        435                 440                 445

Val Asp Tyr Leu Thr Lys Arg Leu Tyr Trp Arg Pro Ser Ala Leu Val
450                 455                 460

Tyr Arg Glu Ile Thr Arg Ser Asn Gly Ile Pro Glu Glu Leu Glu His
465                 470                 475                 480

Leu Asn Arg Val Pro Pro Ile Lys Pro Leu Arg His
                485                 490

<210> SEQ ID NO 29
<211> LENGTH: 1470
```

<212> TYPE: DNA
<213> ORGANISM: Sulfolobus solfataricus

<400> SEQUENCE: 29

```
atgggttact catttccaaa tagctttagg tttggttggt cccaggccgg atttcaatca      60
gaaatgggaa caccagggtc agaagatcca aatactgact ggtataaatg ggttcatgat     120
ccagaaaaca tggcagcggg attagtaagt ggagatctac cagaaaatgg gccaggctac     180
tggggaaact ataagacatt tcacgataat gcacaaaaaa tgggattaaa aatagctaga     240
ctaaatgtgg aatggtctag gatatttcct aatccattac aaggccaca  aaactttgat     300
gaatcaaaac aagatgtgac agaggttgag ataaacgaaa acgagttaaa gagacttgac     360
gagtacgcta ataagacgc attaaaccat acagggaaa tattcaagga tcttaaaagt       420
agaggacttt actttatact aaacatgtat cattggccat tacctctatg gttacacgac     480
ccaataagag taagaagagg agattttact ggaccaagtg gttggctaag tactagaaca     540
gtttacgagt tcgctagatt ctcagcttat atagcttgga aattcgatga tctagtggat     600
gagtactcaa caatgaatga acctaacgtt gttggaggtt taggatacgt tggtgttaag     660
tccggttttc ccccaggata cctaagcttt gaactttccc gtagggcaat gtataacatc     720
attcaagctc acgcaagagc gtatgatggg ataaagagtg tttctaaaaa accagttgga     780
attatttacg ctaatagctc attccagccg ttaacggata agatatgga  agcggtagag     840
atggctgaaa tgataatag  atggtggttc tttgatgcta taataagagg tgagatcacc     900
agaggaaacg agaagattgt aagagatgac ctaaagggta gattggattg gattggagtt     960
aattattaca ctaggactgt tgtgaagagg actgaaaagg gatacgttag cttaggaggt    1020
tacggtcacg gatgtgagag gaactctgta agtttagcgg gattaccaac cagcgacttc    1080
ggctgggagt tcttcccaga aggtttatat gacgttttga cgaaatactg gaatagatat    1140
catctctata tgtacgttac tgaaaatggt attgcggatg atgccgatta tcaaaggccc    1200
tattatttag tatctcacgt ttatcaagtt catagagcaa taatagtgg  tgcagatgtt    1260
agagggtatt tacattggtc tctagctgat aattacgaat gggcttcagg attctctatg    1320
aggtttggtc tgttaaaggt cgattacaac actaagagac tatactggag accctcagca    1380
ctagtatata gggaaatcgc cacaaatggc gcaataactg atgaaataga gcacttaaat    1440
agcgtacctc cagtaaagcc attaaggcac                                     1470
```

<210> SEQ ID NO 30
<211> LENGTH: 490
<212> TYPE: PRT
<213> ORGANISM: Sulfolobus solfataricus

<400> SEQUENCE: 30

```
Met Gly Tyr Ser Phe Pro Asn Ser Phe Arg Phe Gly Trp Ser Gln Ala
1               5                   10                  15

Gly Phe Gln Ser Glu Met Gly Thr Pro Gly Ser Glu Asp Pro Asn Thr
            20                  25                  30

Asp Trp Tyr Lys Trp Val His Asp Pro Glu Asn Met Ala Ala Gly Leu
        35                  40                  45

Val Ser Gly Asp Leu Pro Glu Asn Gly Pro Gly Tyr Trp Gly Asn Tyr
    50                  55                  60

Lys Thr Phe His Asp Asn Ala Gln Lys Met Gly Leu Lys Ile Ala Arg
65                  70                  75                  80

Leu Asn Val Glu Trp Ser Arg Ile Phe Pro Asn Pro Leu Pro Arg Pro
```

```
                    85                  90                  95
Gln Asn Phe Asp Glu Ser Lys Gln Asp Val Thr Glu Val Glu Ile Asn
                100                 105                 110
Glu Asn Glu Leu Lys Arg Leu Asp Glu Tyr Ala Asn Lys Asp Ala Leu
            115                 120                 125
Asn His Tyr Arg Glu Ile Phe Lys Asp Leu Lys Ser Arg Gly Leu Tyr
        130                 135                 140
Phe Ile Leu Asn Met Tyr His Trp Pro Leu Pro Leu Trp Leu His Asp
145                 150                 155                 160
Pro Ile Arg Val Arg Arg Gly Asp Phe Thr Gly Pro Ser Gly Trp Leu
                165                 170                 175
Ser Thr Arg Thr Val Tyr Glu Phe Ala Arg Phe Ser Ala Tyr Ile Ala
            180                 185                 190
Trp Lys Phe Asp Asp Leu Val Asp Glu Tyr Ser Thr Met Asn Glu Pro
        195                 200                 205
Asn Val Val Gly Gly Leu Gly Tyr Val Gly Val Lys Ser Gly Phe Pro
    210                 215                 220
Pro Gly Tyr Leu Ser Phe Glu Leu Ser Arg Arg Ala Met Tyr Asn Ile
225                 230                 235                 240
Ile Gln Ala His Ala Arg Ala Tyr Asp Gly Ile Lys Ser Val Ser Lys
                245                 250                 255
Lys Pro Val Gly Ile Ile Tyr Ala Asn Ser Ser Phe Gln Pro Leu Thr
            260                 265                 270
Asp Lys Asp Met Glu Ala Val Glu Met Ala Glu Asn Asp Asn Arg Trp
        275                 280                 285
Trp Phe Phe Asp Ala Ile Ile Arg Gly Glu Ile Thr Arg Gly Asn Glu
    290                 295                 300
Lys Ile Val Arg Asp Asp Leu Lys Gly Arg Leu Asp Trp Ile Gly Val
305                 310                 315                 320
Asn Tyr Tyr Thr Arg Thr Val Val Lys Arg Thr Glu Lys Gly Tyr Val
                325                 330                 335
Ser Leu Gly Gly Tyr Gly His Gly Cys Glu Arg Asn Ser Val Ser Leu
            340                 345                 350
Ala Gly Leu Pro Thr Ser Asp Phe Gly Trp Glu Phe Phe Pro Glu Gly
        355                 360                 365
Leu Tyr Asp Val Leu Thr Lys Tyr Trp Asn Arg Tyr His Leu Tyr Met
    370                 375                 380
Tyr Val Thr Glu Asn Gly Ile Ala Asp Asp Ala Asp Tyr Gln Arg Pro
385                 390                 395                 400
Tyr Tyr Leu Val Ser His Val Tyr Gln Val His Arg Ala Ile Asn Ser
                405                 410                 415
Gly Ala Asp Val Arg Gly Tyr Leu His Trp Ser Leu Ala Asp Asn Tyr
            420                 425                 430
Glu Trp Ala Ser Gly Phe Ser Met Arg Phe Gly Leu Leu Lys Val Asp
        435                 440                 445
Tyr Asn Thr Lys Arg Leu Tyr Trp Arg Pro Ser Ala Leu Val Tyr Arg
    450                 455                 460
Glu Ile Ala Thr Asn Gly Ala Ile Thr Asp Glu Ile Glu His Leu Asn
465                 470                 475                 480
Ser Val Pro Pro Val Lys Pro Leu Arg His
                485                 490

<210> SEQ ID NO 31
```

-continued

```
<211> LENGTH: 1488
<212> TYPE: DNA
<213> ORGANISM: Picrophilus torridus

<400> SEQUENCE: 31
atgggtttac ccaagaactt tttacttggc ttttctctgg ctggctttca gtctgaaatg      60
ggcatatcag atcctgatag caattcagat tggtggttat gggtacatga cccggtgaat     120
ataaggactg gacttgtatc tggtgactta cctgaaaatg gaataggata ctggatcttc     180
tacaaaaaat ataatggtct ggctgttcaa acaggaatga atgctgcaag cttggagtt     240
gaatggagca ggatatttcc aaaaagtact gaagaagtaa aggtgatgga agattacaaa     300
gatgatgatt taatttccgt ggatgttaat gagggaagtc ttgaaaaact tgacagactg     360
gcaaatcaaa aggcaattaa tagatatatg gaaatcttca ataatatcaa ggaaaataat     420
atgacgctaa tagtgaatgt ttaccattgg ccaataccaa tatatcttca cgatccaata     480
gaagctagga atagtggact ttcaaataaa gaaatggct ggcttaatca taaaaccgtt      540
gtggaatttg taaaatatgc aaaatatctg gcatggaaat ttagcgatgt ggcagatatg     600
tttttctataa tgaatgagcc aaacgttgta tttggtaatg atatttttaa tgttaaatca     660
gggttcccac cagcatttcc aagtgtgcat ggcggtttgc ttgcaaaaaa acatgaaatt     720
gaggctatag caagatcata cgacgccatg aaggagatta caaaaaaacc agttggtcta     780
attatggcaa attcagatgt acaaccacta acagatgagg ataagaagc agcagaaatg     840
gctacttaca atgatcgcta ttcattcata gatccgctaa gagttggtga tgatgaaatg     900
gctgatgagg ttactgcagg taatccaatt ggtgaaaaga gcaacatcga tagatctgat     960
ctaaaaaata gctagactg gataggtgtt aactattata caagggccgt tgtaaaaaaa    1020
tctggaaacg gatatacaac attaaaagga tatggacact ctgcaaccgc tggcatgcca    1080
agtagggccg aagggatgt aagtgacttt ggctgggaat ttatccaga aggtcttgta     1140
aacgtcttat catcatactg gaaaagatat cacattccaa tgattgtgac tgaaaatggt    1200
gttgctgact ctattgatag acttagacca aggtaccttg tgtcacatat aaagtctgtt    1260
gaaaaggctt tatctatggg tatggatatt agggggatatc ttcactggtc tctgattgat    1320
aactatgaat gggcatcagg tttttcaatg aaatttgggc tttatggtat tgatttgaac    1380
aataaaaaga ttcaacacag accaagtgca ctggtattta agaaaattgc aaatgccaac    1440
ggagtcccgg aggaatttga atggatggca gaccagcatc agaactca             1488

<210> SEQ ID NO 32
<211> LENGTH: 496
<212> TYPE: PRT
<213> ORGANISM: Picrophilus torridus

<400> SEQUENCE: 32
```

Met Gly Leu Pro Lys Asn Phe Leu Leu Gly Phe Ser Leu Ala Gly Phe
1               5                   10                  15

Gln Ser Glu Met Gly Ile Ser Asp Pro Asp Ser Asn Ser Asp Trp Trp
            20                  25                  30

Leu Trp Val His Asp Pro Val Asn Ile Arg Thr Gly Leu Val Ser Gly
        35                  40                  45

Asp Leu Pro Glu Asn Gly Ile Gly Tyr Trp Asp Leu Tyr Lys Lys Tyr
    50                  55                  60

Asn Gly Leu Ala Val Gln Thr Gly Met Asn Ala Ala Arg Leu Gly Val
65                  70                  75                  80

```
Glu Trp Ser Arg Ile Phe Pro Lys Ser Thr Glu Val Lys Val Met
             85                  90                  95

Glu Asp Tyr Lys Asp Asp Leu Ile Ser Val Asp Val Asn Glu Gly
            100                 105                 110

Ser Leu Glu Lys Leu Asp Arg Leu Ala Asn Gln Lys Ala Ile Asn Arg
            115                 120                 125

Tyr Met Glu Ile Phe Asn Asn Ile Lys Glu Asn Asn Met Thr Leu Ile
            130                 135                 140

Val Asn Val Tyr His Trp Pro Ile Pro Ile Tyr Leu His Asp Pro Ile
145                 150                 155                 160

Glu Ala Arg Asn Ser Gly Leu Ser Asn Lys Arg Asn Gly Trp Leu Asn
                165                 170                 175

His Lys Thr Val Val Glu Phe Val Lys Tyr Ala Lys Tyr Leu Ala Trp
            180                 185                 190

Lys Phe Ser Asp Val Ala Asp Met Phe Ser Ile Met Asn Glu Pro Asn
            195                 200                 205

Val Val Phe Gly Asn Gly Tyr Phe Asn Val Lys Ser Gly Phe Pro Pro
210                 215                 220

Ala Phe Pro Ser Val His Gly Leu Leu Ala Lys Lys His Glu Ile
225                 230                 235                 240

Glu Ala Ile Ala Arg Ser Tyr Asp Ala Met Lys Glu Ile Thr Lys Lys
                245                 250                 255

Pro Val Gly Leu Ile Met Ala Asn Ser Asp Val Gln Pro Leu Thr Asp
            260                 265                 270

Glu Asp Lys Glu Ala Ala Glu Met Ala Thr Tyr Asn Asp Arg Tyr Ser
            275                 280                 285

Phe Ile Asp Pro Leu Arg Val Gly Glu Met Lys Trp Ala Asp Glu Val
290                 295                 300

Thr Ala Gly Asn Pro Ile Gly Glu Lys Ser Asn Ile Asp Arg Ser Asp
305                 310                 315                 320

Leu Lys Asn Lys Leu Asp Trp Ile Gly Val Asn Tyr Tyr Thr Arg Ala
                325                 330                 335

Val Val Lys Lys Ser Gly Asn Gly Tyr Thr Thr Leu Lys Gly Tyr Gly
            340                 345                 350

His Ser Ala Thr Ala Gly Met Pro Ser Arg Ala Gly Arg Asp Val Ser
            355                 360                 365

Asp Phe Gly Trp Glu Phe Tyr Pro Glu Gly Leu Val Asn Val Leu Ser
            370                 375                 380

Ser Tyr Trp Lys Arg Tyr His Ile Pro Met Ile Val Thr Glu Asn Gly
385                 390                 395                 400

Val Ala Asp Ser Ile Asp Arg Leu Arg Pro Arg Tyr Leu Val Ser His
                405                 410                 415

Ile Lys Ser Val Glu Lys Ala Leu Ser Met Gly Met Asp Ile Arg Gly
            420                 425                 430

Tyr Leu His Trp Ser Leu Ile Asp Asn Tyr Glu Trp Ala Ser Gly Phe
            435                 440                 445

Ser Met Lys Phe Gly Leu Tyr Gly Ile Asp Leu Asn Asn Lys Lys Ile
450                 455                 460

Gln His Arg Pro Ser Ala Leu Val Phe Lys Glu Ile Ala Asn Ala Asn
465                 470                 475                 480

Gly Val Pro Glu Glu Phe Glu Trp Met Ala Asp Gln His Gln Asn Ser
                485                 490                 495
```

-continued

<210> SEQ ID NO 33
<211> LENGTH: 1443
<212> TYPE: DNA
<213> ORGANISM: Thermoplasma volcanium

<400> SEQUENCE: 33

```
atggtagaaa acaatttttcc agaggatttc aaatttggtt ggtcacagtc aggttttcaa      60
tcggagatgg gctatgataa cgcaatggac gataaaagtg actggtatgt ctgggttcat     120
gataaagaaa acatccaatc agggcttgta agcggagaca tgcccgaaaa tggtccgggt     180
tactggaata actataaatc attccatgaa gctgcacaga atatgggatt aaaaatggca     240
agaatcggag ttgaatggtc aagattattc ccggaacctt tcccgaaaaa ataatggca      300
gatgcaaaaa ataattcctt agaaataaac aataacattc tttcagaact tgataaatat     360
gtcaataaag atgcactcaa ccattacatt gagatattta atgatatcaa aaatagaaat     420
atagatttaa taattaatat gtaccactgg ccacttcctg tatggctaag cgatcctgta     480
tctgttagaa aaggaataaa aacagaaaga tcaggctggc tgaatgacag atagttcaa      540
ttgtttgctt tattctcctc gtatatagta tataaaatgg aagatctggc agttgcattt     600
tcaaccatga atgaacctaa tgttgtttat ggaaatggtt ttataaatat caaatcaggt     660
tttccgcctt cctatctcag ttcagaattt gcatctaaag ttaagaacaa tatattaaaa     720
gcacattctc ttgcatacga ttctatgaaa aaaattacgg ataaacctgt gggaataatt     780
tatgcaaaca catatttac gcctttggac ccggaaaaag ataatgatgc tattgctaaa      840
gcagacagtg atgcgaaatg gtcattttttt gatccattaa taaaggaga taaatcactt     900
ggaattaatg gcaataaact agattggatc ggaattaatt attatacaag gacaatgtta     960
aggaaagacg gagatggcta tatttcatta aaaggctatg gtcattcagg ttctcctaat    1020
actgtaacaa acgataaaag accaacaagt gatataggat gggaattta tccggaggga    1080
ttggaatatg taattatgaa ttactggaac aggtataaat tgcctatgta cgtaacagaa    1140
aatggcatag ccgataatgg ggattatcag aggccttatt atttagtttc acacattgca    1200
agtgtactga gggcaataaa taaggagcc aatgtaaagg ttatttgca ctggtcctta      1260
gttgataatt atgaatgggc attgggattt agcccgaaat ttggtttaat aggatacgat    1320
gaaaataaaa aactatactg gaggccaagt gctcttgttt ataaggaaat agcaacaaaa    1380
aattgcatat ccccagaatt aaagcacctc gattcaatac cgcctataaa tggtttaaga    1440
aaa                                                                  1443
```

<210> SEQ ID NO 34
<211> LENGTH: 481
<212> TYPE: PRT
<213> ORGANISM: Thermoplasma volcanium

<400> SEQUENCE: 34

```
Met Val Glu Asn Asn Phe Pro Glu Asp Phe Lys Phe Gly Trp Ser Gln
1               5                   10                  15

Ser Gly Phe Gln Ser Glu Met Gly Tyr Asp Asn Ala Met Asp Asp Lys
            20                  25                  30

Ser Asp Trp Tyr Val Trp Val His Asp Lys Glu Asn Ile Gln Ser Gly
        35                  40                  45

Leu Val Ser Gly Asp Met Pro Glu Asn Gly Pro Gly Tyr Trp Asn Asn
    50                  55                  60

Tyr Lys Ser Phe His Glu Ala Ala Gln Asn Met Gly Leu Lys Met Ala
65                  70                  75                  80
```

```
Arg Ile Gly Val Glu Trp Ser Arg Leu Phe Pro Glu Pro Phe Pro Glu
                85                  90                  95
Lys Ile Met Ala Asp Ala Lys Asn Asn Ser Leu Glu Ile Asn Asn Asn
                100                 105                 110
Ile Leu Ser Glu Leu Asp Lys Tyr Val Asn Lys Asp Ala Leu Asn His
                115                 120                 125
Tyr Ile Glu Ile Phe Asn Asp Ile Lys Asn Arg Asn Ile Asp Leu Ile
            130                 135                 140
Ile Asn Met Tyr His Trp Pro Leu Pro Val Trp Leu Ser Asp Pro Val
145                 150                 155                 160
Ser Val Arg Lys Gly Ile Lys Thr Glu Arg Ser Gly Trp Leu Asn Asp
                165                 170                 175
Arg Ile Val Gln Leu Phe Ala Leu Phe Ser Ser Tyr Ile Val Tyr Lys
                180                 185                 190
Met Glu Asp Leu Ala Val Ala Phe Ser Thr Met Asn Glu Pro Asn Val
                195                 200                 205
Val Tyr Gly Asn Gly Phe Ile Asn Ile Lys Ser Gly Phe Pro Pro Ser
                210                 215                 220
Tyr Leu Ser Ser Glu Phe Ala Ser Lys Val Lys Asn Asn Ile Leu Lys
225                 230                 235                 240
Ala His Ser Leu Ala Tyr Asp Ser Met Lys Lys Ile Thr Asp Lys Pro
                245                 250                 255
Val Gly Ile Ile Tyr Ala Asn Thr Tyr Phe Thr Pro Leu Asp Pro Glu
                260                 265                 270
Lys Asp Asn Asp Ala Ile Ala Lys Ala Asp Ser Asp Ala Lys Trp Ser
                275                 280                 285
Phe Phe Asp Pro Leu Ile Lys Gly Asp Lys Ser Leu Gly Ile Asn Gly
                290                 295                 300
Asn Lys Leu Asp Trp Ile Gly Ile Asn Tyr Tyr Thr Arg Thr Met Leu
305                 310                 315                 320
Arg Lys Asp Gly Asp Gly Tyr Ile Ser Leu Lys Gly Tyr Gly His Ser
                325                 330                 335
Gly Ser Pro Asn Thr Val Thr Asn Asp Lys Arg Pro Thr Ser Asp Ile
                340                 345                 350
Gly Trp Glu Phe Tyr Pro Glu Gly Leu Glu Tyr Val Ile Met Asn Tyr
                355                 360                 365
Trp Asn Arg Tyr Lys Leu Pro Met Tyr Val Thr Glu Asn Gly Ile Ala
                370                 375                 380
Asp Asn Gly Asp Tyr Gln Arg Pro Tyr Tyr Leu Val Ser His Ile Ala
385                 390                 395                 400
Ser Val Leu Arg Ala Ile Asn Lys Gly Ala Asn Val Lys Gly Tyr Leu
                405                 410                 415
His Trp Ser Leu Val Asp Asn Tyr Glu Trp Ala Leu Gly Phe Ser Pro
                420                 425                 430
Lys Phe Gly Leu Ile Gly Tyr Asp Glu Asn Lys Lys Leu Tyr Trp Arg
                435                 440                 445
Pro Ser Ala Leu Val Tyr Lys Glu Ile Ala Thr Lys Asn Cys Ile Ser
450                 455                 460
Pro Glu Leu Lys His Leu Asp Ser Ile Pro Pro Ile Asn Gly Leu Arg
465                 470                 475                 480

Lys
```

<210> SEQ ID NO 35
<211> LENGTH: 1404
<212> TYPE: DNA
<213> ORGANISM: Fervidobacterium nodosum

<400> SEQUENCE: 35

```
atgggtatgt tccgaaaga tttttatttt ggtgtttcga tgtctgggtt tcagtttgag      60
atgggaaatc ctcaagatgc agaagaggtt gatctaaata cagattggta tgtatgggtt     120
agggatattg gaaatattgt aaatggagtc gtaagtgggg acttgcctga aaatggttca    180
tggtactgga agcagtacgg caaagtccac caattagctg ccgattttgg gatggatgta    240
atacgaattg gaaccgaatg gtctaggatt ttcccagtta gtacgcaaag tgttgagtac    300
ggctcaccgg atatgctcga aaaattggat aaattagcaa accaaaaagc ggtaagtcat    360
tacaggaaaa taatggagga tataaaagca aaggggttaa aattgttcgt taacctttac    420
cactttactt tacctatttg gttgcacgac cctatagctg ttcacaaagg tgagaagaca    480
gataaaattg gttggatttc tgatgctaca cctattgagt ttgcgaagta tgcagagtac    540
atggcgtgga aatttgccga tatagttgat atgtgggctt ctatgaacga accacacgtt    600
gtaagtcagc ttggatattt tgcaataaat gcgggatttc caccaagtta tttttaatcct   660
tcatggtata tcaaaagttt agaaaacgaa gcgaaagcac ataacttatc ttatgatgct    720
ataaaaagt atacaaataa tcctgttgga gttatatact cttttacatg gtacgatact    780
gttaataaag atgacaagga atcttttgaa aatgctatgg atctcacaaa ttggcgattt    840
atagatatgg taaagataa aactgattac ataggtgtaa attattacac aagagcggtt    900
atcgatagac ttcccaccac tattgacttt ggcgaattta aaatgaattg gtatactttg    960
agaggttacg gttattcttg cgaagaagga ggattctcac tctccggaag gccggcaagc   1020
gaatttggat gggaaatata ccctgaaggg ctgtacaata ttttgataca tgtttataat   1080
agatacaaaa aagatatttta tgttacgagg aacggtatag ctgattcgaa ggataaaatac  1140
agaagtcttt ttatcatatc gcatctttat gctatagaaa aagcattaaa cgaaggaata   1200
ccaataaaag gttatttgca ctggtcgatt atagacaatt tcgaatgggc gaagggctac   1260
agtaaaagat ttggacttgc ttacacagat ttgtcaacca aaaatatat acctagacct   1320
tctatgtaca tttttagaga gataataaag gataaatcaa tcgacaaatt caaaggttac   1380
gatccatata acttgatgaa attc                                           1404
```

<210> SEQ ID NO 36
<211> LENGTH: 468
<212> TYPE: PRT
<213> ORGANISM: Fervidobacterium nodosum

<400> SEQUENCE: 36

```
Met Gly Met Phe Pro Lys Asp Phe Leu Phe Gly Val Ser Met Ser Gly
1               5                   10                  15

Phe Gln Phe Glu Met Gly Asn Pro Gln Asp Ala Glu Glu Val Asp Leu
            20                  25                  30

Asn Thr Asp Trp Tyr Val Trp Val Arg Asp Ile Gly Asn Ile Val Asn
        35                  40                  45

Gly Val Val Ser Gly Asp Leu Pro Glu Asn Gly Ser Trp Tyr Trp Lys
    50                  55                  60

Gln Tyr Gly Lys Val His Gln Leu Ala Ala Asp Phe Gly Met Asp Val
65                  70                  75                  80

Ile Arg Ile Gly Thr Glu Trp Ser Arg Ile Phe Pro Val Ser Thr Gln
```

85                  90                  95
Ser Val Glu Tyr Gly Ser Pro Asp Met Leu Glu Lys Leu Asp Lys Leu
            100                 105                 110

Ala Asn Gln Lys Ala Val Ser His Tyr Arg Lys Ile Met Glu Asp Ile
        115                 120                 125

Lys Ala Lys Gly Leu Lys Leu Phe Val Asn Leu Tyr His Phe Thr Leu
    130                 135                 140

Pro Ile Trp Leu His Asp Pro Ile Ala Val His Lys Gly Glu Lys Thr
145                 150                 155                 160

Asp Lys Ile Gly Trp Ile Ser Asp Ala Thr Pro Ile Glu Phe Ala Lys
                165                 170                 175

Tyr Ala Glu Tyr Met Ala Trp Lys Phe Ala Asp Ile Val Asp Met Trp
            180                 185                 190

Ala Ser Met Asn Glu Pro His Val Val Ser Gln Leu Gly Tyr Phe Ala
        195                 200                 205

Ile Asn Ala Gly Phe Pro Pro Ser Tyr Phe Asn Pro Ser Trp Tyr Ile
    210                 215                 220

Lys Ser Leu Glu Asn Glu Ala Lys Ala His Asn Leu Ser Tyr Asp Ala
225                 230                 235                 240

Ile Lys Lys Tyr Thr Asn Asn Pro Val Gly Val Ile Tyr Ser Phe Thr
                245                 250                 255

Trp Tyr Asp Thr Val Asn Lys Asp Asp Lys Glu Ser Phe Glu Asn Ala
            260                 265                 270

Met Asp Leu Thr Asn Trp Arg Phe Ile Asp Met Val Lys Asp Lys Thr
        275                 280                 285

Asp Tyr Ile Gly Val Asn Tyr Tyr Thr Arg Ala Val Ile Asp Arg Leu
    290                 295                 300

Pro Thr Thr Ile Asp Phe Gly Glu Phe Lys Met Asn Trp Tyr Thr Leu
305                 310                 315                 320

Arg Gly Tyr Gly Tyr Ser Cys Glu Glu Gly Gly Phe Ser Leu Ser Gly
                325                 330                 335

Arg Pro Ala Ser Glu Phe Gly Trp Glu Ile Tyr Pro Glu Gly Leu Tyr
            340                 345                 350

Asn Ile Leu Ile His Val Tyr Asn Arg Tyr Lys Lys Asp Ile Tyr Val
        355                 360                 365

Thr Glu Asn Gly Ile Ala Asp Ser Lys Asp Lys Tyr Arg Ser Leu Phe
    370                 375                 380

Ile Ile Ser His Leu Tyr Ala Ile Glu Lys Ala Leu Asn Glu Gly Ile
385                 390                 395                 400

Pro Ile Lys Gly Tyr Leu His Trp Ser Ile Ile Asp Asn Phe Glu Trp
                405                 410                 415

Ala Lys Gly Tyr Ser Lys Arg Phe Gly Leu Ala Tyr Thr Asp Leu Ser
            420                 425                 430

Thr Lys Lys Tyr Ile Pro Arg Pro Ser Met Tyr Ile Phe Arg Glu Ile
        435                 440                 445

Ile Lys Asp Lys Ser Ile Asp Lys Phe Lys Gly Tyr Asp Pro Tyr Asn
    450                 455                 460

Leu Met Lys Phe
465

<210> SEQ ID NO 37
<211> LENGTH: 1446
<212> TYPE: DNA
<213> ORGANISM: Artificial Sequence
<220> FEATURE:
<223> OTHER INFORMATION: Description of Artificial Sequence: Synthetic
polynucleotide encoding mutant beta-glycosidase
of Thermosphaera aggregans having glycosylation
site

<400> SEQUENCE: 37

| | | | | | |
|---|---|---|---|---|---|
| atgggtaaat | tccccaaaga | cttcatgata | ggctactcat | cttcaccgtt | tcaatttgaa | 60
| gctggtattc | ccgggtccga | agatccgaat | agtgattggt | gggtatgggt | gcatgatccg | 120
| gagaacacag | cagctggact | agtcagcggc | gattttcccg | agaacggccc | aggttactgg | 180
| aaccgcactc | aaaatgacca | cgacctggct | gagaagctgg | gggttaacac | tattagagta | 240
| ggcgttgagt | ggagtaggat | ttttccaaag | ccaactttca | atgttaaagt | ccctgtagag | 300
| agagatgaga | acggcagcat | tgttcacgta | gatgtcgatg | ataaagcggt | tgaaagactt | 360
| gatgaattag | ccaacaagga | ggccgtaaac | cattacgtag | aaatgtataa | agactgggtt | 420
| gaaagaggta | gaaaacttat | actcaattta | taccattggc | ccctgcctct | ctggcttcac | 480
| aacccaatca | tggtgagaag | aatgggcccg | acagagcgc | cctcaggctg | gcttaacgag | 540
| gagtccgtgg | tggagtttgc | caaatacgcc | gcatacattg | cttggaaaat | gggcgagcta | 600
| cctgttatgt | ggagcaccat | gaacgaaccc | aacgtcgttt | atgagcaagg | atacatgttc | 660
| gttaaagggg | gtttcccacc | cggctacttg | agtttggaag | ctgctgataa | ggccaggaga | 720
| aatatgatcc | aggctcatgc | acgggcctat | gacaatatta | aacgcttcag | taagaaacct | 780
| gttggactaa | tatacgcttt | ccaatggttc | gaactattag | agggtccagc | agaagtattt | 840
| gataagttta | agagctctaa | gttatactat | ttcacagaca | tagtatcgaa | gggtagttca | 900
| atcatcaatg | ttgaatacag | gagagatctt | gccaataggc | tagactggtt | gggcgttaac | 960
| tactatagcc | gttagtcta | caaaatcgtc | gatgacaaac | ctataatcct | gcacgggtat | 1020
| ggattccttt | gtacacctgg | ggggatcagc | ccggctgaaa | tccttgtag | cgattttggg | 1080
| tgggaggtgt | atcctgaagg | actctaccta | cttctaaaag | aactttacaa | ccgatacggg | 1140
| gtagacttga | tcgtgaccga | gaacggtgtt | tcagacagca | gggatgcgtt | gagaccggca | 1200
| tacctggtct | cgcatgttta | cagcgtatgg | aaagccgcta | acgagggcat | tcccgtcaaa | 1260
| ggctacctcc | actggagctt | gacagacaat | tacgagtggg | cccagggctt | caggcagaaa | 1320
| ttcggtttag | tcatggttga | cttcaaaact | aagaaaaggt | atctccgccc | aagcgcccta | 1380
| gtgttccggg | agatcgcaac | gcataacgga | ataccggatg | agctacagca | tcttacactg | 1440
| atccag | | | | | | 1446

<210> SEQ ID NO 38
<211> LENGTH: 482
<212> TYPE: PRT
<213> ORGANISM: Artificial Sequence
<220> FEATURE:
<223> OTHER INFORMATION: Description of Artificial Sequence: Synthetic
mutant beta-glycosidase polypeptide of Thermosphaera
aggregans having glycosylation site
<220> FEATURE:
<221> NAME/KEY: misc_feature
<222> LOCATION: (61)..(63)
<223> OTHER INFORMATION: CARBOHYD

<400> SEQUENCE: 38

Met Gly Lys Phe Pro Lys Asp Phe Met Ile Gly Tyr Ser Ser Ser Pro
1               5                   10                  15

Phe Gln Phe Glu Ala Gly Ile Pro Gly Ser Glu Asp Pro Asn Ser Asp
            20                  25                  30

```
Trp Trp Val Trp Val His Asp Pro Glu Asn Thr Ala Ala Gly Leu Val
        35                  40                  45

Ser Gly Asp Phe Pro Glu Asn Gly Pro Gly Tyr Trp Asn Arg Thr Gln
    50                  55                  60

Asn Asp His Asp Leu Ala Glu Lys Leu Gly Val Asn Thr Ile Arg Val
 65                  70                  75                  80

Gly Val Glu Trp Ser Arg Ile Phe Pro Lys Pro Thr Phe Asn Val Lys
                85                  90                  95

Val Pro Val Glu Arg Asp Glu Asn Gly Ser Ile Val His Val Asp Val
            100                 105                 110

Asp Asp Lys Ala Val Glu Arg Leu Asp Glu Leu Ala Asn Lys Glu Ala
        115                 120                 125

Val Asn His Tyr Val Glu Met Tyr Lys Asp Trp Val Glu Arg Gly Arg
    130                 135                 140

Lys Leu Ile Leu Asn Leu Tyr His Trp Pro Leu Pro Leu Trp Leu His
145                 150                 155                 160

Asn Pro Ile Met Val Arg Arg Met Gly Pro Asp Arg Ala Pro Ser Gly
                165                 170                 175

Trp Leu Asn Glu Glu Ser Val Val Glu Phe Ala Lys Tyr Ala Ala Tyr
            180                 185                 190

Ile Ala Trp Lys Met Gly Glu Leu Pro Val Met Trp Ser Thr Met Asn
        195                 200                 205

Glu Pro Asn Val Val Tyr Glu Gln Gly Tyr Met Phe Val Lys Gly Gly
    210                 215                 220

Phe Pro Pro Gly Tyr Leu Ser Leu Glu Ala Ala Asp Lys Ala Arg Arg
225                 230                 235                 240

Asn Met Ile Gln Ala His Ala Arg Ala Tyr Asp Asn Ile Lys Arg Phe
                245                 250                 255

Ser Lys Lys Pro Val Gly Leu Ile Tyr Ala Phe Gln Trp Phe Glu Leu
            260                 265                 270

Leu Glu Gly Pro Ala Glu Val Phe Asp Lys Phe Lys Ser Ser Lys Leu
        275                 280                 285

Tyr Tyr Phe Thr Asp Ile Val Ser Lys Gly Ser Ser Ile Ile Asn Val
    290                 295                 300

Glu Tyr Arg Arg Asp Leu Ala Asn Arg Leu Asp Trp Leu Gly Val Asn
305                 310                 315                 320

Tyr Tyr Ser Arg Leu Val Tyr Lys Ile Val Asp Asp Lys Pro Ile Ile
                325                 330                 335

Leu His Gly Tyr Gly Phe Leu Cys Thr Pro Gly Gly Ile Ser Pro Ala
            340                 345                 350

Glu Asn Pro Cys Ser Asp Phe Gly Trp Glu Val Tyr Pro Glu Gly Leu
        355                 360                 365

Tyr Leu Leu Leu Lys Glu Leu Tyr Asn Arg Tyr Gly Val Asp Leu Ile
    370                 375                 380

Val Thr Glu Asn Gly Val Ser Asp Ser Arg Asp Ala Leu Arg Pro Ala
385                 390                 395                 400

Tyr Leu Val Ser His Val Tyr Ser Val Trp Lys Ala Ala Asn Glu Gly
                405                 410                 415

Ile Pro Val Lys Gly Tyr Leu His Trp Ser Leu Thr Asp Asn Tyr Glu
            420                 425                 430

Trp Ala Gln Gly Phe Arg Gln Lys Phe Gly Leu Val Met Val Asp Phe
        435                 440                 445
```

```
Lys Thr Lys Lys Arg Tyr Leu Arg Pro Ser Ala Leu Val Phe Arg Glu
    450                 455                 460

Ile Ala Thr His Asn Gly Ile Pro Asp Glu Leu Gln His Leu Thr Leu
465                 470                 475                 480

Ile Gln

<210> SEQ ID NO 39
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide encoding mutant glycoside hydrolase
      family protein of Caldivirga maquilingensis having
      glycosylation site

<400> SEQUENCE: 39
atgggtatta agttcccaag cgacttcaga ttcggcttct ccacagtggg tactcagcat      60
gagatgggta cccctggttc tgaatttgta agtgactggt atgtgtggct tcatgaccct     120
gagaacattg cttcgggctt agttagcggt gatttacctg aacatgggcc aggttactgg     180
aaccgcacta gcaggaccca ctcaatagct agggatcttg gcttgatgc agcatggata      240 actattgagt gggctagggt gttccctaag ccgacctttg acgttaaggt taaggttgat     300
gaggatgatg gaggtaacgt ggttgacgtt gaggttaatg aatcagcatt agaggagtta     360
cgcaggctag ctgacttaaa tgctgttaat cactataggg ggattttaag tgattggaag     420
gagaggggtg gtttactggt gattaaccct taccactggg ctatgcctac gtggcttcat     480
gacccaatag ccgttaggaa gaatggacct gatagagccc cctccggttg gcttgataag     540
agatccgtta ttgagttcac taagttcgca gccttcatag cccatgagtt aggtgactta     600
gctgacatgt ggtatacgat gaatgaacct ggggtagtga taactgaggg ttacctttac     660
gttaagtcag gcttcccacc aggttacctg gacttaaact ccctagccac tgcgggtaag     720
catttaattg aggctcatgc cagagcctac gacgccatta agcctactc aaggaaacca      780 gtgggcctag tctactcctt cgcagactat cagccgctta gcagggtga tgaggaggct      840 gttaaggagg ctaagggact tgactactca ttcttcgacg ctccaattaa gggtgaatta     900 atggggggtta ctaggatga cttgaagggt aggcttgact ggattgggt aaactactac      960 actagggccg tattgaggag gaggcaggat gctggtcggg catcagtagc cgtggtggat    1020
ggattcggct actcctgtga acctggaggc gtatctaatg ataggagacc atgcagtgac    1080
ttcggctggg aaatataccc tgagggtgtt tacaatgtct taatggacct atggaggagg    1140
tataggatgc ccatgtacat cactgagaac ggtatagctg atgagcatga taagtggagg    1200
tcatggttca tagtatcgca cctgtatcaa attcacaggg caatggagga ggggggtggat    1260 gttagagggt acttccactg gaacctaata gataacttgg agtgggctgc aggatatagg    1320
atgaggttcg gcctagttta cgttgactat gcaaccaaga ggaggtattt taggccaagc    1380
gccctggtta tgagggaggt ggctaaacag aaggctatac cggattactt agagcattac    1440
attaaaccac ctagaattga a                                              1461

<210> SEQ ID NO 40
<211> LENGTH: 487
<212> TYPE: PRT
<213> ORGANISM: Artificial Sequence
<220> FEATURE:
<223> OTHER INFORMATION: Description of Artificial Sequence: Synthetic
      mutant glycoside hydrolase family polypeptide
```

-continued of Caldivirga maquilingensis having glycosylation site
<220> FEATURE:
<221> NAME/KEY: misc_feature
<222> LOCATION: (61)..(63)
<223> OTHER INFORMATION: CARBOHYD

<400> SEQUENCE: 40

Met Gly Ile Lys Phe Pro Ser Asp Phe Arg Phe Gly Phe Ser Thr Val
1               5                   10                  15

Gly Thr Gln His Glu Met Gly Thr Pro Gly Ser Glu Phe Val Ser Asp
            20                  25                  30

Trp Tyr Val Trp Leu His Asp Pro Glu Asn Ile Ala Ser Gly Leu Val
        35                  40                  45

Ser Gly Asp Leu Pro Glu His Gly Pro Gly Tyr Trp Asn Arg Thr Lys
50                  55                  60

Gln Asp His Ser Ile Ala Arg Asp Leu Gly Leu Asp Ala Ala Trp Ile
65                  70                  75                  80

Thr Ile Glu Trp Ala Arg Val Phe Pro Lys Pro Thr Phe Asp Val Lys
                85                  90                  95

Val Lys Val Asp Glu Asp Gly Gly Asn Val Val Asp Val Glu Val
            100                 105                 110

Asn Glu Ser Ala Leu Glu Glu Leu Arg Arg Leu Ala Asp Leu Asn Ala
        115                 120                 125

Val Asn His Tyr Arg Gly Ile Leu Ser Asp Trp Lys Glu Arg Gly Gly
130                 135                 140

Leu Leu Val Ile Asn Leu Tyr His Trp Ala Met Pro Thr Trp Leu His
145                 150                 155                 160

Asp Pro Ile Ala Val Arg Lys Asn Gly Pro Asp Arg Ala Pro Ser Gly
                165                 170                 175

Trp Leu Asp Lys Arg Ser Val Ile Glu Phe Thr Lys Phe Ala Ala Phe
            180                 185                 190

Ile Ala His Glu Leu Gly Asp Leu Ala Asp Met Trp Tyr Thr Met Asn
        195                 200                 205

Glu Pro Gly Val Val Ile Thr Glu Gly Tyr Leu Tyr Val Lys Ser Gly
210                 215                 220

Phe Pro Pro Gly Tyr Leu Asp Leu Asn Ser Leu Ala Thr Ala Gly Lys
225                 230                 235                 240

His Leu Ile Glu Ala His Ala Arg Ala Tyr Asp Ala Ile Lys Ala Tyr
                245                 250                 255

Ser Arg Lys Pro Val Gly Leu Val Tyr Ser Phe Ala Asp Tyr Gln Pro
            260                 265                 270

Leu Arg Gln Gly Asp Glu Glu Ala Val Lys Glu Ala Lys Gly Leu Asp
        275                 280                 285

Tyr Ser Phe Phe Asp Ala Pro Ile Lys Gly Glu Leu Met Gly Val Thr
290                 295                 300

Arg Asp Asp Leu Lys Gly Arg Leu Asp Trp Ile Gly Val Asn Tyr Tyr
305                 310                 315                 320

Thr Arg Ala Val Leu Arg Arg Gln Asp Ala Gly Arg Ala Ser Val
                325                 330                 335

Ala Val Val Asp Gly Phe Gly Tyr Ser Cys Glu Pro Gly Gly Val Ser
            340                 345                 350

Asn Asp Arg Arg Pro Cys Ser Asp Phe Gly Trp Glu Ile Tyr Pro Glu
        355                 360                 365

Gly Val Tyr Asn Val Leu Met Asp Leu Trp Arg Arg Tyr Arg Met Pro
370                 375                 380

Met Tyr Ile Thr Glu Asn Gly Ile Ala Asp Glu His Asp Lys Trp Arg
385                 390                 395                 400

Ser Trp Phe Ile Val Ser His Leu Tyr Gln Ile His Arg Ala Met Glu
                405                 410                 415

Glu Gly Val Asp Val Arg Gly Tyr Phe His Trp Asn Leu Ile Asp Asn
            420                 425                 430

Leu Glu Trp Ala Ala Gly Tyr Arg Met Arg Phe Gly Leu Val Tyr Val
        435                 440                 445

Asp Tyr Ala Thr Lys Arg Arg Tyr Phe Arg Pro Ser Ala Leu Val Met
    450                 455                 460

Arg Glu Val Ala Lys Gln Lys Ala Ile Pro Asp Tyr Leu Glu His Tyr
465                 470                 475                 480

Ile Lys Pro Pro Arg Ile Glu
            485

<210> SEQ ID NO 41
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide encoding mutant beta-galactosidase of
      Sulfolobus acidocaldarius having glycosylation site

<400> SEQUENCE: 41
atgggtttat cattcccaaa gggtttcaaa tttggctggt ctcagtcggg attccagtct    60
gaaatgggaa ctccaggtag cgaagatccg aacagcgatt ggcacgtctg ggttcatgac   120
agggagaaca tagtctcaca ggttgtcagt ggagatttac ccgaaaatgg tccagggtac   180
tggaaccgca ctaagagatt tcatgacgaa gcagagaaaa taggactaaa tgcagtgaga   240
attaacgtag agtggagtag aatatttccc agaccactac ccaagcctga atgcaaaca    300 gggactgata aagagaacag tcctgtcatt agcgtagact aaatgagtc taagctgaga   360 gaaatggaca actacgctaa tcatgaagcg ttatcacatt acaggcaaat actggaggat   420
ctaagaaaca gaggatttca catagtactg aacatgtatc attggacttt gcccatatgg   480
ttgcacgacc ctatcagagt gaggagagga gactttacag gaccaacagg ttggttaaac   540
tccaggacag tttatgagtt cgctaggttc tcggcttacg tagcctggaa attagatgat   600
ttggcgagtg aatatgcaac aatgaatgaa cctaacgtgg tttggggagc aggttacgct   660
tttcctagag caggctttcc acctaattac cttagcttca ggctttcaga atagctaaa    720 tggaatataa ttcaggctca tgcgagggct tatgacgcca tcaagagcgt atcaaaaaag   780
agtgtaggta taatatatgc aaacacatca tattacccac tcagaccaca agataacgaa   840
gctgtggaaa tagcagagag attgaacaga tggagtttct ttgactccat tataaaggga   900
gagataacta gtgagggaca aaatgtcaga gaggacttaa ggaacaggtt agactggatt   960
ggcgtaaact attacacgag gactgtggta acaaaagctg agagtggtta tttaacccctt  1020 ccgggttatg gagatcgttg tgaaaggaac tcattgagtt tagctaacct ccctaccagt  1080
gatttcggtt gggagttctt tcctgagggt ctatatgatg tactttttga agtattggaat  1140 aggtatgggt taccattata cgtaatggag aacggtatcg ctgatgacgc tgactaccaa  1200
agaccgtatt acttagtatc acatatctac caggtgcaca gggctttaaa cgagggagta  1260
gatgtaagag gttatcttca ttggtctttg gcagataatt atgagtggtc gtcaggtttt  1320
tcaatgaggt tcggtctact taaggtagat tatctaacaa agagattgta ctggagacct  1380

-continued

```
tctgcattag tttacaggga gattactagg agtaacggta ttcctgagga gctggaacat    1440
ctaaacagag taccaccaat aaaacctttg agacat                               1476
```

<210> SEQ ID NO 42
<211> LENGTH: 492
<212> TYPE: PRT
<213> ORGANISM: Artificial Sequence
<220> FEATURE:
<223> OTHER INFORMATION: Description of Artificial Sequence: Synthetic
      mutant beta-galactosidase polypeptide of Sulfolobus
      acidocaldarius having glycosylation site
<220> FEATURE:
<221> NAME/KEY: misc_feature
<222> LOCATION: (62)..(64)
<223> OTHER INFORMATION: CARBOHYD

<400> SEQUENCE: 42

```
Met Gly Leu Ser Phe Pro Lys Gly Phe Lys Phe Gly Trp Ser Gln Ser
1               5                   10                  15

Gly Phe Gln Ser Glu Met Gly Thr Pro Gly Ser Glu Asp Pro Asn Ser
            20                  25                  30

Asp Trp His Val Trp Val His Asp Arg Glu Asn Ile Val Ser Gln Val
        35                  40                  45

Val Ser Gly Asp Leu Pro Glu Asn Gly Pro Gly Tyr Trp Asn Arg Thr
    50                  55                  60

Lys Arg Phe His Asp Glu Ala Glu Lys Ile Gly Leu Asn Ala Val Arg
65                  70                  75                  80

Ile Asn Val Glu Trp Ser Arg Ile Phe Pro Arg Pro Leu Pro Lys Pro
                85                  90                  95

Glu Met Gln Thr Gly Thr Asp Lys Glu Asn Ser Pro Val Ile Ser Val
            100                 105                 110

Asp Leu Asn Glu Ser Lys Leu Arg Glu Met Asp Asn Tyr Ala Asn His
        115                 120                 125

Glu Ala Leu Ser His Tyr Arg Gln Ile Leu Glu Asp Leu Arg Asn Arg
    130                 135                 140

Gly Phe His Ile Val Leu Asn Met Tyr His Trp Thr Leu Pro Ile Trp
145                 150                 155                 160

Leu His Asp Pro Ile Arg Val Arg Gly Asp Phe Thr Gly Pro Thr
                165                 170                 175

Gly Trp Leu Asn Ser Arg Thr Val Tyr Glu Phe Ala Arg Phe Ser Ala
            180                 185                 190

Tyr Val Ala Trp Lys Leu Asp Asp Leu Ala Ser Glu Tyr Ala Thr Met
        195                 200                 205

Asn Glu Pro Asn Val Val Trp Gly Ala Gly Tyr Ala Phe Pro Arg Ala
    210                 215                 220

Gly Phe Pro Pro Asn Tyr Leu Ser Phe Arg Leu Ser Glu Ile Ala Lys
225                 230                 235                 240

Trp Asn Ile Ile Gln Ala His Ala Arg Ala Tyr Asp Ala Ile Lys Ser
                245                 250                 255

Val Ser Lys Lys Ser Val Gly Ile Ile Tyr Ala Asn Thr Ser Tyr Tyr
            260                 265                 270

Pro Leu Arg Pro Gln Asp Asn Glu Ala Val Glu Ile Ala Glu Arg Leu
        275                 280                 285

Asn Arg Trp Ser Phe Phe Asp Ser Ile Ile Lys Gly Glu Ile Thr Ser
    290                 295                 300

Glu Gly Gln Asn Val Arg Glu Asp Leu Arg Asn Arg Leu Asp Trp Ile
```

```
                305                 310                 315                 320
        Gly Val Asn Tyr Tyr Thr Arg Thr Val Val Thr Lys Ala Glu Ser Gly
                        325                 330                 335

Tyr Leu Thr Leu Pro Gly Tyr Gly Asp Arg Cys Glu Arg Asn Ser Leu
                        340                 345                 350

Ser Leu Ala Asn Leu Pro Thr Ser Asp Phe Gly Trp Glu Phe Phe Pro
                        355                 360                 365

Glu Gly Leu Tyr Asp Val Leu Leu Lys Tyr Trp Asn Arg Tyr Gly Leu
                370                 375                 380

Pro Leu Tyr Val Met Glu Asn Gly Ile Ala Asp Asp Ala Asp Tyr Gln
        385                 390                 395                 400

Arg Pro Tyr Tyr Leu Val Ser His Ile Tyr Gln Val His Arg Ala Leu
                        405                 410                 415

Asn Glu Gly Val Asp Val Arg Gly Tyr Leu His Trp Ser Leu Ala Asp
                        420                 425                 430

Asn Tyr Glu Trp Ser Ser Gly Phe Ser Met Arg Phe Gly Leu Leu Lys
                        435                 440                 445

Val Asp Tyr Leu Thr Lys Arg Leu Tyr Trp Arg Pro Ser Ala Leu Val
                450                 455                 460

Tyr Arg Glu Ile Thr Arg Ser Asn Gly Ile Pro Glu Glu Leu Glu His
        465                 470                 475                 480

Leu Asn Arg Val Pro Pro Ile Lys Pro Leu Arg His
                        485                 490

<210> SEQ ID NO 43
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide encoding mutant beta-galactosidase
      of Sulfolobus solfataricus having glycosylation site

<400> SEQUENCE: 43
atgggttact catttccaaa tagctttagg tttggttggt cccaggccgg atttcaatca      60
gaaatgggaa caccagggtc agaagatcca aatactgact ggtataaatg ggttcatgat     120
ccagaaaaca tggcagcggg attagtaagt ggagatctac agaaaatggg ccaggctac     180 tggaaccgca ctaagacatt tcacgataat gcacaaaaaa tgggattaaa aatagctaga     240
ctaaatgtgg aatggtctag gatatttcct aatccattac aaggccaca aaactttgat     300 gaatcaaaac aagatgtgac agaggttgag ataaacgaaa acgagttaaa agacttgac     360 gagtacgcta ataagacgc attaaaccat tacagggaaa tattcaagga tcttaaagt     420 agaggacttt actttatact aaacatgtat cattggccat acctctatg gttacacgac     480 ccaataagag taagaagagg agattttact ggaccaagtg gttggctaag tactagaaca     540
gtttacgagt cgctagatt ctcagcttat atagcttgga aattcgatga tctagtggat     600
gagtactcaa caatgaatga acctaacgtt gttggaggtt taggatacgt tggtgttaag     660
tccggttttc ccccaggata cctaagcttt gaactttccc gtagggcaat gtataacatc     720
attcaagctc acgcaagagc gtatgatggg ataaagagtg tttctaaaaa accagttgga     780
attatttacg ctaatagctc attccagccg ttaacggata agatatgga agcggtagag     840 atggctgaaa atgataatag atggtggttc tttgatgcta taataagagg tgagatcacc     900
agaggaaacg agaagattgt aagagatgac ctaaagggta gattggattg gattggagtt     960
```

-continued

```
aattattaca ctaggactgt tgtgaagagg actgaaaagg gatacgttag cttaggaggt   1020
tacggtcacg gatgtgagag gaactctgta agtttagcgg gattaccaac cagcgacttc   1080
ggctgggagt tcttcccaga aggtttatat gacgttttga cgaaatactg gaatagatat   1140
catctctata tgtacgttac tgaaaatggt attgcggatg atgccgatta tcaaaggccc   1200
tattatttag tatctcacgt ttatcaagtt catagagcaa taaatagtgg tgcagatgtt   1260
agagggtatt tacattggtc tctagctgat aattacgaat gggcttcagg attctctatg   1320
aggtttggtc tgttaaaggt cgattacaac actaagagac tatactggag accctcagca   1380
ctagtatata gggaaatcgc cacaaatggc gcaataactg atgaaataga gcacttaaat   1440
agcgtacctc cagtaaagcc attaaggcac                                    1470
```

<210> SEQ ID NO 44
<211> LENGTH: 490
<212> TYPE: PRT
<213> ORGANISM: Artificial Sequence
<220> FEATURE:
<223> OTHER INFORMATION: Description of Artificial Sequence: Synthetic mutant beta-galactosidase polypeptide of Sulfolobus solfataricus having glycosylation site
<220> FEATURE:
<221> NAME/KEY: misc_feature
<222> LOCATION: (62)..(64)
<223> OTHER INFORMATION: CARBOHYD

<400> SEQUENCE: 44

```
Met Gly Tyr Ser Phe Pro Asn Ser Phe Arg Phe Gly Trp Ser Gln Ala
1               5                   10                  15

Gly Phe Gln Ser Glu Met Gly Thr Pro Gly Ser Glu Asp Pro Asn Thr
            20                  25                  30

Asp Trp Tyr Lys Trp Val His Asp Pro Glu Asn Met Ala Ala Gly Leu
        35                  40                  45

Val Ser Gly Asp Leu Pro Glu Asn Gly Pro Gly Tyr Trp Asn Arg Thr
    50                  55                  60

Lys Thr Phe His Asp Asn Ala Gln Lys Met Gly Leu Lys Ile Ala Arg
65                  70                  75                  80

Leu Asn Val Glu Trp Ser Arg Ile Phe Pro Asn Pro Leu Pro Arg Pro
                85                  90                  95

Gln Asn Phe Asp Glu Ser Lys Gln Asp Val Thr Glu Val Glu Ile Asn
            100                 105                 110

Glu Asn Glu Leu Lys Arg Leu Asp Glu Tyr Ala Asn Lys Asp Ala Leu
        115                 120                 125

Asn His Tyr Arg Glu Ile Phe Lys Asp Leu Lys Ser Arg Gly Leu Tyr
    130                 135                 140

Phe Ile Leu Asn Met Tyr His Trp Pro Leu Pro Leu Trp Leu His Asp
145                 150                 155                 160

Pro Ile Arg Val Arg Arg Gly Asp Phe Thr Gly Pro Ser Gly Trp Leu
                165                 170                 175

Ser Thr Arg Thr Val Tyr Glu Phe Ala Arg Phe Ser Ala Tyr Ile Ala
            180                 185                 190

Trp Lys Phe Asp Asp Leu Val Asp Glu Tyr Ser Thr Met Asn Glu Pro
        195                 200                 205

Asn Val Val Gly Gly Leu Gly Tyr Val Gly Val Lys Ser Gly Phe Pro
    210                 215                 220

Pro Gly Tyr Leu Ser Phe Glu Leu Ser Arg Arg Ala Met Tyr Asn Ile
225                 230                 235                 240
```

```
Ile Gln Ala His Ala Arg Ala Tyr Asp Gly Ile Lys Ser Val Ser Lys
            245                 250                 255

Lys Pro Val Gly Ile Ile Tyr Ala Asn Ser Ser Phe Gln Pro Leu Thr
        260                 265                 270

Asp Lys Asp Met Glu Ala Val Glu Met Ala Glu Asn Asp Asn Arg Trp
    275                 280                 285

Trp Phe Phe Asp Ala Ile Ile Arg Gly Glu Ile Thr Arg Gly Asn Glu
290                 295                 300

Lys Ile Val Arg Asp Asp Leu Lys Gly Arg Leu Asp Trp Ile Gly Val
305                 310                 315                 320

Asn Tyr Tyr Thr Arg Thr Val Val Lys Arg Thr Glu Lys Gly Tyr Val
                325                 330                 335

Ser Leu Gly Gly Tyr Gly His Gly Cys Glu Arg Asn Ser Val Ser Leu
            340                 345                 350

Ala Gly Leu Pro Thr Ser Asp Phe Gly Trp Glu Phe Phe Pro Glu Gly
        355                 360                 365

Leu Tyr Asp Val Leu Thr Lys Tyr Trp Asn Arg Tyr His Leu Tyr Met
    370                 375                 380

Tyr Val Thr Glu Asn Gly Ile Ala Asp Ala Asp Tyr Gln Arg Pro
385                 390                 395                 400

Tyr Tyr Leu Val Ser His Val Tyr Gln Val His Arg Ala Ile Asn Ser
                405                 410                 415

Gly Ala Asp Val Arg Gly Tyr Leu His Trp Ser Leu Ala Asp Asn Tyr
            420                 425                 430

Glu Trp Ala Ser Gly Phe Ser Met Arg Phe Gly Leu Leu Lys Val Asp
        435                 440                 445

Tyr Asn Thr Lys Arg Leu Tyr Trp Arg Pro Ser Ala Leu Val Tyr Arg
    450                 455                 460

Glu Ile Ala Thr Asn Gly Ala Ile Thr Asp Glu Ile Glu His Leu Asn
465                 470                 475                 480

Ser Val Pro Pro Val Lys Pro Leu Arg His
                485                 490

<210> SEQ ID NO 45
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide encoding mutant beta-galactosidase
      of Picrophilus torridus having glycosylation site

<400> SEQUENCE: 45
atgggtttac ccaagaactt tttacttggc ttttctctgg ctggctttca gtctgaaatg      60
ggcatatcag atcctgatag caattcagat tggtggttat gggtacatga cccggtgaat     120
ataaggactg gacttgtatc tggtgactta cctgaaaatg aataggata ctggaaccgc      180 actaaaaaat ataatggtct ggctgttcaa acaggaatga atgctgcaag gcttggagtt     240
gaatggagca ggatatttcc aaaaagtact gaagaagtaa aggtgatgga agattacaaa     300
gatgatgatt taatttccgt ggatgttaat gagggaagtc ttgaaaaact tgacagactg     360
gcaaatcaaa aggcaattaa tagatatatg gaaatcttca ataatatcaa ggaaaataat     420
atgacgctaa tagtgaatgt ttaccattgg ccaataccaa tatatcttca cgatccaata     480
gaagctagga atagtggact ttcaaataaa agaaatggct ggcttaatca taaaaccgtt     540
gtggaatttg taaatatgc aaaatatctg gcatggaaat ttagcgatgt ggcagatatg     600
```

```
ttttctataa tgaatgagcc aaacgttgta tttggtaatg gatattttaa tgttaaatca    660
gggttcccac cagcatttcc aagtgtgcat ggcggttttgc ttgcaaaaaa acatgaaatt   720
gaggctatag caagatcata cgacgccatg aaggagatta caaaaaaacc agttggtcta   780
attatggcaa attcagatgt acaaccacta acagatgagg ataaagaagc agcagaaatg   840
gctacttaca atgatcgcta ttcattcata gatccgctaa gagttggtga gatgaaatgg   900
gctgatgagg ttactgcagg taatccaatt ggtgaaaaga gcaacatcga tagatctgat   960
ctaaaaaata agctagactg gataggtgtt aactattata caagggccgt tgtaaaaaaa  1020
tctggaaacg gatatacaac attaaaagga tatggacact ctgcaaccgc tggcatgcca  1080
agtagggccg gaagggatgt aagtgacttt ggctgggaat tttatccaga aggtcttgta  1140
aacgtcttat catcatactg gaaaagatat cacattccaa tgattgtgac tgaaaatggt  1200
gttgctgact ctattgatag acttagacca aggtaccttg tgtcacatat aaagtctgtt  1260
gaaaaggctt tatctatggg tatggatatt agggatatc ttcactggtc tctgattgat  1320
aactatgaat gggcatcagg tttttcaatg aaatttgggc tttatggtat tgatttgaac  1380
aataaaaaga ttcaacacag accaagtgca ctggtattta agaaattgc aaatgccaac  1440 ggagtcccgg aggaatttga atggatggca gaccagcatc agaactca              1488
```

<210> SEQ ID NO 46
<211> LENGTH: 496
<212> TYPE: PRT
<213> ORGANISM: Artificial Sequence
<220> FEATURE:
<223> OTHER INFORMATION: Description of Artificial Sequence: Synthetic
      mutant beta-galactosidase polypeptide of
      Picrophilus torridus having glycosylation site
<220> FEATURE:
<221> NAME/KEY: misc_feature
<222> LOCATION: (59)..(61)
<223> OTHER INFORMATION: CARBOHYD

<400> SEQUENCE: 46

Met Gly Leu Pro Lys Asn Phe Leu Leu Gly Phe Ser Leu Ala Gly Phe
1               5                   10                  15

Gln Ser Glu Met Gly Ile Ser Asp Pro Asp Ser Asn Ser Asp Trp Trp
            20                  25                  30

Leu Trp Val His Asp Pro Val Asn Ile Arg Thr Gly Leu Val Ser Gly
        35                  40                  45

Asp Leu Pro Glu Asn Gly Ile Gly Tyr Trp Asn Arg Thr Lys Lys Tyr
    50                  55                  60

Asn Gly Leu Ala Val Gln Thr Gly Met Asn Ala Ala Arg Leu Gly Val
65                  70                  75                  80

Glu Trp Ser Arg Ile Phe Pro Lys Ser Thr Glu Glu Val Lys Val Met
                85                  90                  95

Glu Asp Tyr Lys Asp Asp Asp Leu Ile Ser Val Asp Val Asn Glu Gly
            100                 105                 110

Ser Leu Glu Lys Leu Asp Arg Leu Ala Asn Gln Lys Ala Ile Asn Arg
        115                 120                 125

Tyr Met Glu Ile Phe Asn Asn Ile Lys Glu Asn Met Thr Leu Ile
    130                 135                 140

Val Asn Val Tyr His Trp Pro Ile Pro Ile Tyr Leu His Asp Pro Ile
145                 150                 155                 160

Glu Ala Arg Asn Ser Gly Leu Ser Asn Lys Arg Asn Gly Trp Leu Asn
                165                 170                 175

His Lys Thr Val Val Glu Phe Val Lys Tyr Ala Lys Tyr Leu Ala Trp
            180                 185                 190

Lys Phe Ser Asp Val Ala Asp Met Phe Ser Ile Met Asn Glu Pro Asn
        195                 200                 205

Val Val Phe Gly Asn Gly Tyr Phe Asn Val Lys Ser Gly Phe Pro Pro
    210                 215                 220

Ala Phe Pro Ser Val His Gly Gly Leu Leu Ala Lys Lys His Glu Ile
225                 230                 235                 240

Glu Ala Ile Ala Arg Ser Tyr Asp Ala Met Lys Glu Ile Thr Lys Lys
                245                 250                 255

Pro Val Gly Leu Ile Met Ala Asn Ser Asp Val Gln Pro Leu Thr Asp
            260                 265                 270

Glu Asp Lys Glu Ala Ala Glu Met Ala Thr Tyr Asn Asp Arg Tyr Ser
        275                 280                 285

Phe Ile Asp Pro Leu Arg Val Gly Glu Met Lys Trp Ala Asp Glu Val
    290                 295                 300

Thr Ala Gly Asn Pro Ile Gly Glu Lys Ser Asn Ile Asp Arg Ser Asp
305                 310                 315                 320

Leu Lys Asn Lys Leu Asp Trp Ile Gly Val Asn Tyr Tyr Thr Arg Ala
                325                 330                 335

Val Val Lys Lys Ser Gly Asn Gly Tyr Thr Thr Leu Lys Gly Tyr Gly
            340                 345                 350

His Ser Ala Thr Ala Gly Met Pro Ser Arg Ala Gly Arg Asp Val Ser
        355                 360                 365

Asp Phe Gly Trp Glu Phe Tyr Pro Glu Gly Leu Val Asn Val Leu Ser
    370                 375                 380

Ser Tyr Trp Lys Arg Tyr His Ile Pro Met Ile Val Thr Glu Asn Gly
385                 390                 395                 400

Val Ala Asp Ser Ile Asp Arg Leu Arg Pro Arg Tyr Leu Val Ser His
                405                 410                 415

Ile Lys Ser Val Glu Lys Ala Leu Ser Met Gly Met Asp Ile Arg Gly
            420                 425                 430

Tyr Leu His Trp Ser Leu Ile Asp Asn Tyr Glu Trp Ala Ser Gly Phe
        435                 440                 445

Ser Met Lys Phe Gly Leu Tyr Gly Ile Asp Leu Asn Asn Lys Lys Ile
    450                 455                 460

Gln His Arg Pro Ser Ala Leu Val Phe Lys Glu Ile Ala Asn Ala Asn
465                 470                 475                 480

Gly Val Pro Glu Glu Phe Glu Trp Met Ala Asp Gln His Gln Asn Ser
                485                 490                 495

<210> SEQ ID NO 47
<211> LENGTH: 1443
<212> TYPE: DNA
<213> ORGANISM: Artificial Sequence
<220> FEATURE:
<223> OTHER INFORMATION: Description of Artificial Sequence: Synthetic
    polynucleotide encoding mutant beta-galactosidase
    of Thermoplasma volcanium having glycosylation site

<400> SEQUENCE: 47
atggtagaaa acaatttttcc agaggatttc aaatttggtt ggtcacagtc aggttttcaa      60
tcggagatgg gctatgataa cgcaatggac gataaaagtg actggtatgt ctgggttcat     120
gataaagaaa acatccaatc agggcttgta agcggagaca tgcccgaaaa tggtccgggt     180

```
tactggaacc gcactaaatc attccatgaa gctgcacaga atatgggatt aaaaatggca    240
agaatcggag ttgaatggtc aagattattc ccggaacctt tcccggaaaa aataatggca    300
gatgcaaaaa ataattcctt agaaataaac aataacattc tttcagaact tgataaatat    360
gtcaataaag atgcactcaa ccattacatt gagatattta atgatatcaa aaatagaaat    420
atagatttaa taattaatat gtaccactgg ccacttcctg tatggctaag cgatcctgta    480
tctgttagaa aaggaataaa aacagaaaga tcaggctggc tgaatgacag atagttcaa     540 ttgtttgctt tattctcctc gtatatagta tataaaatgg aagatctggc agttgcattt    600
tcaaccatga atgaacctaa tgttgtttat ggaaatggtt ttataaatat caaatcaggt    660
tttccgcctt cctatctcag ttcagaattt gcatctaaag ttaagaacaa tatattaaaa    720
gcacattctc ttgcatacga ttctatgaaa aaaattacgg ataaacctgt gggaataatt    780
tatgcaaaca catattttac gcctttggac ccggaaaaag aatgatgc tattgctaaa      840 gcagacagtg atgcgaaatg gtcatttttt gatccattaa taaaggaga taatcactt      900 ggaattaatg gcaataaact agattggatc ggaattaatt attatacaag gacaatgtta    960
aggaaagacg gagatggcta tatttcatta aaaggctatg gtcattcagg ttctcctaat   1020
actgtaacaa acgataaaag accaacaagt gatataggat gggaattta tccggaggga   1080 ttggaatatg taattatgaa ttactggaac aggtataaat tgcctatgta cgtaacagaa   1140
aatggcatag ccgataatgg ggattatcag aggccttat atttagtttc acacattgca   1200
agtgtactga gggcaataaa taaggagcc aatgtaaagg ttatttgca ctggtcctta    1260 gttgataatt atgaatgggc attgggattt agcccgaaat tggttttaat aggatacgat   1320
gaaaataaaa aactatactg gaggccaagt gctcttgttt ataaggaaat agcaacaaaa   1380
aattgcatat ccccagaatt aaagcacctc gattcaatac cgcctataaa tggtttaaga   1440
aaa                                                                  1443
```

<210> SEQ ID NO 48
<211> LENGTH: 481
<212> TYPE: PRT
<213> ORGANISM: Artificial Sequence
<220> FEATURE:
<223> OTHER INFORMATION: Description of Artificial Sequence: Synthetic
      mutant beta-galactosidase polypeptide of
      Thermoplasma volcanium aggregans having glycosylation
      site
<220> FEATURE:
<221> NAME/KEY: misc_feature
<222> LOCATION: (63)..(65)
<223> OTHER INFORMATION: CARBOHYD

<400> SEQUENCE: 48

```
Met Val Glu Asn Asn Phe Pro Glu Asp Phe Lys Phe Gly Trp Ser Gln
1               5                   10                  15

Ser Gly Phe Gln Ser Glu Met Gly Tyr Asp Asn Ala Met Asp Asp Lys
            20                  25                  30

Ser Asp Trp Tyr Val Trp Val His Asp Lys Glu Asn Ile Gln Ser Gly
        35                  40                  45

Leu Val Ser Gly Asp Met Pro Glu Asn Gly Pro Gly Tyr Trp Asn Arg
    50                  55                  60

Thr Lys Ser Phe His Glu Ala Ala Gln Asn Met Gly Leu Lys Met Ala
65                  70                  75                  80

Arg Ile Gly Val Glu Trp Ser Arg Leu Phe Pro Glu Pro Phe Pro Glu
                85                  90                  95
```

```
Lys Ile Met Ala Asp Ala Lys Asn Asn Ser Leu Glu Ile Asn Asn Asn
                100                 105                 110

Ile Leu Ser Glu Leu Asp Lys Tyr Val Asn Lys Asp Ala Leu Asn His
            115                 120                 125

Tyr Ile Glu Ile Phe Asn Asp Ile Lys Asn Arg Asn Ile Asp Leu Ile
        130                 135                 140

Ile Asn Met Tyr His Trp Pro Leu Pro Val Trp Leu Ser Asp Pro Val
145                 150                 155                 160

Ser Val Arg Lys Gly Ile Lys Thr Glu Arg Ser Gly Trp Leu Asn Asp
                165                 170                 175

Arg Ile Val Gln Leu Phe Ala Leu Phe Ser Ser Tyr Ile Val Tyr Lys
            180                 185                 190

Met Glu Asp Leu Ala Val Ala Phe Ser Thr Met Asn Glu Pro Asn Val
        195                 200                 205

Val Tyr Gly Asn Gly Phe Ile Asn Ile Lys Ser Gly Phe Pro Pro Ser
        210                 215                 220

Tyr Leu Ser Ser Glu Phe Ala Ser Lys Val Lys Asn Asn Ile Leu Lys
225                 230                 235                 240

Ala His Ser Leu Ala Tyr Asp Ser Met Lys Lys Ile Thr Asp Lys Pro
                245                 250                 255

Val Gly Ile Ile Tyr Ala Asn Thr Tyr Phe Thr Pro Leu Asp Pro Glu
            260                 265                 270

Lys Asp Asn Asp Ala Ile Ala Lys Asp Ser Asp Ala Lys Trp Ser
        275                 280                 285

Phe Phe Asp Pro Leu Ile Lys Gly Asp Lys Ser Leu Gly Ile Asn Gly
        290                 295                 300

Asn Lys Leu Asp Trp Ile Gly Ile Asn Tyr Tyr Thr Arg Thr Met Leu
305                 310                 315                 320

Arg Lys Asp Gly Asp Gly Tyr Ile Ser Leu Lys Gly Tyr Gly His Ser
                325                 330                 335

Gly Ser Pro Asn Thr Val Thr Asn Asp Lys Arg Pro Thr Ser Asp Ile
            340                 345                 350

Gly Trp Glu Phe Tyr Pro Glu Gly Leu Glu Tyr Val Ile Met Asn Tyr
        355                 360                 365

Trp Asn Arg Tyr Lys Leu Pro Met Tyr Val Thr Glu Asn Gly Ile Ala
370                 375                 380

Asp Asn Gly Asp Tyr Gln Arg Pro Tyr Tyr Leu Val Ser His Ile Ala
385                 390                 395                 400

Ser Val Leu Arg Ala Ile Asn Lys Gly Ala Asn Val Lys Gly Tyr Leu
                405                 410                 415

His Trp Ser Leu Val Asp Asn Tyr Glu Trp Ala Leu Gly Phe Ser Pro
            420                 425                 430

Lys Phe Gly Leu Ile Gly Tyr Asp Glu Asn Lys Lys Leu Tyr Trp Arg
        435                 440                 445

Pro Ser Ala Leu Val Tyr Lys Glu Ile Ala Thr Lys Asn Cys Ile Ser
450                 455                 460

Pro Glu Leu Lys His Leu Asp Ser Ile Pro Pro Ile Asn Gly Leu Arg
465                 470                 475                 480

Lys

<210> SEQ ID NO 49
<211> LENGTH: 1404
<212> TYPE: DNA
<213> ORGANISM: Artificial Sequence
```

<220> FEATURE:
<223> OTHER INFORMATION: Description of Artificial Sequence: Synthetic polynucleotide encoding mutant glycoside hydrolase family protein of Fervidobacterium nodosum having glycosylation site

<400> SEQUENCE: 49

```
atgggtatgt tccgaaaga ttttttattt ggtgtttcga tgtctgggtt tcagtttgag     60
atgggaaatc ctcaagatgc agaagaggtt gatctaaata cagattggta tgtatgggtt    120
agggatattg gaaatattgt aaatggagtc gtaagtgggg acttgcctga aaatggttca    180
tggtactgga accgcactgg caaagtccac caattagctg ccgattttgg gatggatgta    240
atacgaattg gaaccgaatg gtctaggatt tcccagttta gtacgcaaag tgttgagtac    300
ggctcaccgg atatgctcga aaaattggat aaattagcaa accaaaaagc ggtaagtcat    360
tacaggaaaa taatggagga tataaaagca aaggggttaa aattgttcgt taacctttac    420
cactttactt tacctatttg gttgcacgac cctatagctg ttcacaaagg tgagaagaca    480
gataaaattg gttggatttc tgatgctaca cctattgagt ttgcgaagta tgcagagtac    540
atggcgtgga aatttgccga tatagttgat atgtgggctt ctatgaacga accacacgtt    600
gtaagtcagc ttggatattt tgcaataaat gcgggatttc caccaagtta tttttaatcct   660
tcatggtata tcaaaagttt agaaaacgaa gcgaaagcac ataacttatc ttatgatgct    720
ataaaaaagt atacaaataa tcctgttgga gttatatact cttttacatg gtacgatact    780
gttaataaag atgacaagga atcttttgaa aatgctatgg atctcacaaa ttggcgattt    840
atagatatgt aaaagataa aactgattac ataggtgtaa attattacac aagagcggtt    900
atcgatagac ttcccaccac tattgacttt ggcgaattta aaatgaattg gtatactttg    960
agaggttacg gttattcttg cgaagaagga ggattctcac tctccggaag gccggcaagc   1020
gaatttggat gggaaatata ccctgaaggg ctgtacaata ttttgataca tgtttataat   1080
agatacaaaa aagatattta tgttacggag aacggtatag ctgattcgaa ggataaatac   1140
agaagtcttt ttatcatatc gcatctttat gctatagaaa aagcattaaa cgaaggaata   1200
ccaataaaag gttattgca ctggtcgatt atagacaatt cgaatgggc gaagggctac    1260
agtaaaagat ttggacttgc ttacacagat ttgtcaacca aaaaatatat acctagacct   1320
tctatgtaca tttttagaga gataataaag gataaatcaa tcgacaaatt caaaggttac   1380
gatccatata acttgatgaa attc                                           1404
```

<210> SEQ ID NO 50
<211> LENGTH: 468
<212> TYPE: PRT
<213> ORGANISM: Artificial Sequence
<220> FEATURE:
<223> OTHER INFORMATION: Description of Artificial Sequence: Synthetic mutant glycoside hydrolase family polypeptide Fervidobacterium nodosum having glycosylation site
<220> FEATURE:
<221> NAME/KEY: misc_feature
<222> LOCATION: (64)..(66)
<223> OTHER INFORMATION: CARBOHYD

<400> SEQUENCE: 50

Met Gly Met Phe Pro Lys Asp Phe Leu Phe Gly Val Ser Met Ser Gly
1               5                   10                  15

Phe Gln Phe Glu Met Gly Asn Pro Gln Asp Ala Glu Glu Val Asp Leu
            20                  25                  30

Asn Thr Asp Trp Tyr Val Trp Val Arg Asp Ile Gly Asn Ile Val Asn

```
                35                  40                  45
Gly Val Val Ser Gly Asp Leu Pro Glu Asn Gly Ser Trp Tyr Trp Asn
 50                  55                  60

Arg Thr Gly Lys Val His Gln Leu Ala Ala Asp Phe Gly Met Asp Val
 65                  70                  75                  80

Ile Arg Ile Gly Thr Glu Trp Ser Arg Ile Phe Pro Val Ser Thr Gln
                 85                  90                  95

Ser Val Glu Tyr Gly Ser Pro Asp Met Leu Glu Lys Leu Asp Lys Leu
                100                 105                 110

Ala Asn Gln Lys Ala Val Ser His Tyr Arg Lys Ile Met Glu Asp Ile
                115                 120                 125

Lys Ala Lys Gly Leu Lys Leu Phe Val Asn Leu Tyr His Phe Thr Leu
130                 135                 140

Pro Ile Trp Leu His Asp Pro Ile Ala Val His Lys Gly Glu Lys Thr
145                 150                 155                 160

Asp Lys Ile Gly Trp Ile Ser Asp Ala Thr Pro Ile Glu Phe Ala Lys
                165                 170                 175

Tyr Ala Glu Tyr Met Ala Trp Lys Phe Ala Asp Ile Val Asp Met Trp
                180                 185                 190

Ala Ser Met Asn Glu Pro His Val Val Ser Gln Leu Gly Tyr Phe Ala
                195                 200                 205

Ile Asn Ala Gly Phe Pro Pro Ser Tyr Phe Asn Pro Ser Trp Tyr Ile
210                 215                 220

Lys Ser Leu Glu Asn Glu Ala Lys Ala His Asn Leu Ser Tyr Asp Ala
225                 230                 235                 240

Ile Lys Lys Tyr Thr Asn Asn Pro Val Gly Val Ile Tyr Ser Phe Thr
                245                 250                 255

Trp Tyr Asp Thr Val Asn Lys Asp Lys Glu Ser Phe Glu Asn Ala
                260                 265                 270

Met Asp Leu Thr Asn Trp Arg Phe Ile Asp Met Val Lys Asp Lys Thr
                275                 280                 285

Asp Tyr Ile Gly Val Asn Tyr Tyr Thr Arg Ala Val Ile Asp Arg Leu
                290                 295                 300

Pro Thr Thr Ile Asp Phe Gly Glu Phe Lys Met Asn Trp Tyr Thr Leu
305                 310                 315                 320

Arg Gly Tyr Gly Tyr Ser Cys Glu Glu Gly Phe Ser Leu Ser Gly
                325                 330                 335

Arg Pro Ala Ser Glu Phe Gly Trp Glu Ile Tyr Pro Glu Gly Leu Tyr
                340                 345                 350

Asn Ile Leu Ile His Val Tyr Asn Arg Tyr Lys Lys Asp Ile Tyr Val
                355                 360                 365

Thr Glu Asn Gly Ile Ala Asp Ser Lys Asp Lys Tyr Arg Ser Leu Phe
                370                 375                 380

Ile Ile Ser His Leu Tyr Ala Ile Glu Lys Ala Leu Asn Glu Gly Ile
385                 390                 395                 400

Pro Ile Lys Gly Tyr Leu His Trp Ser Ile Ile Asp Asn Phe Glu Trp
                405                 410                 415

Ala Lys Gly Tyr Ser Lys Arg Phe Gly Leu Ala Tyr Thr Asp Leu Ser
                420                 425                 430

Thr Lys Lys Tyr Ile Pro Arg Pro Ser Met Tyr Ile Phe Arg Glu Ile
                435                 440                 445

Ile Lys Asp Lys Ser Ile Asp Lys Phe Lys Gly Tyr Asp Pro Tyr Asn
450                 455                 460
```

Leu Met Lys Phe
465

<210> SEQ ID NO 51
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide encoding mutant beta-glucosidase
      having glycosylation site

<400> SEQUENCE: 51

```
atggcaaagt tcccaaaaaa cttcatgttt ggatattctt ggtctggttt ccagtttgag      60
atgggactgc caggaagtga agtggaaagc gactggtggg tgtgggttaa cgacacggag     120
aacatagcat caggtctagt aagtggagat ctaccagaga acggcccagc atattggaac     180
cgcactaagc aagatcatga cattgcagaa aagctaggaa tggattgtat tagaggtggc     240
attgagtggg caagaatttt tccaaagcca acatttgacg ttaaagttga tgtggaaaag     300
gatgaagaag gcaacataat ttccgtagac gttccagaga gtacaataaa agagctagag     360
aaaattgcca acatggaggc ccttgaacat tatcgcaaga tttactcaga ctggaaggag     420
aggggcaaaa ccttcatatt aaacctctac cactggcctc ttccattatg gattcatgac     480
ccaattgcag taaggaaact tggcccggat agggctcctg caggatggtt agatgagaag     540
acagtggtag agtttgtgaa gtttgccgcc ttcgttgctt atcaccttga tgacctcgtt     600
gacatgtgga gcacaatgaa cgaaccaaac gtagtctaca atcaaggtta cattaatcta     660
cgttcaggat ttccaccagg atatctaagc tttgaagcag cagaaaaggc aaaattcaac     720
ttaattcagg ctcacatcgg agcatatgat gccataaaag agtattcaga aaaatccgtg     780
ggagtgatat acgcctttgc ttggcacgat cctctagcgg aggagtataa ggatgaagta     840
gaggaaatca gaaagaaaga ctatgagttt gtaacaattc tacactcaaa aggaaagcta     900
gactggatcg gcgtaaacta ctactccagg ctggtatatg gagccaaaga tggacaccta     960
gttccttttac ctggatatgg atttatgagt gagagaggag gatttgcaaa gtcaggaaga    1020
cctgctagtg actttggatg ggaaatgtac ccagagggcc ttgagaacct tcttaagtat    1080
ttaaacaatg cctacgagct accaatgata attacagaga acggtatggc cgatgcagca    1140
gatagataca ggccacacta tctcgtaagc catctaaagg cagtttacaa tgctatgaaa    1200
gaaggtgctg atgttagagg gtatctccac tggtctctaa cagacaacta cgaatgggcc    1260
caagggttca ggatgagatt tggattggtt tacgtggatt tcgagacaaa gaagagatat    1320
ttaaggccaa gcgccctggt attcagagaa atagccactc aaaaagaaat tccagaagaa    1380
ttagctcacc tcgcagacct caaatttgtt acaagaaag                           1419
```

<210> SEQ ID NO 52
<211> LENGTH: 473
<212> TYPE: PRT
<213> ORGANISM: Artificial Sequence
<220> FEATURE:
<223> OTHER INFORMATION: Description of Artificial Sequence: Synthetic
      mutant beta-glucosidase polypeptide having
      glycosylation site
<220> FEATURE:
<221> NAME/KEY: misc_feature
<222> LOCATION: (37)..(39)
<223> OTHER INFORMATION: CARBOHYD
<220> FEATURE:
<221> NAME/KEY: misc_feature

<222> LOCATION: (60)..(62)
<223> OTHER INFORMATION: CARBOHYD

<400> SEQUENCE: 52

```
Met Ala Lys Phe Pro Lys Asn Phe Met Phe Gly Tyr Ser Trp Ser Gly
1               5                   10                  15

Phe Gln Phe Glu Met Gly Leu Pro Gly Ser Val Glu Ser Asp Trp
            20                  25                  30

Trp Val Trp Val Asn Asp Thr Glu Asn Ile Ala Ser Gly Leu Val Ser
        35                  40                  45

Gly Asp Leu Pro Glu Asn Gly Pro Ala Tyr Trp Asn Arg Thr Lys Gln
50                  55                  60

Asp His Asp Ile Ala Glu Lys Leu Gly Met Asp Cys Ile Arg Gly Gly
65                  70                  75                  80

Ile Glu Trp Ala Arg Ile Phe Pro Lys Pro Thr Phe Asp Val Lys Val
                85                  90                  95

Asp Val Glu Lys Asp Glu Glu Gly Asn Ile Ile Ser Val Asp Val Pro
            100                 105                 110

Glu Ser Thr Ile Lys Glu Leu Glu Lys Ile Ala Asn Met Glu Ala Leu
        115                 120                 125

Glu His Tyr Arg Lys Ile Tyr Ser Asp Trp Lys Glu Arg Gly Lys Thr
130                 135                 140

Phe Ile Leu Asn Leu Tyr His Trp Pro Leu Pro Leu Trp Ile His Asp
145                 150                 155                 160

Pro Ile Ala Val Arg Lys Leu Gly Pro Asp Arg Ala Pro Ala Gly Trp
                165                 170                 175

Leu Asp Glu Lys Thr Val Val Glu Phe Val Lys Phe Ala Ala Phe Val
            180                 185                 190

Ala Tyr His Leu Asp Asp Leu Val Asp Met Trp Ser Thr Met Asn Glu
        195                 200                 205

Pro Asn Val Val Tyr Asn Gln Gly Tyr Ile Asn Leu Arg Ser Gly Phe
210                 215                 220

Pro Pro Gly Tyr Leu Ser Phe Glu Ala Ala Glu Lys Ala Lys Phe Asn
225                 230                 235                 240

Leu Ile Gln Ala His Ile Gly Ala Tyr Asp Ala Ile Lys Glu Tyr Ser
                245                 250                 255

Glu Lys Ser Val Gly Val Ile Tyr Ala Phe Ala Trp His Asp Pro Leu
            260                 265                 270

Ala Glu Glu Tyr Lys Asp Glu Val Glu Glu Ile Arg Lys Lys Asp Tyr
        275                 280                 285

Glu Phe Val Thr Ile Leu His Ser Lys Gly Lys Leu Asp Trp Ile Gly
290                 295                 300

Val Asn Tyr Tyr Ser Arg Leu Val Tyr Gly Ala Lys Asp Gly His Leu
305                 310                 315                 320

Val Pro Leu Pro Gly Tyr Gly Phe Met Ser Glu Arg Gly Gly Phe Ala
                325                 330                 335

Lys Ser Gly Arg Pro Ala Ser Asp Phe Gly Trp Glu Met Tyr Pro Glu
            340                 345                 350

Gly Leu Glu Asn Leu Leu Lys Tyr Leu Asn Asn Ala Tyr Glu Leu Pro
        355                 360                 365

Met Ile Ile Thr Glu Asn Gly Met Ala Asp Ala Asp Arg Tyr Arg
370                 375                 380

Pro His Tyr Leu Val Ser His Leu Lys Ala Val Tyr Asn Ala Met Lys
385                 390                 395                 400
```

Glu Gly Ala Asp Val Arg Gly Tyr Leu His Trp Ser Leu Thr Asp Asn
            405                 410                 415

Tyr Glu Trp Ala Gln Gly Phe Arg Met Arg Phe Gly Leu Val Tyr Val
        420                 425                 430

Asp Phe Glu Thr Lys Lys Arg Tyr Leu Arg Pro Ser Ala Leu Val Phe
            435                 440                 445

Arg Glu Ile Ala Thr Gln Lys Glu Ile Pro Glu Glu Leu Ala His Leu
    450                 455                 460

Ala Asp Leu Lys Phe Val Thr Arg Lys
465                 470

<210> SEQ ID NO 53
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide encoding mutant beta-glucosidase
      having glycosylation site

<400> SEQUENCE: 53
atggcaaagt cccaaaaaaa cttcatgttt ggatattctt ggtctggttt ccagtttgag     60
atgggactgc aggaagtga agtggaaagc gactggtggg tgtgggttca cgacaaggag    120
aacatagcat caggtctagt aagtggagat ctaccagaga acggcccagc atattggaac    180
cgcactaagc aagatcatga cattgcagaa aagctaggaa tggattgtat tagaggtggc    240
attgagtggg caagaatttt tccaaagcca acatttgacg ttaaagttga tgtggaaaag    300
gatgaagaag gcaacataat ttccgtagac gttccagaga gtacaataaa agagctagag    360
aaaattgcca acatggaggc ccttgaacat tatcgcaaga tttactcaga ctggaaggag    420
aggggcaaaa ccttcatatt aaacctctac cactggcctc ttccattatg gattcatgac    480
ccaattgcag taaggaaact ggcccggat agggctcctg caggatggtt agatgagaag    540
acagtggtag agtttgtgaa gtttgccgcc ttcgttgctt atcaccttga tgacctcgtt    600
gacatgtgga gcacaatgaa cgaaccaaac gtagtctaca atcaaggtta cattaatcta    660
cgttcaggat ttccaccagg atatctaaac tttacagcag cagaaaaggc aaaattcaac    720
ttaattcagg ctcacatcgg agcatatgat gccataaaag agtattcaga aaaatccgtg    780
ggagtgatat acgcctttgc ttggcacgat cctctagcgg aggagtataa ggatgaagta    840
gaggaaatca gaagaaga ctatgagttt gtaacaattc tacactcaaa ggaaagcta    900 gactggatcg gcgtaaacta ctactccagg ctggtatatg gagccaaaga tggacaccta    960
gttcctttac ctggatatgg atttatgagt gagagaggag gatttgcaaa gtcaggaaga   1020
cctgctagtg actttggatg ggaaatgtac ccagagggcc ttgagaacct tcttaagtat   1080
ttaaacaatg cctacgagct accaatgata attacagaga acggtatggc cgatgcagca   1140
gatagataca ggccacacta ctctcgtaagc catctaaagg cagtttacaa tgctatgaaa   1200
gaaggtgctg atgttagagg gtatctccac tggtctctaa cagacaacta cgaatgggcc   1260
caagggttca ggatgagatt tggattggtt acgtggatt tcgagacaaa gaagagatat   1320
ttaaggccaa gcgccctggt attcagagaa atagccactc aaaaagaaat tccagaagaa   1380
ttagctcacc tcgcagacct caaatttgtt acaagaaag                          1419

<210> SEQ ID NO 54
<211> LENGTH: 473

```
<212> TYPE: PRT
<213> ORGANISM: Artificial Sequence
<220> FEATURE:
<223> OTHER INFORMATION: Description of Artificial Sequence: Synthetic
      mutant beta-glucosidase polypeptide having
      glycosylation site
<220> FEATURE:
<221> NAME/KEY: misc_feature
<222> LOCATION: (60)..(62)
<223> OTHER INFORMATION: CARBOHYD
<220> FEATURE:
<221> NAME/KEY: misc_feature
<222> LOCATION: (230)..(232)
<223> OTHER INFORMATION: CARBOHYD

<400> SEQUENCE: 54
```

Met Ala Lys Phe Pro Lys Asn Phe Met Phe Gly Tyr Ser Trp Ser Gly
1               5                   10                  15

Phe Gln Phe Glu Met Gly Leu Pro Gly Ser Glu Val Glu Ser Asp Trp
            20                  25                  30

Trp Val Trp Val His Asp Lys Glu Asn Ile Ala Ser Gly Leu Val Ser
        35                  40                  45

Gly Asp Leu Pro Glu Asn Gly Pro Ala Tyr Trp Asn Arg Thr Lys Gln
    50                  55                  60

Asp His Asp Ile Ala Glu Lys Leu Gly Met Asp Cys Ile Arg Gly Gly
65                  70                  75                  80

Ile Glu Trp Ala Arg Ile Phe Pro Lys Pro Thr Phe Asp Val Lys Val
                85                  90                  95

Asp Val Glu Lys Asp Glu Glu Gly Asn Ile Ile Ser Val Asp Val Pro
            100                 105                 110

Glu Ser Thr Ile Lys Glu Leu Glu Lys Ile Ala Asn Met Glu Ala Leu
        115                 120                 125

Glu His Tyr Arg Lys Ile Tyr Ser Asp Trp Lys Glu Arg Gly Lys Thr
    130                 135                 140

Phe Ile Leu Asn Leu Tyr His Trp Pro Leu Pro Leu Trp Ile His Asp
145                 150                 155                 160

Pro Ile Ala Val Arg Lys Leu Gly Pro Asp Arg Ala Pro Ala Gly Trp
                165                 170                 175

Leu Asp Glu Lys Thr Val Val Glu Phe Val Lys Phe Ala Ala Phe Val
            180                 185                 190

Ala Tyr His Leu Asp Asp Leu Val Asp Met Trp Ser Thr Met Asn Glu
        195                 200                 205

Pro Asn Val Val Tyr Asn Gln Gly Tyr Ile Asn Leu Arg Ser Gly Phe
    210                 215                 220

Pro Pro Gly Tyr Leu Asn Phe Thr Ala Ala Glu Lys Ala Lys Phe Asn
225                 230                 235                 240

Leu Ile Gln Ala His Ile Gly Ala Tyr Asp Ala Ile Lys Glu Tyr Ser
                245                 250                 255

Glu Lys Ser Val Gly Val Ile Tyr Ala Phe Ala Trp His Asp Pro Leu
            260                 265                 270

Ala Glu Glu Tyr Lys Asp Glu Val Glu Ile Arg Lys Lys Asp Tyr
        275                 280                 285

Glu Phe Val Thr Ile Leu His Ser Lys Gly Lys Leu Asp Trp Ile Gly
    290                 295                 300

Val Asn Tyr Tyr Ser Arg Leu Val Tyr Gly Ala Lys Asp Gly His Leu
305                 310                 315                 320

Val Pro Leu Pro Gly Tyr Gly Phe Met Ser Glu Arg Gly Gly Phe Ala
                325                 330                 335

Lys Ser Gly Arg Pro Ala Ser Asp Phe Gly Trp Glu Met Tyr Pro Glu
                340                 345                 350
Gly Leu Glu Asn Leu Leu Lys Tyr Leu Asn Asn Ala Tyr Glu Leu Pro
            355                 360                 365
Met Ile Ile Thr Glu Asn Gly Met Ala Asp Ala Ala Asp Arg Tyr Arg
370                 375                 380
Pro His Tyr Leu Val Ser His Leu Lys Ala Val Tyr Asn Ala Met Lys
385                 390                 395                 400
Glu Gly Ala Asp Val Arg Gly Tyr Leu His Trp Ser Leu Thr Asp Asn
                405                 410                 415
Tyr Glu Trp Ala Gln Gly Phe Arg Met Arg Phe Gly Leu Val Tyr Val
            420                 425                 430
Asp Phe Glu Thr Lys Lys Arg Tyr Leu Arg Pro Ser Ala Leu Val Phe
435                 440                 445
Arg Glu Ile Ala Thr Gln Lys Glu Ile Pro Glu Glu Leu Ala His Leu
                450                 455                 460
Ala Asp Leu Lys Phe Val Thr Arg Lys
465                 470

<210> SEQ ID NO 55
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide encoding mutant beta-glucosidase
      having glycosylation site

<400> SEQUENCE: 55

| | | | | | | |
|---|---|---|---|---|---|---|
| atggcaaagt | tcccaaaaaa | cttcatgttt | ggatattctt | ggtctggttt | ccagtttgag | 60 |
| atgggactgc | caggaagtga | agtggaaagc | gactggtggg | tgtgggttca | cgacaaggag | 120 |
| aacatagcat | caggtctagt | aagtggagat | ctaccagaga | acggcccagc | atattggaac | 180 |
| cgcactaagc | aagatcatga | cattgcagaa | aagctaggaa | tggattgtat | tagaggtggc | 240 |
| attgagtggg | caagaatttt | tccaaagcca | catttgacg | ttaaagttga | tgtggaaaag | 300 |
| gatgaagaag | gcaacataat | tccgtagac | gttccagaga | gtacaataaa | agagctagag | 360 |
| aaaattgcca | acatggaggc | ccttgaacat | tatcgcaaga | tttactcaga | ctggaaggag | 420 |
| aggggcaaaa | ccttcatatt | aaacctctac | cactggcctc | ttccattatg | gattcatgac | 480 |
| ccaattgcag | taaggaaact | tggcccggat | agggctcctg | caggatggtt | agatgagaag | 540 |
| acagtggtag | agtttgtgaa | gtttgccgcc | ttcgttgctt | atcaccttga | tgacctcgtt | 600 |
| gacatgtgga | gcacaatgaa | cgaaccaaac | gtagtctaca | atcaaggtta | cattaatcta | 660 |
| cgttcaggat | tccaccagg | atatctaagc | tttgaagcag | cagaaaaggc | aaaattcaac | 720 |
| ttaattcagg | ctcacatcgg | agcatatgat | gccataaaag | agtattcaga | aaaatccgtg | 780 |
| ggagtgatat | acgcctttgc | ttggcacgat | cctctagcgg | aggagtataa | ggatgaagta | 840 |
| gaggaaatca | gaaagaaaga | ctatgagttt | gtaacaattc | tacactcaaa | aggaaagcta | 900 |
| gactggatcg | gcgtaaacta | ctactccagg | ctggtatatg | gagccaaaga | tggcaccta | 960 |
| gttcctttac | ctggatatgg | atttatgagt | gagagaggag | gatttgcaaa | gtcaggaaga | 1020 |
| cctgctagtg | actttggatg | ggaaatgtac | ccagagggcc | ttgagaacct | tcttaagtat | 1080 |
| ttaaacaata | actacacgct | accaatgata | attacagaga | acggtatggc | cgatgcagca | 1140 |
| gatagataca | ggccacacta | tctcgtaagc | catctaaagg | cagtttacaa | tgctatgaaa | 1200 |

```
gaaggtgctg atgttagagg gtatctccac tggtctctaa cagacaacta cgaatgggcc   1260
caagggttca ggatgagatt tggattggtt tacgtggatt tcgagacaaa gaagagatat   1320
ttaaggccaa gcgccctggt attcagagaa atagccactc aaaagaaat tccagaagaa    1380 ttagctcacc tcgcagacct caaatttgtt acaagaaag                          1419
```

<210> SEQ ID NO 56
<211> LENGTH: 473
<212> TYPE: PRT
<213> ORGANISM: Artificial Sequence
<220> FEATURE:
<223> OTHER INFORMATION: Description of Artificial Sequence: Synthetic
      mutant beta-glucosidase polypeptide having
      glycosylation site
<220> FEATURE:
<221> NAME/KEY: misc_feature
<222> LOCATION: (60)..(62)
<223> OTHER INFORMATION: CARBOHYD
<220> FEATURE:
<221> NAME/KEY: misc_feature
<222> LOCATION: (364)..(366)
<223> OTHER INFORMATION: CARBOHYD

<400> SEQUENCE: 56

```
Met Ala Lys Phe Pro Lys Asn Phe Met Phe Gly Tyr Ser Trp Ser Gly
1               5                   10                  15

Phe Gln Phe Glu Met Gly Leu Pro Gly Ser Glu Val Glu Ser Asp Trp
            20                  25                  30

Trp Val Trp Val His Asp Lys Glu Asn Ile Ala Ser Gly Leu Val Ser
        35                  40                  45

Gly Asp Leu Pro Glu Asn Gly Pro Ala Tyr Trp Asn Arg Thr Lys Gln
    50                  55                  60

Asp His Asp Ile Ala Glu Lys Leu Gly Met Asp Cys Ile Arg Gly Gly
65                  70                  75                  80

Ile Glu Trp Ala Arg Ile Phe Pro Lys Pro Thr Phe Asp Val Lys Val
                85                  90                  95

Asp Val Glu Lys Asp Glu Glu Gly Asn Ile Ile Ser Val Asp Val Pro
            100                 105                 110

Glu Ser Thr Ile Lys Glu Leu Glu Lys Ile Ala Asn Met Glu Ala Leu
        115                 120                 125

Glu His Tyr Arg Lys Ile Tyr Ser Asp Trp Lys Glu Arg Gly Lys Thr
    130                 135                 140

Phe Ile Leu Asn Leu Tyr His Trp Pro Leu Pro Leu Trp Ile His Asp
145                 150                 155                 160

Pro Ile Ala Val Arg Lys Leu Gly Pro Asp Arg Ala Pro Ala Gly Trp
                165                 170                 175

Leu Asp Glu Lys Thr Val Val Glu Phe Val Lys Phe Ala Ala Phe Val
            180                 185                 190

Ala Tyr His Leu Asp Asp Leu Val Asp Met Trp Ser Thr Met Asn Glu
        195                 200                 205

Pro Asn Val Val Tyr Asn Gln Gly Tyr Ile Asn Leu Arg Ser Gly Phe
    210                 215                 220

Pro Pro Gly Tyr Leu Ser Phe Glu Ala Ala Glu Lys Ala Lys Phe Asn
225                 230                 235                 240

Leu Ile Gln Ala His Ile Gly Ala Tyr Asp Ala Ile Lys Glu Tyr Ser
                245                 250                 255

Glu Lys Ser Val Gly Val Ile Tyr Ala Phe Ala Trp His Asp Pro Leu
            260                 265                 270
```

```
Ala Glu Glu Tyr Lys Asp Glu Val Glu Glu Ile Arg Lys Lys Asp Tyr
        275                 280                 285

Glu Phe Val Thr Ile Leu His Ser Lys Gly Lys Leu Asp Trp Ile Gly
        290                 295                 300

Val Asn Tyr Tyr Ser Arg Leu Val Tyr Gly Ala Lys Asp Gly His Leu
305                 310                 315                 320

Val Pro Leu Pro Gly Tyr Gly Phe Met Ser Glu Arg Gly Gly Phe Ala
                325                 330                 335

Lys Ser Gly Arg Pro Ala Ser Asp Phe Gly Trp Glu Met Tyr Pro Glu
            340                 345                 350

Gly Leu Glu Asn Leu Leu Lys Tyr Leu Asn Asn Tyr Thr Leu Pro
        355                 360                 365

Met Ile Ile Thr Glu Asn Gly Met Ala Asp Ala Ala Asp Arg Tyr Arg
        370                 375                 380

Pro His Tyr Leu Val Ser His Leu Lys Ala Val Tyr Asn Ala Met Lys
385                 390                 395                 400

Glu Gly Ala Asp Val Arg Gly Tyr Leu His Trp Ser Leu Thr Asp Asn
                405                 410                 415

Tyr Glu Trp Ala Gln Gly Phe Arg Met Arg Phe Gly Leu Val Tyr Val
            420                 425                 430

Asp Phe Glu Thr Lys Lys Arg Tyr Leu Arg Pro Ser Ala Leu Val Phe
        435                 440                 445

Arg Glu Ile Ala Thr Gln Lys Glu Ile Pro Glu Glu Leu Ala His Leu
        450                 455                 460

Ala Asp Leu Lys Phe Val Thr Arg Lys
465                 470
```

```
<210> SEQ ID NO 57
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtgggtgtgg gttaacgaca cggagaacat agcatc                          36

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cacccacacc caattgctgt gcctcttgta tcgtag                          36

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccaggatatc taaactttac agcagcagaa aaggca                          36
```

```
<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggtcctatag atttgaaatg tcgtcgtctt ttccgt                                 36

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
agtatttaaa caataactac acgctaccaa tgata                                  35

<210> SEQ ID NO 62
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcataaattt gttattgatg tgcgatggtt actat                                  35

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid except Pro
<220> FEATURE:
<221> NAME/KEY: MOD_RES
<222> LOCATION: (4)..(4)
<223> OTHER INFORMATION: Any amino acid except Pro

<400> SEQUENCE: 63

Cys Xaa Ser Xaa Pro Cys
1               5
```